US011096668B2

(12) United States Patent
Lee et al.

(10) Patent No.: US 11,096,668 B2
(45) Date of Patent: Aug. 24, 2021

(54) METHOD AND ULTRASOUND APPARATUS FOR DISPLAYING AN OBJECT

(71) Applicant: SAMSUNG ELECTRONICS CO., LTD., Suwon-si (KR)

(72) Inventors: Jae-ho Lee, Seoul (KR); Soon-jae Hong, Seongnam-si (KR); Myong-woo Lee, Seongnam-si (KR); Gi-hun Yun, Goyang-si (KR); Su-jin Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1103 days.

(21) Appl. No.: 15/375,444

(22) Filed: Dec. 12, 2016

(65) Prior Publication Data

US 2017/0090675 A1    Mar. 30, 2017

Related U.S. Application Data

(63) Continuation-in-part of application No. 14/205,762, filed on Mar. 12, 2014, now abandoned.
(Continued)

(30) Foreign Application Priority Data

Apr. 11, 2013  (KR) .................. 10-2013-0040025
Jun. 13, 2013  (KR) .................. 10-2013-0067943
Feb. 23, 2016  (KR) .................. 10-2016-0021326

(51) Int. Cl.
*A61B 8/00* (2006.01)
*A61B 8/08* (2006.01)
(Continued)

(52) U.S. Cl.
CPC ............... *A61B 8/48* (2013.01); *A61B 8/462* (2013.01); *A61B 8/463* (2013.01); *A61B 8/465* (2013.01);
(Continued)

(58) Field of Classification Search
CPC ..... A61B 8/0858; A61B 8/4427; A61B 8/462; A61B 8/463; A61B 8/465; A61B 8/467;
(Continued)

(56) References Cited

U.S. PATENT DOCUMENTS 6,259,436 B1   7/2001  Moon et al.
7,489,306 B2   2/2009  Kolmykov-Zotov et al.
(Continued)

FOREIGN PATENT DOCUMENTS

CN        1126021 C      10/2003
CN      101627361 A       1/2010
(Continued)

OTHER PUBLICATIONS

Gleicher, Micheal, "Image Snapping", Advanced Technology Group, Apple Computer, Inc. (Year: 1995).*
(Continued)

*Primary Examiner* — Christopher L Cook
(74) *Attorney, Agent, or Firm* — Sughrue Mion, PLLC

(57) ABSTRACT

An ultrasound apparatus includes a touch screen configured to display, on an ultrasound image, a touch recognition region of an object used as a measurement mark; and a controller configured to move the object and the touch recognition region, in response to an input for touching and dragging the touch recognition region, to detect, from a portion of the ultrasound image which corresponds to the touch recognition region, a line formed by connecting points at which a brightness variation of a pixel is greater than a threshold value, and to move the object to a position of the detected line by using coordinates of the detected line.

22 Claims, 49 Drawing Sheets

Related U.S. Application Data

(60) Provisional application No. 61/779,520, filed on Mar. 13, 2013.

(51) Int. Cl.
*G06F 3/0488* (2013.01)
*G06T 7/62* (2017.01)
*G06F 3/0484* (2013.01)
*G01S 7/52* (2006.01)

(52) U.S. Cl.
CPC .............. *A61B 8/467* (2013.01); *A61B 8/468* (2013.01); *A61B 8/469* (2013.01); *A61B 8/54* (2013.01); *G06F 3/0488* (2013.01); *G06F 3/04845* (2013.01); *G06T 7/62* (2017.01); *A61B 8/0858* (2013.01); *A61B 8/4427* (2013.01); *A61B 8/483* (2013.01); *A61B 8/485* (2013.01); *A61B 8/486* (2013.01); *A61B 8/488* (2013.01); *A61B 8/5223* (2013.01); *G01S 7/52073* (2013.01); *G01S 7/52074* (2013.01); *G01S 7/52084* (2013.01); *G06F 2203/04806* (2013.01); *G06F 2203/04807* (2013.01); *G06T 2207/10132* (2013.01); *G06T 2207/20104* (2013.01); *G06T 2207/30004* (2013.01)

(58) Field of Classification Search
CPC ........... A61B 8/468; A61B 8/469; A61B 8/48; A61B 8/483; A61B 8/485; A61B 8/486; A61B 8/488; A61B 8/5223; A61B 8/54; G01S 7/52073; G01S 7/52074; G01S 7/52084; G06F 2203/04806; G06F 2203/04807

See application file for complete search history.

(56) References Cited

U.S. PATENT DOCUMENTS

| | | | |
|---|---|---|---|
| 7,948,493 B2 | 5/2011 | Klefenz et al. | |
| 8,127,248 B2 | 2/2012 | Ording et al. | |
| 8,407,606 B1 | 3/2013 | Davidson et al. | |
| 8,519,963 B2 | 8/2013 | Kocienda et al. | |
| 8,552,999 B2 | 10/2013 | Dale et al. | |
| 8,896,621 B1 | 11/2014 | Sipher et al. | |
| 9,086,757 B1 * | 7/2015 | Desai | B25J 13/06 |
| 9,311,712 B2 | 4/2016 | Fukata | |
| 2002/0018051 A1 | 2/2002 | Singh | |
| 2004/0119763 A1 | 6/2004 | Mizobuchi et al. | |
| 2006/0161846 A1 | 7/2006 | Van Leeuwen | |
| 2007/0299342 A1 | 12/2007 | Hayasaka | |
| 2008/0118237 A1 | 5/2008 | Wegenkittl et al. | |
| 2008/0119731 A1 | 5/2008 | Becerra et al. | |
| 2008/0122796 A1 | 5/2008 | Jobs et al. | |
| 2008/0165160 A1 | 7/2008 | Kocienda et al. | |
| 2008/0221446 A1 | 9/2008 | Washburn | |
| 2009/0043195 A1 | 2/2009 | Poland | |
| 2009/0270868 A1 | 10/2009 | Park et al. | |
| 2010/0004539 A1 | 1/2010 | Chen et al. | |
| 2010/0094132 A1 | 4/2010 | Hansen et al. | |
| 2010/0179427 A1 | 7/2010 | Yamamoto | |
| 2010/0217128 A1 | 8/2010 | Betts | |
| 2010/0235793 A1 | 9/2010 | Ording et al. | |
| 2010/0278424 A1 * | 11/2010 | Warner | G06F 3/04842 382/173 |
| 2010/0298701 A1 | 11/2010 | Shin | |
| 2010/0305444 A1 | 12/2010 | Fujii et al. | |
| 2010/0315437 A1 | 12/2010 | Sinclair, II et al. | |
| 2010/0321324 A1 | 12/2010 | Fukai et al. | |
| 2011/0043434 A1 | 2/2011 | Roncalez et al. | |
| 2011/0066031 A1 | 3/2011 | Lee et al. | |
| 2011/0078597 A1 | 3/2011 | Rapp et al. | |
| 2011/0107258 A1 | 5/2011 | Chen | |
| 2011/0112399 A1 | 5/2011 | Willems et al. | |
| 2011/0224546 A1 | 9/2011 | Lee et al. | |
| 2011/0246876 A1 | 10/2011 | Chutani et al. | |
| 2011/0262018 A1 * | 10/2011 | Kumar | G06T 7/0012 382/131 |
| 2011/0281619 A1 | 11/2011 | Cho et al. | |
| 2011/0295120 A1 | 12/2011 | Lee | |
| 2012/0030569 A1 | 2/2012 | Migos et al. | |
| 2012/0179039 A1 | 7/2012 | Pelissier et al. | |
| 2013/0012314 A1 | 1/2013 | Ishikawa | |
| 2013/0019201 A1 | 1/2013 | Cabrera-Cordon et al. | |
| 2013/0152013 A1 | 6/2013 | Forstall et al. | |
| 2013/0179816 A1 | 7/2013 | Seo et al. | |
| 2013/0245428 A1 | 9/2013 | Banjanin | |
| 2013/0316817 A1 | 11/2013 | Tanzawa et al. | |
| 2013/0318475 A1 | 11/2013 | Xie | |
| 2013/0324850 A1 | 12/2013 | Petruzzelli et al. | |
| 2013/0331182 A1 | 12/2013 | Tanzawa et al. | |
| 2013/0345563 A1 | 12/2013 | Stuebe et al. | |
| 2014/0098049 A1 | 4/2014 | Koch et al. | |
| 2014/0114190 A1 | 4/2014 | Chiang et al. | |
| 2014/0121524 A1 | 5/2014 | Chiang et al. | |
| 2014/0181753 A1 | 6/2014 | Kamii et al. | |
| 2014/0198055 A1 | 7/2014 | Barkway | |
| 2014/0317545 A1 | 10/2014 | Miyazaki | |
| 2015/0094578 A1 | 4/2015 | Ninomiya et al. | |
| 2015/0141823 A1 * | 5/2015 | Lee | A61B 8/54 600/440 |

FOREIGN PATENT DOCUMENTS

| | | |
|---|---|---|
| CN | 102006828 A | 4/2011 |
| CN | 102316263 A | 1/2012 |
| CN | 202235453 U | 5/2012 |
| CN | 102626326 A | 8/2012 |
| CN | 102793565 A | 11/2012 |
| EP | 2191776 A1 | 6/2010 |
| EP | 2255730 A1 | 12/2010 |
| EP | 2 532 307 A1 | 12/2012 |
| JP | 10-314167 A | 12/1998 |
| JP | 2005-137747 A | 6/2005 |
| JP | 2007-97816 A | 4/2007 |
| JP | 2008-486 A | 1/2008 |
| JP | 2009-510571 A | 3/2009 |
| JP | 2009-207589 A | 9/2009 |
| JP | 2009-213507 A | 9/2009 |
| JP | 2009-213796 A | 9/2009 |
| JP | 2010-142563 A | 7/2010 |
| JP | 2010-269139 A | 12/2010 |
| JP | 2012-19824 A | 2/2012 |
| JP | 2012-203644 A | 10/2012 |
| KR | 10-2006-0072082 A | 6/2006 |
| KR | 10-2010-0110893 A | 10/2010 |
| KR | 10-2011-0029630 A | 3/2011 |
| KR | 10-1095851 B1 | 12/2011 |
| KR | 10-2012-0036420 A | 4/2012 |
| KR | 10-1167248 B1 | 7/2012 |
| KR | 10-1176657 B1 | 8/2012 |
| KR | 10-2013-0018870 A | 2/2013 |
| WO | 2006/040697 A1 | 4/2006 |
| WO | 2009/049363 A1 | 4/2009 |
| WO | 2009/109585 A1 | 9/2009 |
| WO | 2013/148730 A2 | 10/2013 |

OTHER PUBLICATIONS

Communication dated Jun. 13, 2016 issued by the State Intellectual Property Office of P.R. China in counterpart Chinese Application No. 201510552566.X.

Communication dated May 24, 2016 issued by Korean Intellectual Property Office in counterpart Korean Patent Application No. 10-2013-0067943.

Search Report dated May 20, 2014, issued by the International Searching Authority in counterpart International Application No. PCT/KR2014/001848.

Written Opinion dated May 20, 2014, issued by the International Searching Authority in counterpart International Application No. PCT/KR2014/001848.

(56) References Cited

OTHER PUBLICATIONS

Communication dated Jul. 17, 2014, issued by the European Patent Office in counterpart European Application No. 14159249.3.
Communication dated Mar. 26, 2015 by the European Patent Office in related Application No. 14196386.8.
"A Gmail Miscellany", posted online Nov. 14, 2012, accessed online Jul. 21, 2015, 24 pages total.
Communication dated Jul. 31, 2015, issued by the United States Patent and Trademark Office in counterpart U.S. Appl. No. 14/582,415.
Communication dated Aug. 3, 2015, issued by the State Intellectual Property Office of the People's Republic of China in counterpart Chinese Application No. 201410094048.3.
Communication dated Sep. 25, 2015, issued by the European Patent Office in counterpart European Application No. 15172744.0.
Communication dated Oct. 29, 2015 issued by the Korean Intellectual Property Office in counterpart Application No. 10-2013-0040025.
Communication dated Dec. 19, 2015 issued by the Korean Intellectual Property Office in counterpart Application No. 10-2013-0067943.
Communication dated Jan. 29, 2016 issued by the United States Patent and Trademark Office in counterpart U.S. Appl. No. 14/582,415.
Communication dated Feb. 15, 2016, issued by the Japanese Patent Office in counterpart Japanese Patent Application No. 2015-562903.
Communication dated Mar. 21, 2016, issued by the European Patent Office in counterpart European Patent Application No. 15191427.2.
Communication dated Apr. 28, 2016, issued by the Korean Intellectual Property Office in counterpart Korean Patent Application No. 10-2013-0040025.
"How do I use multi-touch to move more than one object?", available online Feb. 11, 2012, accessed online Dec. 2, 2015, pp. 1-3.
Office Action dated Oct. 20, 2016 issued in corresponding EP Application No. 15191427.2 , 3 pages.
Office Action dated Oct. 24, 2016 issued in corresponding EP Application No. 14159249.3 together with attachment, 10 pages.
Office Action dated Oct. 27, 2016 issued in corresponding KR Application No. 10-2013-0040025, 3 pages.
Communication dated Mar. 10, 2017 by the State Intellectual Property Office of P.R. China in counterpart Chinese Patent Application No. 201510552566.X.
Communication dated Apr. 3, 2017 by the European Patent Office in counterpart European Patent Application No. 15172774.0.
Communication dated May 16, 2018, from the European Patent Office in counterpart European Application No. 18155774.5.
Communication dated Feb. 21, 2018, from the European Patent Office in counterpart European Application No. 15172774.0.
Communication dated Apr. 2, 2018, from the State Intellectual Property Office of People's Republic of China in counterpart Application No. 201510552566.X.
Communication dated Mar. 1, 2019, issued by the State Intellectual Property Office of P.R. China in counterpart Chinese Application No. 201510552566.X.
Communication dated Dec. 16, 2015, issued by the United States Patent and Trademark Office in counterpart U.S. Appl. No. 14/205,762.
Communication from United States Patent and Trademark Office dated Jun. 27, 2016, in U.S. Appl. No. 14/205,762.
Communication dated Mar. 22, 2017, issued by the United States Patent and Trademark Office in counterpart U.S. Appl. No. 14/205,762.
Communication dated Apr. 18, 2017, issued by the United States Patent and Trademark Office in counterpart U.S. Appl. No. 14/205,762.
Communication dated Sep. 26, 2017, issued by the United States Patent and Trademark Office in counterpart U.S. Appl. No. 14/205,762.
Communication dated Apr. 5, 2018, issued by the United States Patent and Trademark Office in counterpart U.S. Appl. No. 14/205,762.
Communication dated Oct. 12, 2018, issued by the United States Patent and Trademark Office in counterpart U.S. Appl. No. 14/205,762.
Anonymous, "SMART Board—Level 1—3e—Manipulation Objects—Infinite Cloner", You Tube Video Published Feb. 29, 2012 at httsp://www.youtube.com/watch?v=RPRE_2J9YA.
Anonymous, "Complete SMART Board Tutorial", You Tube Video published Jan. 28, 2010 at https://www.youtube.com/watch?v=dwla8E6jz4g.
Decision to Grant dated Jul. 13, 2017 in EP 15191427.2.
Communication dated Apr. 25, 2019, issued by the United States Patent and Trademark Office in counterpart U.S. Appl. No. 14/631,183.
Communication dated Nov. 20, 2018, issued by the United States Patent and Trademark Office in counterpart U.S. Appl. No. 14/631,183.
Communication dated May 2, 2018, issued by the United States Patent and Trademark Office in counterpart U.S. Appl. No. 14/631,183.
Communication dated Mar. 5, 2019, issued by the United States Patent and Trademark Office in counterpart U.S. Appl. No. 14/582,415.
Communication dated Mar. 7, 2018, issued by the United States Patent and Trademark Office in counterpart U.S. Appl. No. 14/582,415.
Communication dated Aug. 16, 2018, issued by the United States Patent and Trademark Office in counterpart U.S. Appl. No. 14/582,415.
Communication dated Oct. 12, 2017, issued by the United States Patent and Trademark Office in counterpart U.S. Appl. No. 14/582,415.
Communication dated Mar. 20, 2017, issued by the United States Patent and Trademark Office in counterpart U.S. Appl. No. 14/582,415.
Communication dated Mar. 13, 2019, issued by the United States Patent and Trademark Office in counterpart U.S. Appl. No. 14/521,627.
Communication dated Nov. 15, 2018, issued by the United States Patent and Trademark Office in counterpart U.S. Appl. No. 14/521,627.
Communication dated Apr. 2, 2018, issued by the United States Patent and Trademark Office in counterpart U.S. Appl. No. 14/521,627.
Communication dated Nov. 30, 2017, issued by the United States Patent and Trademark Office in counterpart U.S. Appl. No. 14/521,627.
Communication dated May 9, 2014, issued by the United States Patent and Trademark Office in counterpart U.S. Appl. No. 14/205,762.
Communication dated Jan. 10, 2019, issued by the United States Patent and Trademark Office in counterpart U.S. Appl. No. 14/205,762.
Communication dated May 17, 2019, issued by the Chinese Patent Office in counterpart Chinese Application No. 201510552566.X.
Communication dated Nov. 8, 2019 issued by the United States Patent and Trademark Office in counterpart U.S. Appl. No. 14/631,183.
Communication dated Nov. 27, 2019, issued by the United States Patent and Trademark Office in counterpart U.S. Appl. No. 14/582,415.
Communication dated Nov. 4, 2019 issued by the State Intellectual Property Office of P.R. China in counterpart Chinese Application No. 201510552566.X.
Communication dated Dec. 10, 2019 issued by the Indian Intellectual Property Office in Indian counterpart Application No. 2752/MUMNP/2015.
Communication dated Sep. 27, 2018 issued by the European Patent Office in counterpart European Application No. 15172774.0.
Communication dated Nov. 24, 2016, issued by the State Intellectual Property Office of P.R. China in counterpart Chinese Application No. 201510552566.X.
Communication dated Mar. 5, 2020 issued by the Chinese Patent Office in counterpart Chinese Application No. 201510552566.X, total of 27 pages with translation.
Communication dated May 20, 2020, issued by the State Intellectual Property Office of P.R. China in counterpart Chinese Application No. 201510552566.X.
Communication dated Apr. 14, 2020 issued by the United States Patent and Trademark Office in counterpart U.S. Appl. No. 14/631,183.
Communication dated Aug. 10, 2020, from the State Intellectual Property Office of People's Republic of China in counterpart Application No. 201510552566.X.

* cited by examiner

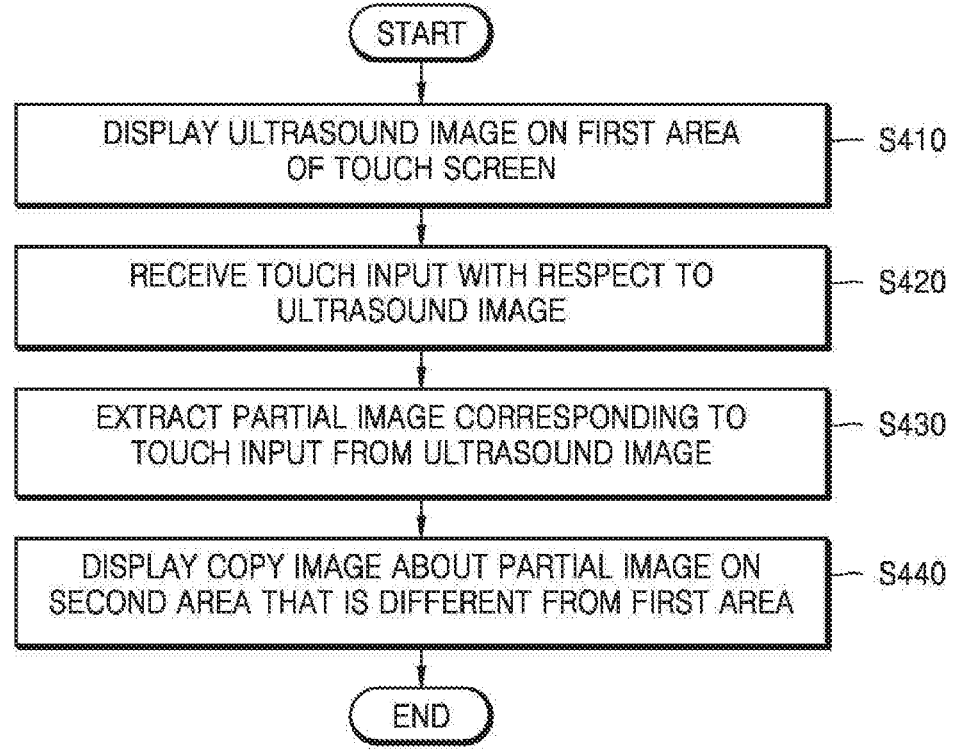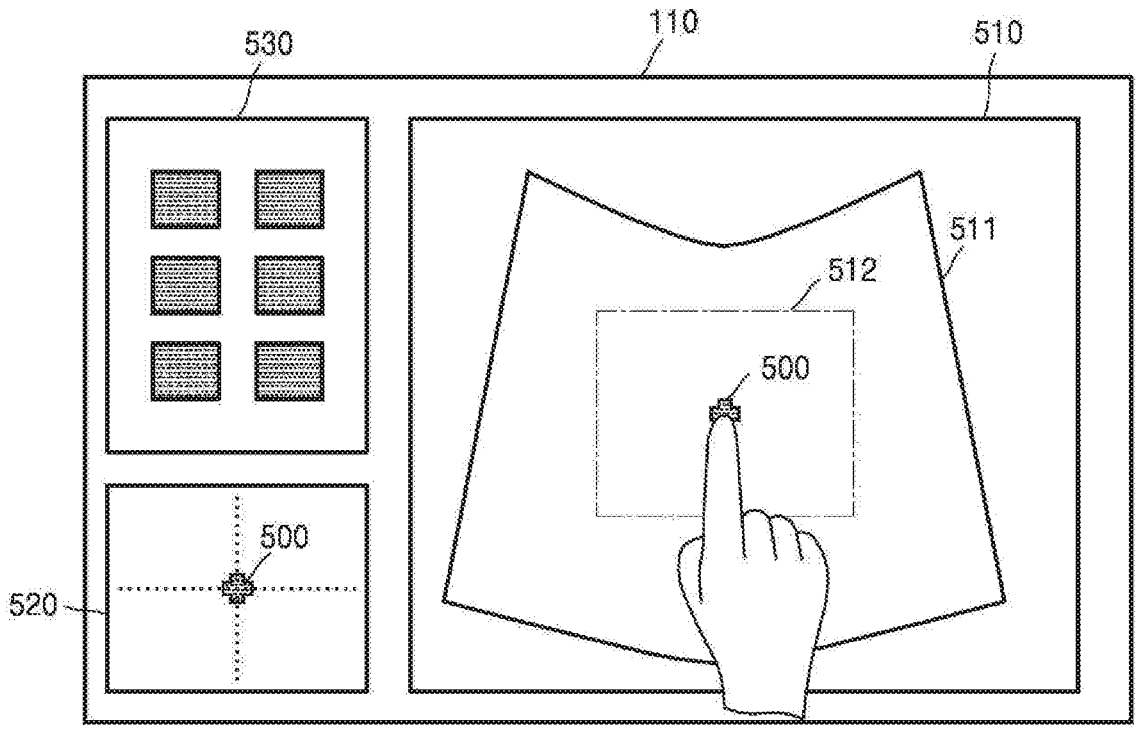

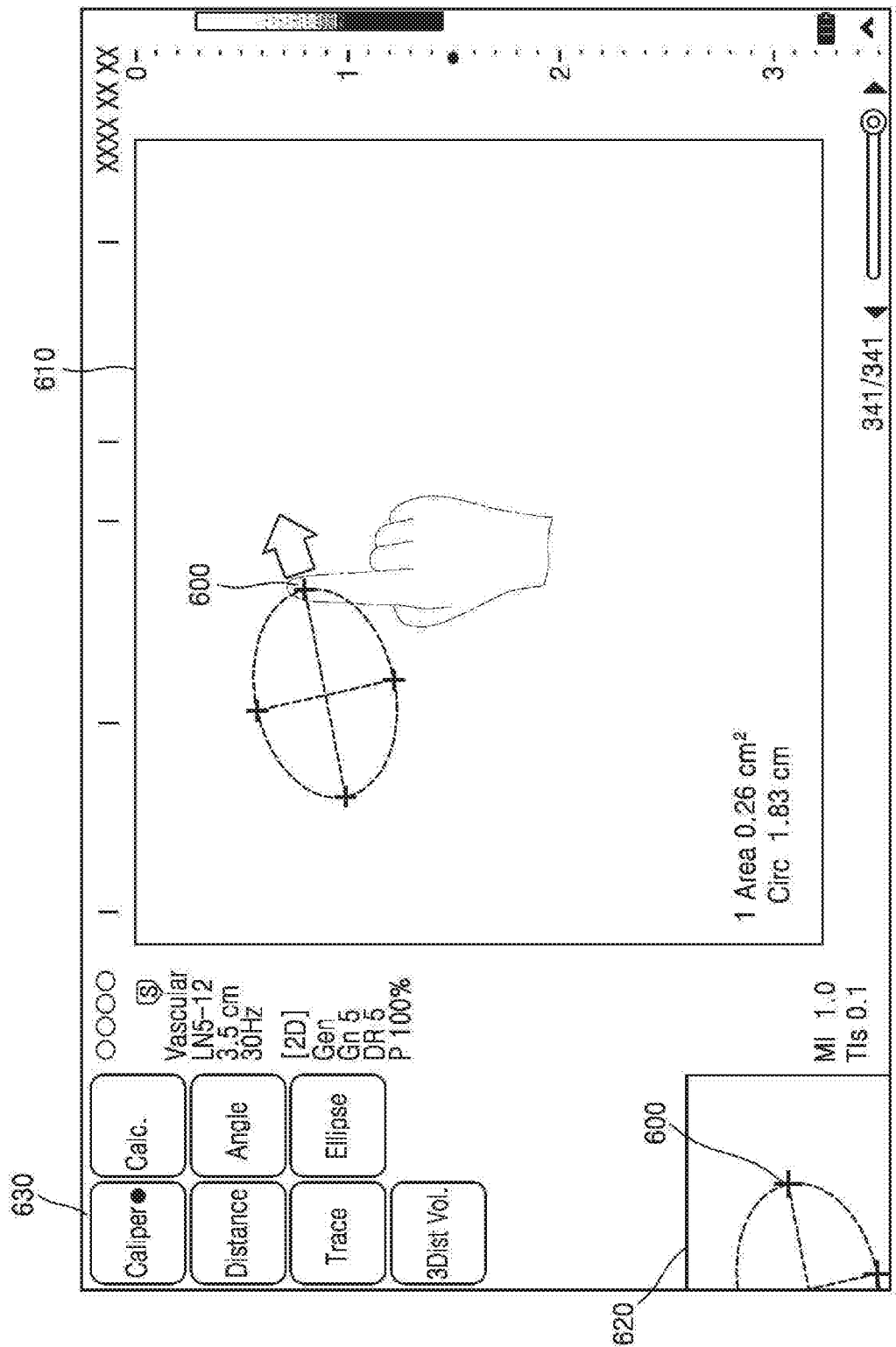

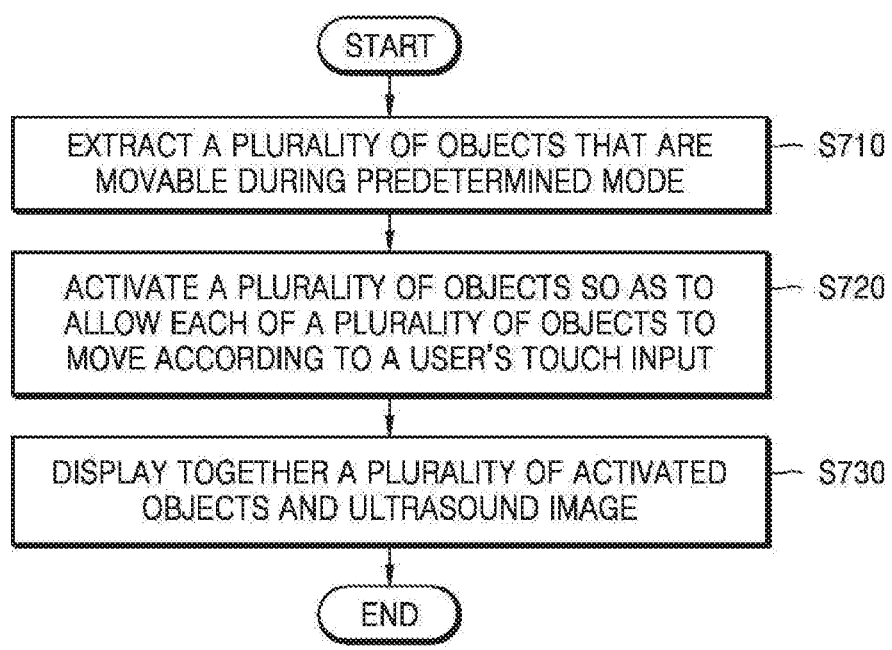

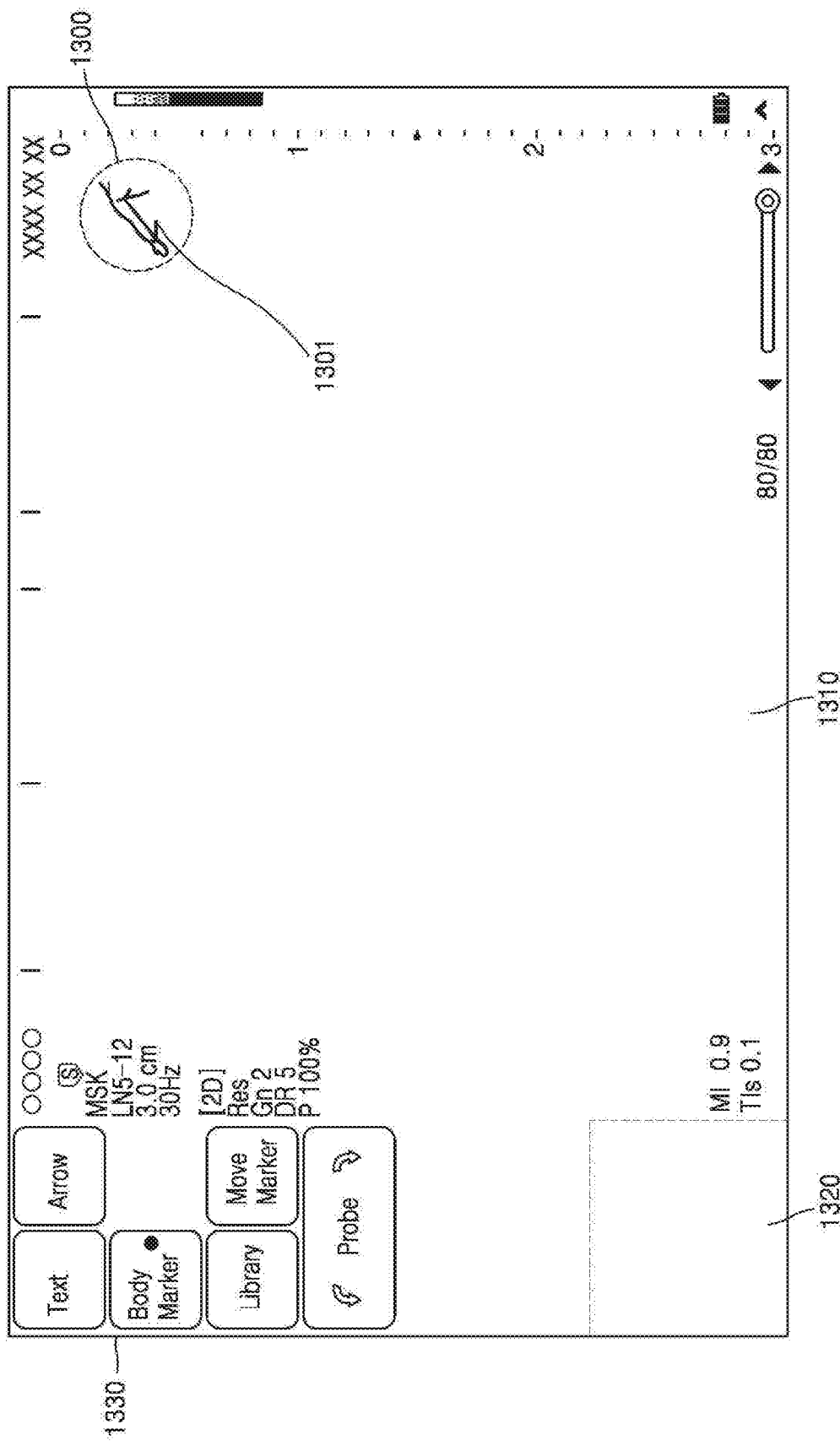

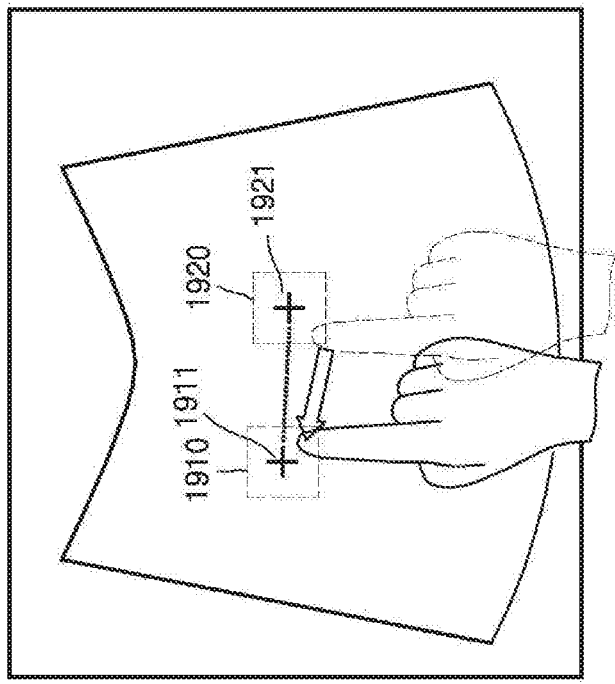
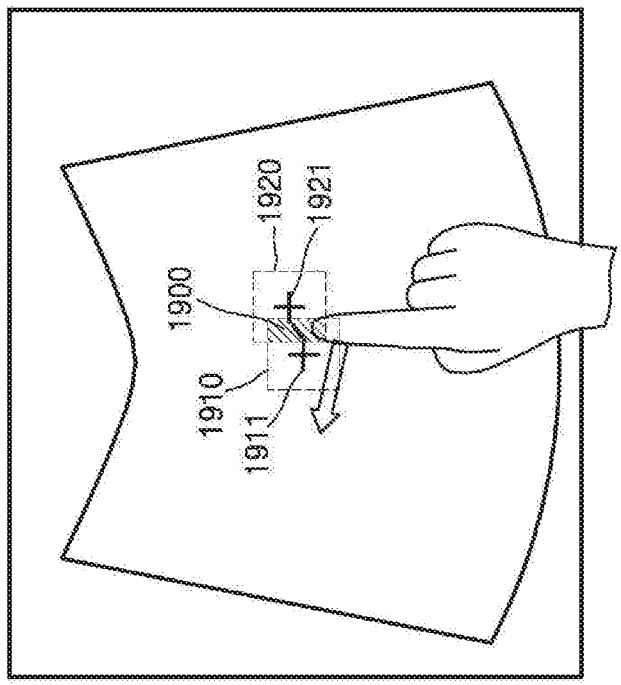

FIG. 36
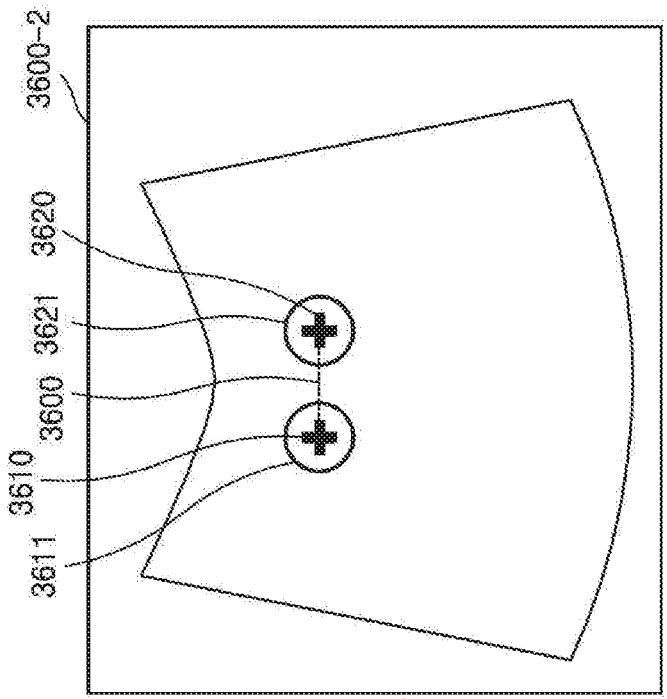
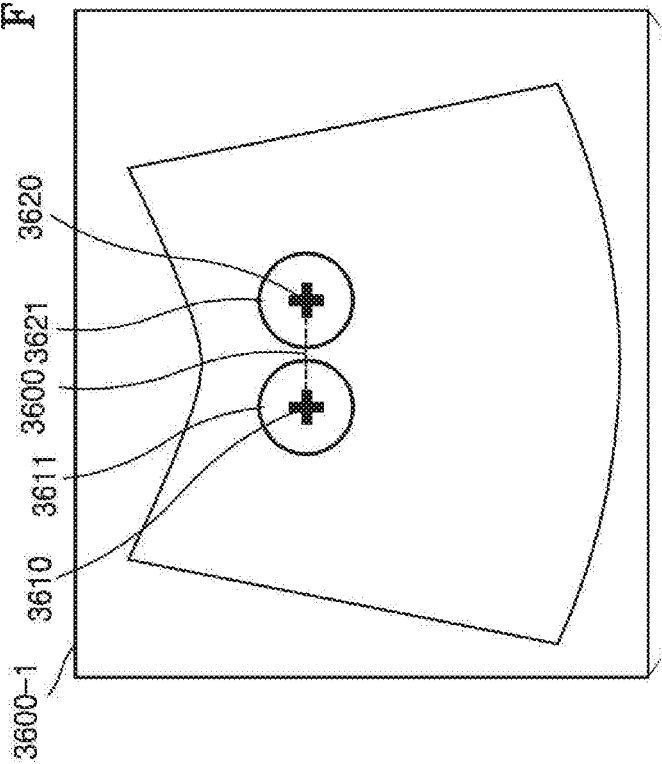
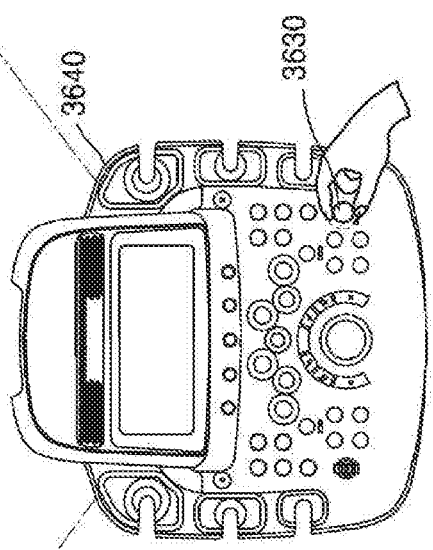

METHOD AND ULTRASOUND APPARATUS FOR DISPLAYING AN OBJECT

CROSS-REFERENCE TO RELATED PATENT APPLICATIONS

This application is a continuation-in-part of U.S. patent application Ser. No. 14/205,762, filed on Mar. 12, 2014, which claims the benefit of U.S. Provisional Patent Application No. 61/779,520, filed on Mar. 13, 2013, and claims priority from Korean Patent Application Nos. 10-2013-0040025, filed on Apr. 11, 2013, and 10-2013-0067943, filed on Jun. 13, 2013 in the Korean Intellectual Property Office. Further, this application claims priority from Korean Patent Application No. 10-2016-0021326, filed on Feb. 23, 2016, in the Korean Intellectual Property Office. The disclosures of all of the above applications are incorporated herein by reference in their entireties.

BACKGROUND

1. Field

The disclosure is related to a method of displaying an object on an ultrasound image, and an ultrasound diagnostic apparatus therefor.

2. Description of the Related Art

An ultrasound diagnostic apparatus transmits an ultrasound signal from a body surface to a predetermined part inside a human body, and obtains an image of a cross-section of or a blood flow in a soft tissue by using information of the reflected ultrasound signal.

The ultrasound diagnostic apparatus is advantageous in that the ultrasound diagnostic apparatus is small, inexpensive, and capable of displaying an image in real-time. Also, the ultrasound diagnostic apparatus is safe without a risk of radioactivity due to an X-ray or the like, such that the ultrasound diagnostic apparatus may be widely used with other image diagnostic apparatuses such as an X-ray diagnostic apparatus, a computed tomography (CT) scanner, a magnetic resonance imaging (MRI) apparatus, a nuclear medicine diagnostic apparatus, or the like.

Values that are measured by using the ultrasound diagnostic apparatus are highly related to a lesion diagnosis or the like, and thus the values have to be exact. Thus, apparatuses and methods are needed to allow a user to exactly select a measurement portion. Also, apparatuses and methods are needed to allow a user who uses a touch interface to freely adjust a length and position of a measurement line.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide a method of providing a copy image and an ultrasound apparatus therefor, whereby the copy image of a part that is obstructed by a touch instrument (such as a finger, an electronic pen, or the like) is separately provided at a predetermined area, thus, a user may exactly select a measurement portion or a selection portion of an ultrasound image.

According to an aspect of an exemplary embodiment, there is provided a method of providing a copy image, the method including displaying an ultrasound image on a first area of a touch screen; receiving a touch input with respect to the ultrasound image; extracting a partial image corresponding to the touch input from the ultrasound image; and displaying a copy image of the partial image on a second area that is different from the first area on which the ultrasound image is displayed.

The extracting of the partial image may include obtaining information about a position on the touch screen at which the touch input is received; and extracting a copy image having a preset size with respect to the position.

The displaying of the copy image may include capturing the partial image corresponding to the touch input; and displaying the captured partial image as the copy image on the second area.

The displaying of the copy image may be performed so that an object that is displayed at a position on the touch screen at which the touch input is received may be located at a center of the second area.

The object may include at least one of a reference point for selection of a measurement portion or a measurement area, a sample volume, a body marker, an arrow, and an annotation.

The method may further include displaying a plurality of objects on the first area, wherein each of the plurality of objects is activated to be moved according to the touch input.

The displaying of the copy image may include changing a control panel for adjustment of a parameter value related to the ultrasound image, according to a predetermined mode, and then displaying the changed control panel on a third area of the touch screen; selecting the second area that is different from the first area and the third area; and displaying the copy image on the second area.

The predetermined mode may include at least one of a brightness mode (B mode), a Doppler mode, and a motion mode (M mode).

The displaying of the copy image may include receiving a drag input that starts at a position on the touch screen at which the touch input is received; and displaying the copy image of the partial image on the second area, wherein the partial image is changed according to the drag input.

The displaying of the copy image may include moving an object, which is displayed at a position on the touch screen at which the touch input is received, according to the drag input and then displaying the object on the first area.

The receiving of the touch input may include receiving multiple touch inputs with respect to at least two portions of the ultrasound image, and the operation of displaying the copy image may include an operation of displaying a plurality of copy images about a plurality of partial images on the second area, wherein the plurality of partial images correspond to the at least two portions, respectively.

The displaying of the copy image may include displaying the copy image on the second area, wherein the copy image is magnified or reduced by a predetermined ratio.

When the touch input is no longer received, the method may further include an operation of removing the copy image from the second area.

The second area does not overlap with the first area on which the ultrasound image is displayed.

The second area may include a residual area of the first area on which the ultrasound image is displayed, wherein the residual area excludes an interest area that is selected by a user.

According to an aspect of an exemplary embodiment, there is provided an ultrasound apparatus including a display for displaying an ultrasound image on a first area of a touch screen; a user input unit for receiving a touch input with respect to the ultrasound image; and a controller for extracting a partial image corresponding to the touch input from the ultrasound image, and for controlling the display to display a copy image of the partial image on a second area that is different from the first area on which the ultrasound image is displayed.

The controller may obtain information about a position on the touch screen at which the touch input is received, and may extract a copy image having a preset size with respect to the position.

The ultrasound apparatus may further include an image processor for generating the copy image by capturing the partial image corresponding to the touch input.

The display may display the copy image so that an object that is displayed at a position at which the touch input is received may be located at a center of the second area.

The display may further display a plurality of objects on the first area, wherein each of the plurality of objects is activated to be moved according to the touch input.

The display may change a control panel for adjustment of a parameter value related to the ultrasound image, according to a predetermined mode, and then may display the control panel on a third area of the touch screen, and the controller may select the second area that is different from the first area and the third area.

The user input unit may receive a drag input that starts at a position (at which the touch input is received, and the display may display the copy image of the partial image on the second area, wherein the partial image is changed according to the drag input.

The user input unit may receive multiple touch inputs with respect to at least two portions of the ultrasound image, and the display may display a plurality of copy images about a plurality of partial images on the second area, wherein the plurality of partial images correspond to the at least two portions, respectively.

The display may display the copy image on the second area, wherein the copy image is magnified or reduced by a predetermined ratio.

When the touch input is no longer received, the display may remove the copy image from the second area.

According to an aspect of an exemplary embodiment, there is provided a method of providing a copy image, the method including outputting an ultrasound signal to a target via a probe, and receiving an ultrasound response signal from the target; generating an ultrasound image about the target base on the ultrasound response signal; displaying the ultrasound image about the target on a first area of a touch screen; receiving a touch input by a user with respect to the ultrasound image; and displaying a copy image of a partial image on a second area that is different from the first area on which the ultrasound image is displayed, wherein the partial image corresponds to the touch input.

The ultrasound image about the target may be changed according to a position or an angle of the probe.

According to an aspect of an exemplary embodiment, there is provided a method of providing a copy image, the method including displaying a body marker including a target figure and a probe figure on a first area of a touch screen; receiving a touch input by a user with respect to the body marker; and displaying a copy image of the body marker on a second area that is different from the first area, based on the touch input.

The displaying of the copy image may be performed so that the target figure may be located at a center of the second area.

The method may further include receiving a drag input that involves moving the probe figure displayed on the first area; moving a position of the probe figure, based on the drag input; and displaying a body marker including the target figure and the moved probe figure on the first area.

The method may further include displaying a changed copy image, which is changed according to the drag input, on the second area.

The displaying of the changed copy image may include displaying a copy image of the body marker including the target figure and the moved probe figure on the second area.

One or more of exemplary embodiments provide a method and an ultrasound apparatus for displaying a plurality of objects related to an ultrasound image by activating the plurality of objects, whereby each of the plurality of objects may be moved according to a user's touch input.

One or more of exemplary embodiments provide a method and an ultrasound apparatus for displaying an object by expanding a touch recognition range of the object, whereby, when a user exactly touches an object by using a touch instrument (e.g., a finger or an electronic pen) but the object is obstructed by the touch instrument, the user may move the object although the user touches an area around the object.

One or more of exemplary embodiments provide a method and an ultrasound apparatus for displaying a plurality of objects, whereby, when touch recognition ranges of the plurality of objects overlap with each other, a movement order of the plurality of objects is determined according to priority orders.

The method may include extracting the plurality of objects that are movable during a predetermined mode; activating the plurality of objects to allow each of the plurality of objects to be moved according to a user's touch input; and displaying together the plurality of activated objects and an ultrasound image.

Each of the plurality of activated objects may include at least one of a reference point, a reference line, annotation, and an arrow which are used in selecting a measurement point or a measurement area.

The method may further include receiving a touch and drag input with respect to at least one object among the plurality of activated objects; and moving and displaying the at least one object according to the touch and drag input.

The moving and displaying may include receiving a touch and drag input with respect to a first area within a predetermined radius from a point at which a first object among the plurality of activated objects is displayed; moving and displaying the first object according to the touch and drag input with respect to the first area; receiving a touch and drag input with respect to a second area within the predetermined radius from a point at which a second object among the plurality of activated objects is displayed; and moving and displaying the second object according to the touch and drag input with respect to the second area.

The method may further include receiving a touch and drag input with respect to an area in which the first area and the second area overlap with each other; and moving and displaying at least one of the first object and the second object, based on priority order information.

The moving and displaying at least one of the first object and the second object may include comparing movement time information of the first object with movement time information of the second object; and move and displaying one of the first object and the second object according to a result of the comparing.

The method may further include receiving multiple touch inputs with respect to the first object and the second object included in the plurality of activated objects; and moving and displaying the first object and the second object, respectively, according to the multiple touch inputs.

The ultrasound image may include at least one of a B mode image, Doppler image, an M mode image, and an elasticity mode image.

The ultrasound apparatus may include a user input unit for receiving a user's touch input; a controller for extracting the plurality of objects that are movable during a predetermined mode, and activating the plurality of objects to allow each of the plurality of objects to be moved according to the user's touch input; and a display for displaying together the plurality of activated objects and an ultrasound image.

The user input unit may receive a touch and drag input with respect to at least one object among the plurality of activated objects, and the display may move and display the at least one object according to the touch and drag input.

The user input unit may receive a touch and drag input with respect to a first area within a predetermined radius from a point at which a first object among the plurality of activated objects is displayed, and may receive a touch and drag input with respect to a second area within the predetermined radius from a point at which a second object among the plurality of activated objects is displayed, and the display may move and display the first object according to the touch and drag input with respect to the first area, and may move and display the second object according to the touch and drag input with respect to the second area.

The user input unit may receive a touch and drag input with respect to an area in which the first area and the second area overlap with each other, and the controller may control the display to move and to display at least one of the first object and the second object, based on priority order information.

The controller may compare movement time information of the first object with movement time information of the second object, and may move and display one of the first object and the second object according to a result of the comparison.

The user input unit may receive multiple touch inputs with respect to the first object and the second object included in the plurality of activated objects, and the display may move and display the first object and the second object, respectively, according to the multiple touch inputs.

According to an aspect of an exemplary embodiment, there is provided a method of providing an ultrasound image, the method including dividing a touch screen into a first area and a second area, to be separate from and non-overlapping with the first area and of a smaller size than that of the first area; displaying the ultrasound image on the first area of a touch screen; receiving a touch input at a touch position, from the first area; extracting a partial image including a smaller portion of the ultrasound image containing the touch position, from the ultrasound image; and displaying a copy image of the partial image on the second area, while contemporaneously displaying an entire ultrasound image on the first area.

The touch position may correspond to an object of the ultrasound image displayed on the first area and the operation of extracting may include operations of obtaining positional information of the touch position on the first area; extracting the smaller portion of the ultrasound image having a preset size and surrounding the touch position; and displaying the object in a center of the copy image on the second area.

The touch position may correspond to a first object of the ultrasound image displayed on the first area and the operation of displaying may include displaying other objects of the ultrasound image on the first area, the first object and all or some of the other objects may be activated to be movable according to the touch input.

The displaying of the copy image may include magnifying the copy image of the partial image, on the second area.

According to an aspect of an exemplary embodiment, there is provided a method of displaying an object, the method including displaying, on an ultrasound image, a touch recognition region of an object used as a measurement mark; moving the object and the touch recognition region, in response to an input for touching and dragging the touch recognition region; detecting, from a portion of the ultrasound image which corresponds to the touch recognition region, a line formed by connecting points at which brightness variation of a pixel is greater than a threshold value; and moving the object to a position of the detected line by using coordinates of the detected line.

According to an aspect of an exemplary embodiment, there is provided an ultrasound apparatus including a touch screen configured to display, on an ultrasound image, a touch recognition region of an object used as a measurement mark; and a controller configured to move the object and the touch recognition region, in response to an input for touching and dragging the touch recognition region, to detect, from a portion of the ultrasound image which corresponds to the touch recognition region, a line formed by connecting points at which brightness variation of a pixel is greater than a threshold value, and to move the object to a position of the detected line by using coordinates of the detected line.

According to an aspect of an exemplary embodiment, there is provided a method of displaying an object, the method including displaying, on an ultrasound image, a plurality of touch recognition regions corresponding to a plurality of objects that are used as measurement marks; receiving an input for selecting a first touch recognition region among the plurality of touch recognition regions; and in response to the received input, changing visual representation of at least one of the first touch recognition region and a first object displayed in the first touch recognition region.

According to an aspect of an exemplary embodiment, there is provided an ultrasound apparatus including a touch screen configured to display, on an ultrasound image, a plurality of touch recognition regions corresponding to a plurality of objects that are used as measurement marks, and to receive an input for selecting a first touch recognition region among the plurality of touch recognition regions; and a controller configured to change, in response to the received input, visual representation of at least one of the first touch recognition region and a first object displayed in the first touch recognition region.

BRIEF DESCRIPTION OF THE DRAWINGS

The above and/or other aspects will become more apparent by describing certain exemplary embodiments, with reference to the accompanying drawings, in which:

FIG. 4 is a flowchart illustrating a method of providing a copy image, according to an exemplary embodiment;

FIGS. 5A and 5B illustrate a display of the ultrasound apparatus, according to an exemplary embodiment;

FIGS. 6A, 6B, and 6C illustrate screens for providing a copy image of a reference point at which the ultrasound apparatus selects a measurement area, according to an exemplary embodiment;

FIG. 7 is a flowchart of a method of displaying an object, according to an exemplary embodiment;

FIGS. 13A, 13B and 13C illustrate screens for providing a copy image related to generation of a body marker, according to an exemplary embodiment;

FIGS. 19A and 19B illustrate cases in which touch recognition ranges of objects overlap with each other, according to an exemplary embodiment;

FIG. 36 is a diagram illustrating an operation of adjusting a size of a touch recognition region, according to an exemplary embodiment.

DETAILED DESCRIPTION

Figure 1:
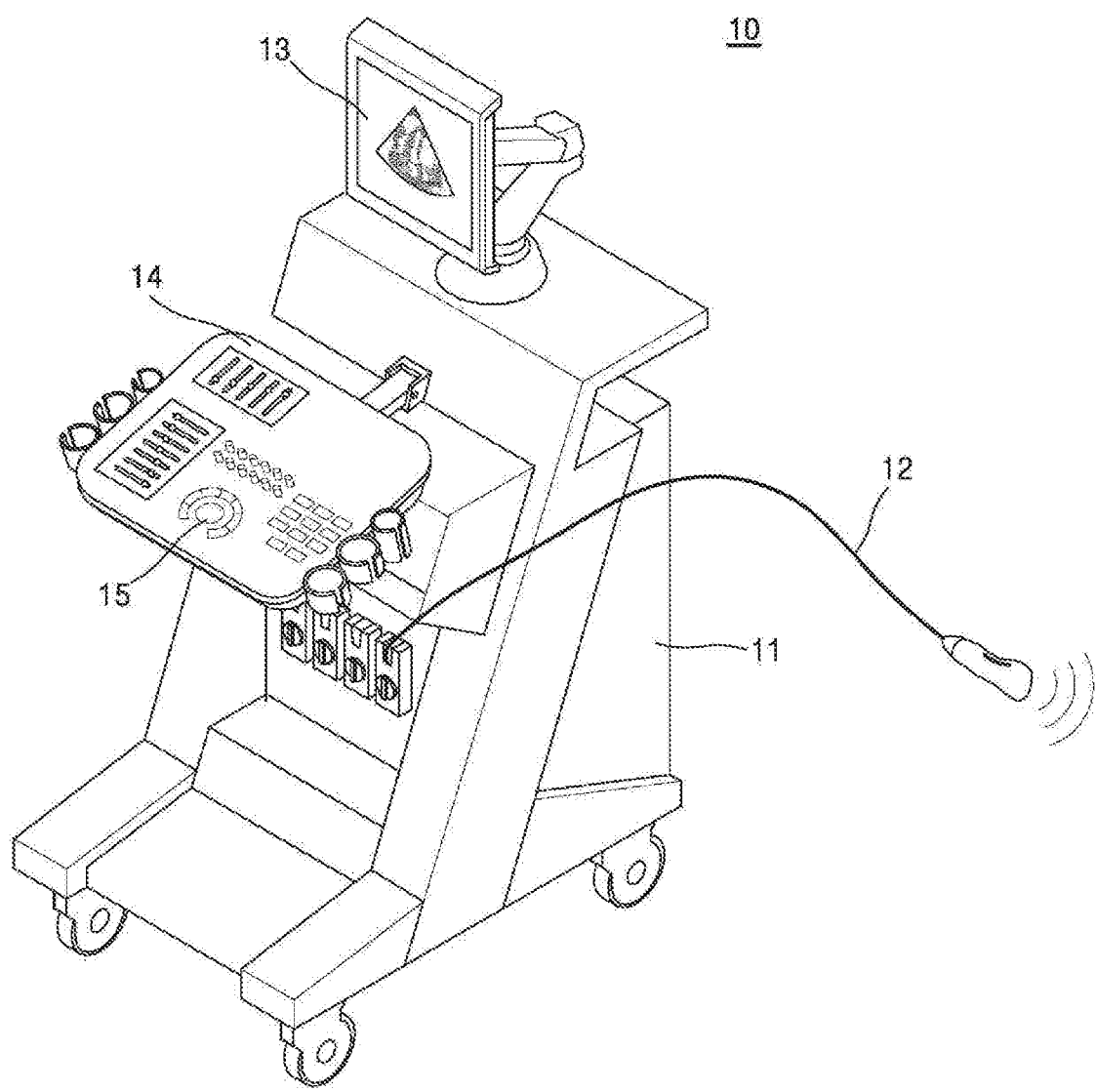
FIG. 1 illustrates a related art ultrasound apparatus.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described with reference to exemplary embodiments. Thus, the terms used herein have to be defined based on the meaning of the terms together with the description throughout the specification.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or embodied by combining hardware and software.

Throughout the specification, "ultrasound image" indicates an image of a target object which is obtained by using an ultrasound signal. The target object may be a part of a human body. For example, the target object may include organs such as the liver, the heart, the nuchal translucency (NT), the brain, the breast, the abdominal region, or the like, or a fetus.

The ultrasound image may vary in different forms. For example, the ultrasound image may be, but is not limited to, at least one of an image obtained during a brightness mode (hereinafter, referred to as "B mode image") indicating brightness as magnitude of an ultrasound echo signal that is reflected from the target, an image obtained during a color mode (hereinafter, referred to as "C mode image") indicating a color as speed of a moving target by using a Doppler effect, an image obtained during a Doppler mode (hereinafter, referred to as "D mode image") indicating a spectrum image of a moving target by using a Doppler effect, an image obtained during a motion mode (hereinafter, referred to as "M mode image") indicating motion of a target at a predetermined position according to time, and an image obtained during an elasticity mode (hereinafter, referred to as "elasticity mode image) indicating a difference between a reaction when compression is applied to a target and a reaction when compression is not applied to the target. Also, in one or more exemplary embodiments, the ultrasound image may be a two-dimensional (2D) image, a three-dimensional (3D) image, or a four-dimensional (4D) image.

Throughout the specification, a "user" may be a medical expert including a doctor, a nurse, a medical laboratory technologist, a sonographer, or the like.

Throughout the specification, the expression "an object is activated" means that the object may be movable according to a user's touch input.

Expressions such as "at least one of," when preceding a list of elements, modify the entire list of elements and do not modify the individual elements of the list.

FIG. 1 illustrates a related art ultrasound apparatus 10.

As illustrated in FIG. 1, the related art ultrasound apparatus 10 includes a main body 11, at least one probe 12, a display 13, and a control panel 14. Since the related art ultrasound apparatus 10 has a large size, it is difficult for a user to freely move the related art ultrasound apparatus 10 to different places. Also, due to its large size, the related art ultrasound apparatus 10 occupies a large space.

The display 13 and the control panel 14 of the related art ultrasound apparatus 10 are separated. Thus, when the user selects or measures a predetermined area of an ultrasound image or adjusts a gain of the ultrasound image that is obtained by using the at least one probe 12, the user has to check the ultrasound image and operate the control panel 14 in turn, such that a view of the user may be distracted.

Also, the user of the related art ultrasound apparatus 10 may move an object displayed on the display 13, by using a track ball 15 included in the control panel 14. Here, when the user attempts to move another object, the user has to additionally map the track ball 15 with the other object, such that it is difficult for the user to rapidly change a measurement point or a measurement line. This is described below with reference to FIGS. 2A and 2B.

Figure 2A:
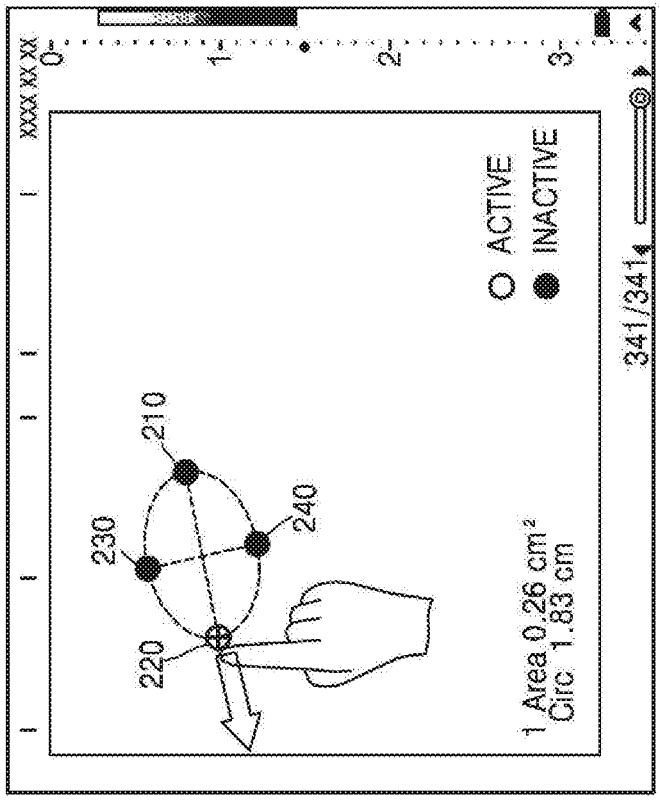
FIGS. 2A and 2B illustrate objects provided by the related art ultrasound apparatus.
Figure 2B:
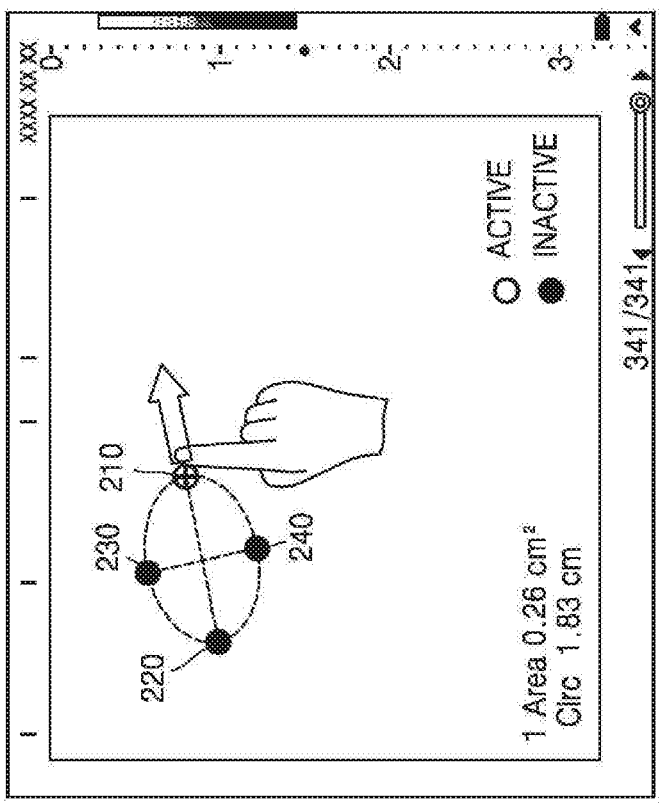

FIGS. 2A and 2B illustrate objects provided by the related art ultrasound apparatus 10.

As illustrated in FIG. 2A, the related art ultrasound apparatus 10 may activate motion with respect to only one object. That is, when a first object 210 is activated, a user may move only the first object 210 by using a track ball, a mouse, or a touch instrument (e.g., a finger or an electronic pen), and cannot move a second object 220, a third object 230, and a fourth object 240.

Thus, as illustrated in FIG. 2B, when the user attempts to move the second object 220, the related art ultrasound apparatus 10 has to change an activated position from the first object 210 to the second object 220. That is, the related art ultrasound apparatus 10 has to inactivate the activated first object 210 and to activate the second object 220 into an activated state. Thus, it is difficult for the user to rapidly move each of a plurality of objects.

Also, as illustrated in FIGS. 2A and 2B, when the user touches an object by using the touch instrument (e.g., the finger or the electronic pen), the object is obstructed by the touch instrument. Thus, it is difficult for the user to exactly move the object to a target position.

Figure 3:
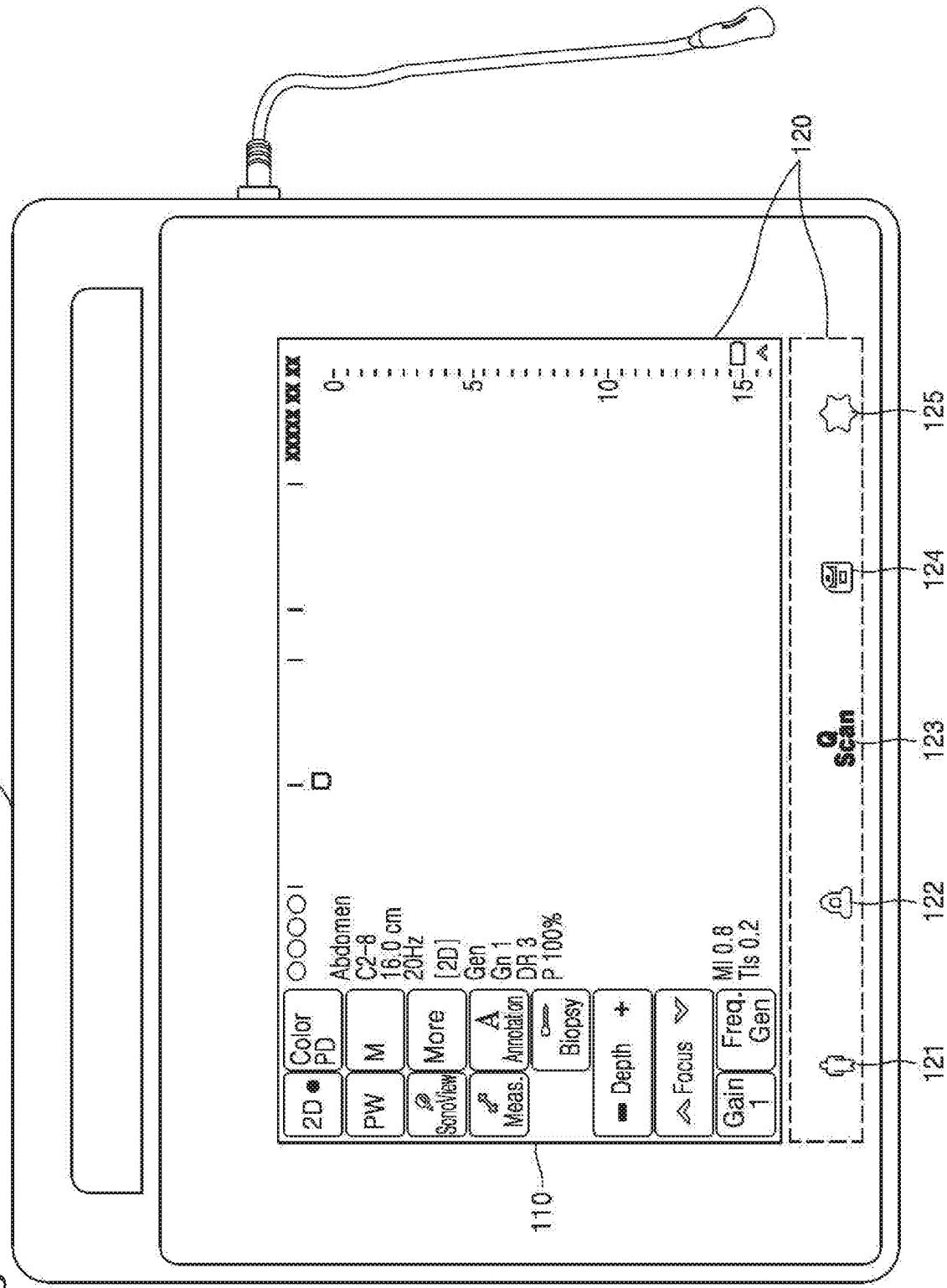
FIG. 3 illustrates an ultrasound apparatus according to an exemplary embodiment.

FIG. 3 illustrates an ultrasound apparatus 100 according to an exemplary embodiment.

As illustrated in FIG. 3, the ultrasound apparatus 100 may include a display 110, a user input unit 120, e.g., a user input receiver, and an interface to connect a probe.

In the present exemplary embodiment, the display 110 and a touchpad may form a mutual layer structure and thus may be formed as a touch screen. In the present exemplary embodiment, the display 110 may be used as both an output device and an input device.

The touch screen may receive a touch input position and a touched area and may also receive a touch input pressure. The touch screen may receive an actual touch and/or may receive a proximate touch.

In an exemplary embodiment, the term "actual touch" indicates a case in which a pointer actually touches a screen, and the term "proximate touch" indicates a case in which a pointer does not actually touch a screen but approaches the screen within a predetermined distance. In an exemplary embodiment, the pointer indicates an instrument that is used to touch or to proximately touch a specific portion of a displayed screen. Examples of the pointer include an electronic pen, a finger, and the like.

Although not illustrated, in order to recognize an actual touch or a proximate touch on the touch screen, the ultrasound apparatus 100 may internally or externally have various sensors in the touch screen. An example of the sensor to receive the touch on the touch screen may include a tactile sensor.

The tactile sensor detects a contact of a specific object at least as much as a person can detect. The tactile sensor may detect various types of information such as roughness of a contact surface, hardness of the contact object, temperature of a contact point, or the like.

Another example of the sensor for detecting the touch on the touch screen may include a proximity sensor. The proximity sensor detects existence of an object that approaches a predetermined detection surface or that exists nearby, by using a force of an electro-magnetic field or an infrared ray, without using a mechanical contact.

Examples of the proximity sensor include a transmission-type photoelectric sensor, a direction reflection-type photoelectric sensor, a mirror reflection-type photoelectric sensor, a high frequency oscillation-type proximity sensor, a capacity-type proximity sensor, a magnetic proximity sensor, an infrared-type proximity sensor, or the like.

The display 110 may include, but is not limited thereto, at least one of a liquid crystal display (LCD), a thin film transistor-liquid crystal display (TFT-LCD), an organic light-emitting display device, a flexible display, and a 3D display.

In the present exemplary embodiment, the display 110 may provide a copy image corresponding to a touch input portion by a user, so that the display 110 may allow the user to select an exact portion of the ultrasound image. This will be described in detail with reference to FIG. 4.

The display 110 may display a plurality of activated objects. This will be described in detail with reference to FIG. 7.

The user input unit 120 is a means by which the user inputs data to control the ultrasound apparatus 100. The user input unit 120 may include a touchpad (a touch capacitive type touchpad, a pressure resistive type touchpad, an infrared beam sensing type touchpad, a surface acoustic wave type touchpad, an integral strain gauge type touchpad, a Piezo effect type touchpad, or the like), a key pad, or the like. In particular, as described above, the touchpad and the display 110 may form the mutual layer structure and thus may be formed as the touch screen.

In the present exemplary embodiment, the ultrasound apparatus 100 may display an ultrasound image during a predetermined mode and a control panel about the ultrasound image on the touch screen. Then, the ultrasound apparatus 100 may detect a touch gesture by the user to the ultrasound image via the touch screen.

Throughout the specification, the touch gesture (i.e., the touch input) by the user may include a tap gesture, a touch and hold gesture, a double tap gesture, a drag gesture, a panning gesture, a flick gesture, a drag and drop gesture, a swipe gesture, a pinch gesture, or the like.

The "tap gesture" indicates a case in which the user touches the touch screen by using a finger or an electronic pen and then instantly takes away the finger or the electronic pen from the touch screen without moving the finger or the electronic pen on the touch screen.

The "touch and hold gesture" indicates a case in which the user touches the touch screen by using a finger or an electronic pen and maintains a touch input for at least a threshold time (e.g., 2 seconds). That is, a time interval between a touch-in time and a touch-out time is equal to or greater than the threshold time (e.g., 2 seconds). In order to allow the user to recognize whether a touch input is the tap gesture or the touch and hold gesture, if the touch input is maintained for at least a threshold time, a feedback signal may be provided in a visual, acoustic, or tactile manner. The threshold time may vary in one or more exemplary embodiments.

The "double tap gesture" indicates a case in which the user touches the touch screen twice by using a finger or an electronic pen.

The "drag gesture" indicates a case in which the user touches the touch screen by using a finger or an electronic pen and then moves the finger or the electronic pen to another position on the touch screen while the user maintains the touch. Due to the drag gesture, an object is moved or the panning gesture to be described below is performed.

The "panning gesture" indicates a case in which the user performs the drag gesture without selecting an object. The panning gesture does not select a particular object, so that an object is not moved within a page but a page itself may be moved within a screen or an object group is moved within the page.

The "flick gesture" indicates a case in which the user performs a drag gesture by using a finger or an electronic pen at a speed equal to or greater than a threshold speed (e.g., 100 pixels/second). Based on whether a movement speed of the finger or the electronic pen is equal to or greater than the threshold speed (e.g., 100 pixels/second), the drag gesture (or the panning gesture) and the flick gesture may be distinguished.

The "drag and drop gesture" indicates a case in which the user drags an object to a predetermined position in a screen, by using a finger or an electronic pen, and then takes away the finger or the electronic pen from the touch screen.

The "pinch gesture" indicates a case in which the user touches the touch screen by using two fingers and then moves the two fingers in different directions. The pinch gesture is for a pinch open or a pinch close with respect to an object or a page, and a value of the pinch open or a value of the pinch close is determined according to a distance between the two fingers.

The "swipe gesture" indicates a case in which the user touches an object in a screen by using a finger or an electronic pen, and horizontally or vertically moves the object by a predetermined distance. A movement in a diagonal direction is not detected as the swipe gesture.

The ultrasound apparatus 100 may physically include some buttons that are frequently used by the user and that are included in the control panel of the related art ultrasound apparatus, and may provide the rest of the buttons as a graphical user interface (GUI) via the touch screen.

For example, the user input unit 120 may physically include, but is not limited thereto, a patient button 121, a probe button 122, a scan button 123, a storage button 124, an ultrasound image selection button 125, or the like.

The patient button 121 involves selecting a patient who undergoes an ultrasound diagnosis. The probe button 122 involves selecting a probe to be used in the ultrasound diagnosis. The scan button 123 involves quickly compensating for an ultrasound image by using a parameter value that is preset in the ultrasound apparatus 100. The storage button 124 involves storing an ultrasound image. The ultrasound image selection button 125 involves pausing ultrasound images that are displayed in real-time and then allowing one paused ultrasound image to be displayed on a screen.

The user input unit 120 may include, but is not limited thereto, a 2D button, a color button, a PW button, an M button, a SonoView button (i.e., a button for checking pre-stored images), a More button, a Meas. button (i.e., a measure button), an Annotation button, a Biopsy button (i.e., a button for guiding an insertion position for a needle), a Depth button, a Focus button, a Gain button, a Freq. button (i.e., frequency button), or the like as the GUI. A function of each of the aforementioned buttons may be easily derived by one of ordinary skill in the ultrasound art in view of names of the buttons, thus, detailed descriptions for the buttons are omitted here.

Hereinafter, a method of providing a copy image is described in detail with reference to FIG. 4, wherein the ultrasound apparatus 100 having a touch screen performs the method to help a user to perform an exact touch input on an ultrasound image that is displayed via the touch screen.

FIG. 4 is a flowchart illustrating a method of providing a copy image, performed by the ultrasound apparatus 100, according to an exemplary embodiment.

In operation S410, the ultrasound apparatus 100 may display an ultrasound image on a first area of a touch screen. According to the present exemplary embodiment, the ultrasound image may be, but is not limited to, one of a B mode image, a Doppler image, an M mode image, and a C mode image.

The ultrasound apparatus 100 may display a plurality of ultrasound images on the first area of the touch screen. For example, the ultrasound apparatus 100 may display the B mode image and the Doppler image on the first area or may display the B mode image and the M mode image on the first area.

The ultrasound apparatus 100 may display a predetermined object on the ultrasound image, based on user setting. For example, the ultrasound apparatus 100 may display a reference line or a reference point with respect to selection of a region of interest (ROI), a body marker, or a sample volume on the ultrasound image.

According to the present exemplary embodiment, the body marker may be a figure that represents a position or a target, which is scanned by ultrasound. The body marker may include a figure indicating an ultrasound-scanned target, and a figure corresponding to a position of a probe that contacts the target. Examples of the body marker may include an arm figure, a liver figure, a womb figure, or the like.

According to the present exemplary embodiment, the sample volume indicates a limited zone in which a Doppler signal is input due to an operation of a range gate.

The ultrasound apparatus 100 may adjust a size of the sample volume by varying a size of the range gate. When the size of the range gate is increased, the sample volume involving the obtaining of the Doppler signal is also increased. According to the present exemplary embodiment, the user may obtain a Doppler image at a specific position, by moving a position of the sample volume.

In operation S420, the ultrasound apparatus 100 may detect a touch input to the ultrasound image. According to the present exemplary embodiment, the ultrasound apparatus 100 may obtain information about a position of the touch screen at which the touch input is detected. The information about the position at which the touch input is detected may include a coordinate value (e.g., a pixel value) of the position of the touch screen at which the touch input is detected.

The touch input may include a touch and hold gesture, a drag gesture, a swipe gesture, or the like. The ultrasound apparatus 100 may detect multiple touch inputs with respect to at least two portions of the ultrasound image. For example, the ultrasound apparatus 100 may detect a pinch gesture by the user.

In operation S430, the ultrasound apparatus 100 may extract a partial image of the ultrasound image that corresponds to the touch input. For example, the partial image may have a predetermined size, and the ultrasound apparatus 100 may extract the partial image based on the position of the touch screen at which the touch input is detected. The predetermined size may vary according to a system environment or user setting.

The ultrasound apparatus 100 may capture the partial image corresponding to the touch input and then may generate a copy image of the partial image.

The ultrasound apparatus 100 may extract a partial image corresponding to a touch input at regular intervals. The ultrasound apparatus 100 may extract a partial image when the position at which the touch input is detected is changed.

In operation S440, the ultrasound apparatus 100 may display the copy image of the partial image on a second area that is different from the first area on which the ultrasound image is displayed. That is, according to the present exemplary embodiment, the ultrasound apparatus 100 may display the copy image on an area on which the ultrasound image is not displayed.

The ultrasound apparatus 100 may display the copy image on the second area, which is also different from a third area on which a control panel with respect to a control of parameter values related to the ultrasound image is displayed as a GUI. That is, the ultrasound apparatus 100 may display the copy image on an area other than the first area that displays the ultrasound image and the third area that displays the control panel as the GUI.

The ultrasound apparatus 100 may display the copy image obtained by capturing the partial image having the predetermined size, on the second area. According to the present exemplary embodiment, the ultrasound apparatus 100 may display the copy image so that an object that is displayed at the position at which the touch input is detected may be located at a center of the second area. The object may include, but is not limited to, at least one of the reference point or the reference line with respect to selection of a measurement portion or a measurement area, the sample volume, and the body marker.

The ultrasound apparatus 100 may synchronize in real-time a partial image and a copy image that corresponds to the partial image, wherein the partial image is changed according to drag inputs, and may display the copy image on the second area. The user may watch the copy image displayed on the second area, thereby recognizing in real-time a portion of the ultrasound image which is obstructed by a touch instrument (e.g., a finger or an electronic pen).

The ultrasound apparatus 100 may display a copy image on the second area, wherein the copy image is obtained by magnifying or reducing the partial image by a predetermined ratio, and the partial image is extracted with respect to the position at which the touch input is detected. The predetermined ratio may vary according to a system environment or user setting.

According to the present exemplary embodiment, when the ultrasound apparatus 100 no longer detects the touch input, the ultrasound apparatus 100 may remove the copy image from the second area. That is, when the user no longer touches the touch screen with the finger or the electronic pen, the copy image may disappear from the touch screen.

Hereinafter, with reference to FIGS. 5A and 5B, the first area, the second area, and the third area that are displayed on the touch screen are described below.

Figure 5B:
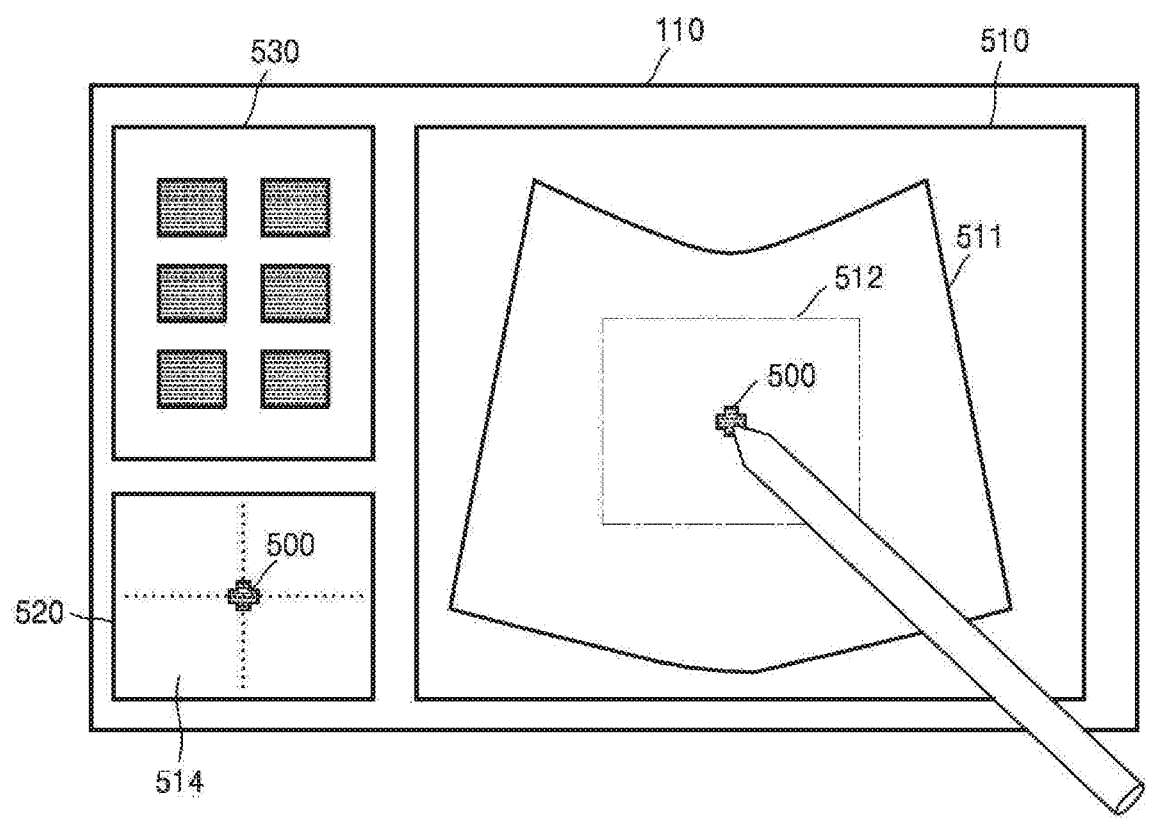

FIGS. 5A and 5B illustrate the display 110 of the ultrasound apparatus 100, according to an exemplary embodiment.

As illustrated in FIG. 5A, the display 110 of the ultrasound apparatus 100 may divide a touch screen into a first area 510, a second area 520, and a third area 530, but the division is not limited thereto.

The first area 510 may be a preset area of the touch screen on which an ultrasound image 511 is displayed. The second area 520 may be an area on which a copy image of a partial image corresponding to a touch input is displayed. The third area 530 may be an area on which a control panel while in a predetermined mode (e.g., a B mode, a Doppler mode, an M mode, or the like) is displayed as a GUI.

A position or a size of each of the first, second, and third areas 510, 520, and 530 may vary according to a system or user setting. In particular, the ultrasound apparatus 100 may select the second area 520 in areas that do not overlap with the first area 510 and the third area 530. That is, a position of the control panel and a position of an area that displays an ultrasound image may be changed according to modes; thus, the ultrasound apparatus 100 may adaptively select the second area 520 on which the copy image is displayed.

In the present exemplary embodiment, when a user touches a specific portion of the ultrasound image 511 by using a finger, the ultrasound apparatus 100 may detect a touch input by the user with respect to the ultrasound image 511 that is displayed on the first area 510. Here, since an object 500 that is displayed on the touched portion is obstructed by the finger, it is difficult for the user to recognize whether the user exactly touches a user-desired portion.

As illustrated in FIG. 5B, the user may touch a specific portion of the ultrasound image 511 by using an electronic pen (e.g., a stylus pen). Here, since an object 500 that is displayed on the touched portion is obstructed by the pen, it is difficult for the user to see whether a user-desired portion is in fact touched.

Thus, the ultrasound apparatus 100 may extract a partial image 512 corresponding to the touch input and may display a copy image 514 of the partial image 512, on the second area 520. For example, the ultrasound apparatus 100 may extract the partial image 512 having a size (e.g., 3 cm×3 cm) with respect to a position at which the touch input is detected. Then, the ultrasound apparatus 100 may display the copy image obtained by capturing the partial image 512, on the second area 520. The ultrasound apparatus 100 may display the copy image so that the object 500 that is displayed at the position at which the touch input is detected may be located at a center of the second area 520.

In this case, the user may exactly recognize at which point in the ultrasound image 511 the user-touched portion is positioned, by referring to the copy image. For example, when the user measures a size of a tumor or a girth of a fetus, the user may check the copy image, thereby selecting an exact measurement portion.

When the ultrasound apparatus 100 detects a drag input that starts at the position at which the touch input is detected, the ultrasound apparatus 100 may move the object 500, which is displayed at the position at which the touch input is detected, according to the drag input, and may display the copy image displayed on the second region 520 after changing the copy image in real-time.

In the present exemplary embodiment, the ultrasound apparatus 100 may display the copy image on the second area 520 adjacent to the first area 510 on which the ultrasound image 511 is displayed, so that a view of the user is not distracted.

Hereinafter, a method of providing a copy image during a predetermined mode, performed by the ultrasound apparatus 100, will be described in detail with reference to an exemplary embodiment of FIGS. 6A, 6B and 6C.

Figure 6A:
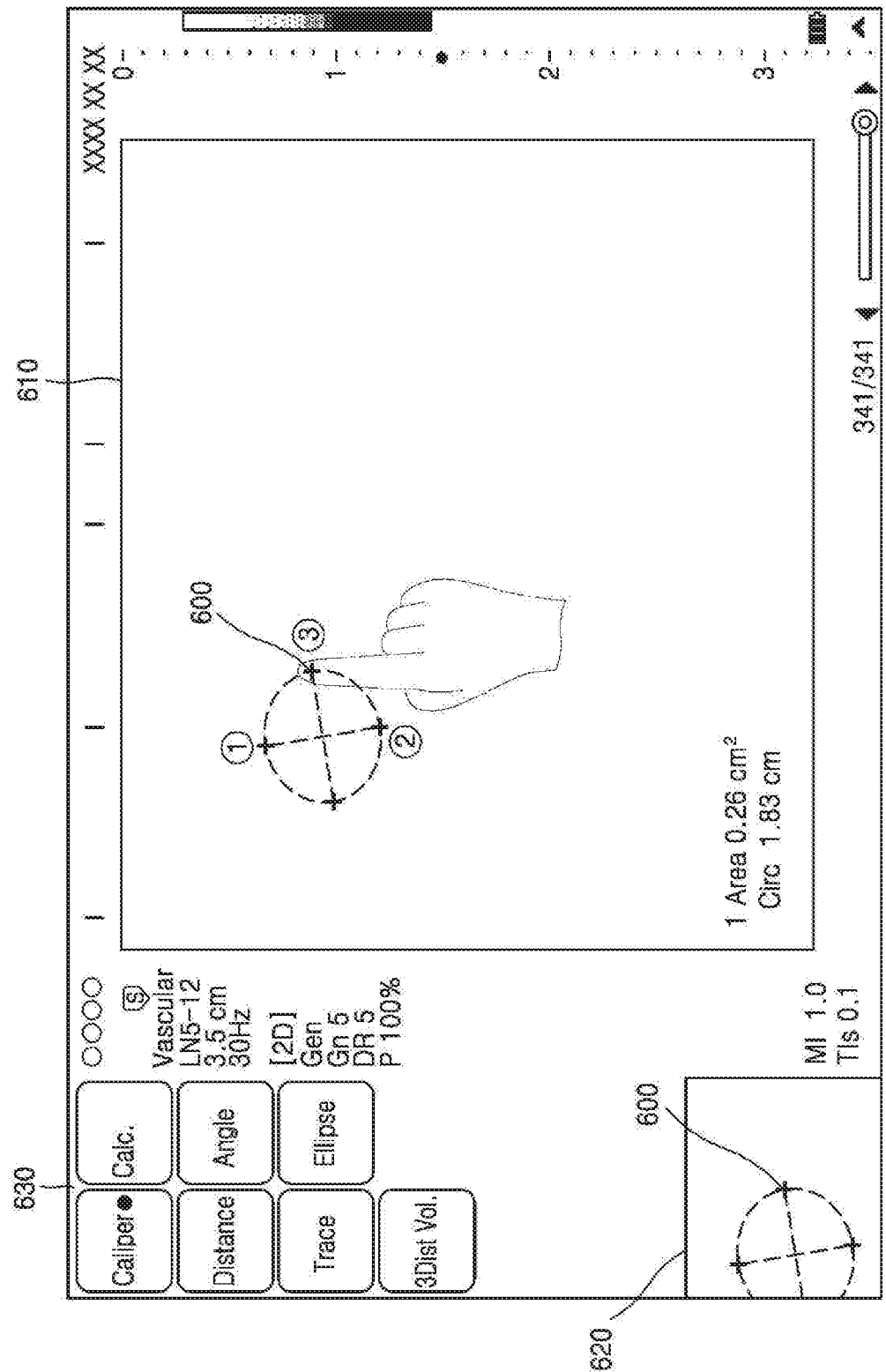
Figure 6C:
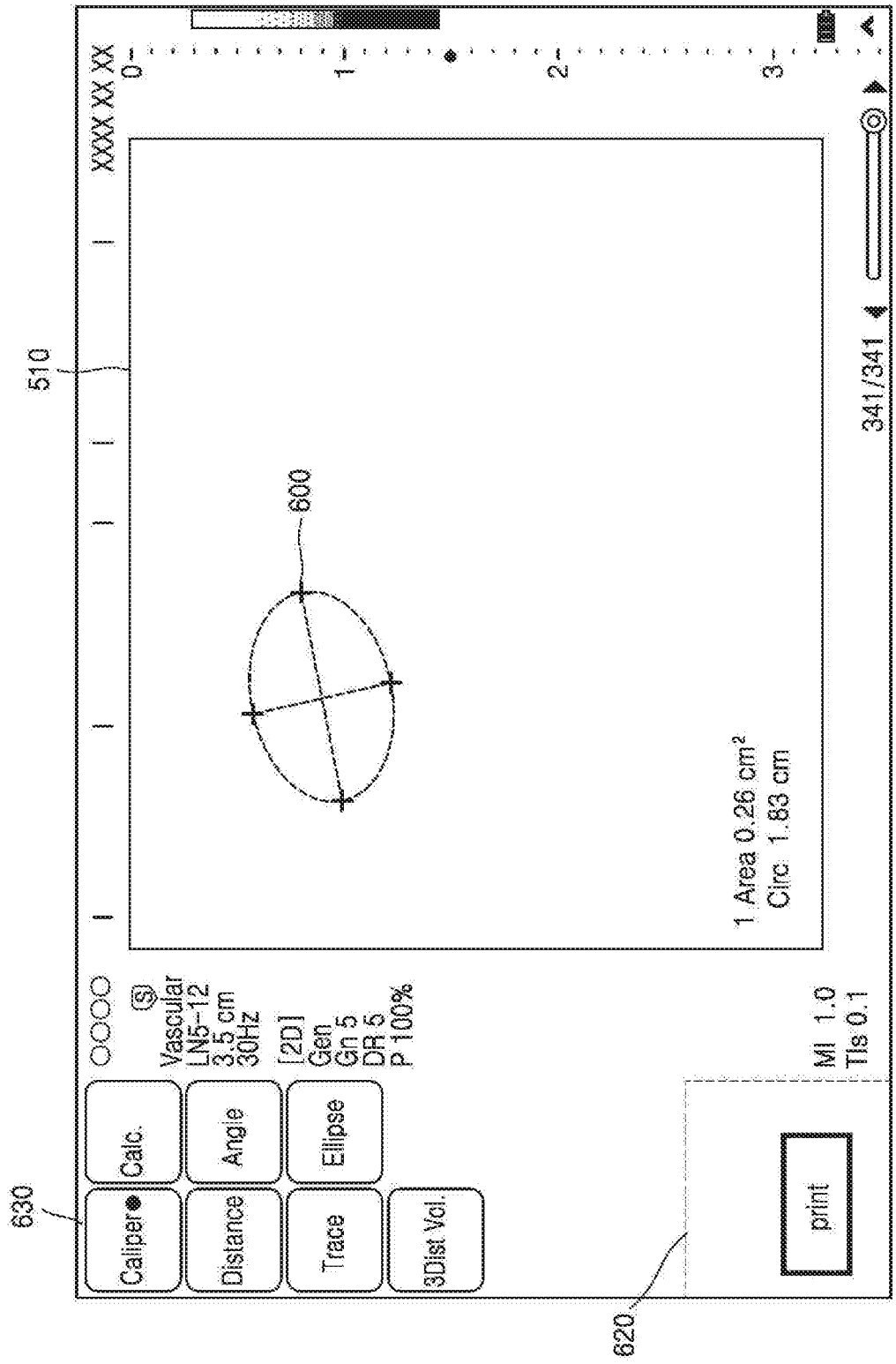

FIGS. 6A to 6C illustrate screens for providing a copy image of a reference point at which the ultrasound apparatus 100 selects a measurement area, according to an exemplary embodiment.

As illustrated in FIG. 6A, when a user selects a Caliper button and then selects an Ellipse button of a control panel that is displayed on a third area 630, touches and drags from a first portion ① of an ultrasound image to a second portion ② of the ultrasound image, and then takes off a finger, the ultrasound apparatus 100 may display an oval-shape object for selection of a measurement area on a first area 610. The user may leftward or rightward drag a cross-shape reference point 600 that is displayed on a third portion ③; thus, the user may adjust a size of the measurement area.

When the user touches the third portion ③, the ultrasound apparatus 100 may display a copy image having a predetermined size with respect to a user-touched portion, on a second area 620. The cross-shape reference point 600 that is displayed on the third portion ③ may be located at a center of the second area 620 and the copy image may be displayed without magnification or reduction as compared to a corresponding portion of the ultrasound image displayed on the first area 610 of FIG. 6A.

As illustrated in FIG. 6B, when the user touches and simultaneously rightward drags the cross-shape reference point 600 that is displayed on the third portion ③, a point at which a touch input is detected is continuously changed according to drag inputs, so that the ultrasound apparatus 100 may change a copy image in real-time with respect to the point at which the touch input is detected and may display the copy image on the second area 620. That is, the copy image having a predetermined size with respect to the cross-shape reference point 600 may be changed in real-time and may be displayed on the second area 620. The cross-shape reference point 600 may be located at a center of the second area 620 and the copy image may be displayed without magnification or reduction as compared to a corresponding portion of the ultrasound image displayed on the first area 610 of FIG. 6B.

The user may recognize an exact position of the cross-shape reference point 600, which is obstructed by a finger, in the first area 610 by referring to the copy image displayed on the second area 620. That is, the ultrasound apparatus 100 may help the user to exactly measure a size of a tumor or the like, which is very important in a disease diagnosis or the like.

As illustrated in FIG. 6C, when the user takes off the finger from the touch screen, the ultrasound apparatus 100 no longer displays the copy image on the second area 620.

In the present exemplary embodiment, the ultrasound apparatus 100 may help the user to exactly recognize a reference point, which is obstructed by a touch instrument (e.g., a finger or an electronic pen), by using the copy image.

Hereinafter, a method of displaying an object on a screen, the method performed by the ultrasound apparatus 100 to allow a user to touch, to drag and to freely move the object that is activated with respect to its motion, will now be described in detail with reference to FIGS. 7 through 9.

FIG. 7 is a flowchart of a method of displaying an object, the method performed by the ultrasound apparatus 100, according to an exemplary embodiment.

In operation S710, the ultrasound apparatus 100 may extract a plurality of objects that are movable during a predetermined mode.

The predetermined mode may include a measurement mode, an annotation input mode, a Doppler mode, an M mode, or the like. During the measurement mode, a circumference, a length, a size, or the like of an interest area may be measured, a maximum speed, an instantaneous speed, a slope, or the like in a predetermined sample volume may be measured, or speed variation according to time may be measured. Functions of the annotation input mode, the Doppler mode, and the M mode are known to one of ordinary skill in the art, thus, detailed descriptions thereof are omitted here.

The plurality of objects that are movable during the predetermined mode indicate objects that are movable according to a user's touch input, when the objects are activated. For example, each of the objects may include, but is not limited to, at least one of a reference point, a reference line, annotation, and an arrow which are used in selecting a measurement point or a measurement area.

The objects may be a same type of objects or different types of objects. The objects may include a first reference point and a second reference point. The objects may include a first reference point and a sample volume, or a first reference point and annotation.

In operation S720, the ultrasound apparatus 100 may activate the objects to allow each of the extracted objects to move according to a user's touch input. That is, in order to allow a user to freely move each of the extracted objects by performing a touch input, the ultrasound apparatus 100 may activate all of the objects.

In operation S730, the ultrasound apparatus 100 may display together the activated objects and an ultrasound image. In the present exemplary embodiment, the ultrasound image may include, but is not limited to, a B mode image, a Doppler image, an M mode image, and an elasticity mode image.

The ultrasound apparatus 100 may display the activated objects on the ultrasound image. In an exemplary embodiment, the ultrasound apparatus 100 may display the activated objects to partially overlap with the ultrasound image, or may display the activated objects in an area of a screen which is different from another area of the screen on which the ultrasound image is displayed.

In the present exemplary embodiment, the ultrasound apparatus 100 may receive a touch and drag input with respect to at least one object among the activated objects. In this case, the ultrasound apparatus 100 may move the at least one object according to the touch and drag input and may display the at least one object.

When sizes of objects related to the ultrasound image are small, it is difficult for the user to exactly select an object by performing a touch input. Also, although the user exactly touches the object by using a touch instrument, the object is obstructed by the touch instrument, such that it is difficult for the user to recognize an exact position of the object. Thus, in the present exemplary embodiment, the ultrasound apparatus 100 may expand a touch recognition range in which the object is recognized as being selected.

For example, when the ultrasound apparatus 100 receives a touch and drag input with respect to a first area within a predetermined radius from a point at which an activated first object is displayed, the ultrasound apparatus 100 may recognize that the ultrasound apparatus 100 has received the touch and drag input with respect to the first object. Also, when the ultrasound apparatus 100 receives a touch and drag input with respect to a second area within the predetermined radius from a point at which a second object among the activated objects is displayed, the ultrasound apparatus 100 may move the second object according to the touch and drag input with respect to the second area and may display the second object.

According to exemplary embodiments, a touch recognition range of the first object and a touch recognition range of the second object may overlap with each other. When the user touches and drags the overlapped area, the ultrasound apparatus 100 may move one of the first and second objects and then may display the moved object, according to priority order information. The priority order information is an information with respect to which an object among a plurality of objects is determined to be selected when the user performs a touch input on an area in which touch recognition ranges of the plurality of objects overlap with each other. For example, if the user touches the overlapped area, only one measurement mark will be moved to a new position, according to priority order information. That is, in order to move the overlapped objects, the objects are touched on the overlapped area or dragged on the overlapped area, wherein only one of the overlapped objects will be moved based on the priority order information.

For example, in a case where movement priority orders of the plurality of objects are preset, the ultrasound apparatus 100 may move one of the first and second objects according to the preset movement priority orders. For example, if the priority order is set so that a lastly-moved object has a lower priority, the ultrasound apparatus 100 may compare movement time information of the first object with movement time information of the second object, and may move one of the first and second objects, which has an earlier movement time, according to the comparison result. Exemplary embodiments in which a touch recognition range with respect to an object expands will be described in detail with reference to FIGS. 17 through 19.

Figure 8A:
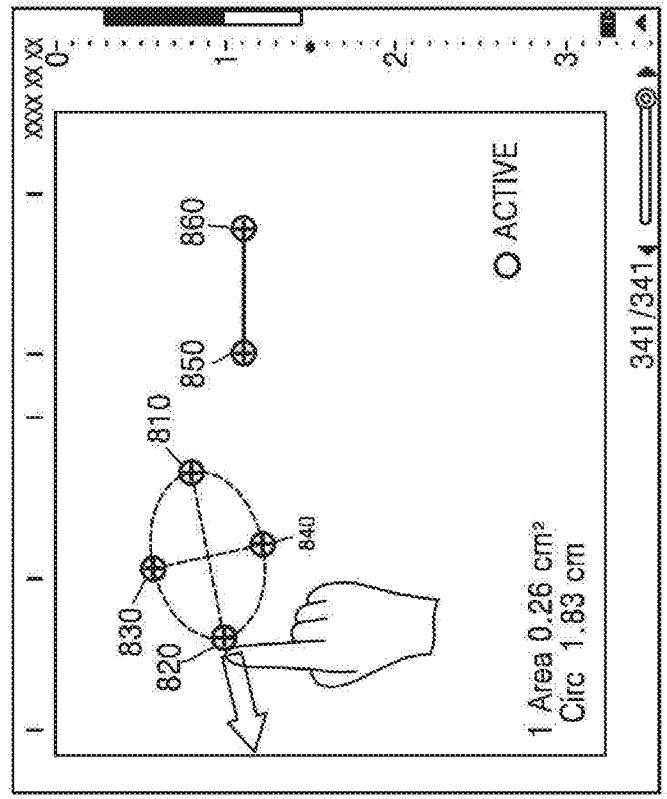
FIGS. 8A and 8B illustrate a plurality of activated objects, according to an exemplary embodiment.
Figure 8B:
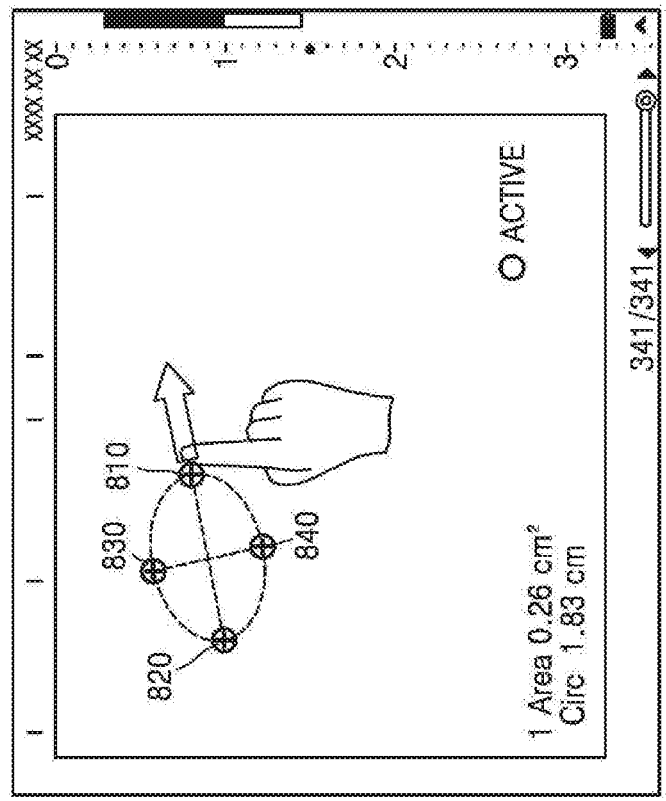

FIGS. 8A and 8B illustrate a plurality of activated objects, according to an exemplary embodiment.

As illustrated in FIG. 8A, when a measurement mode for measuring a size or a circumference of an interest area is selected, the ultrasound apparatus 100 may extract movable objects during the measurement mode.

For example, in a case where a user selects a caliper button and an Ellipse button of a control panel, touches and simultaneously drags a third reference point 830 of an ultrasound image to a fourth reference point 840, and then takes off a finger, the ultrasound apparatus 100 may display an oval enabled for selecting a measurement area on the ultrasound image. The ultrasound apparatus 100 may extract a first reference point 810, a second reference point 820, the third reference point 830, and the fourth reference point 840 as the movable objects during the measurement mode.

Afterward, the ultrasound apparatus 100 may activate all of the first reference point 810, the second reference point 820, the third reference point 830, and the fourth reference point 840. Thus, the user may move a position of the first reference point 810 by instantly touching and dragging the first reference point 810 in a right direction, without separate manipulation.

As illustrated in FIG. 8B, the user may move a position of the second reference point 820 by directly touching and dragging the second reference point 820 without separately inactivating the first reference point 810 and activating the second reference point 820.

When a length measurement line is added according to a user input, the ultrasound apparatus 100 may extract objects (e.g., a fifth reference point 850 and a six reference point 860) that are movable on the length measurement line, and may activate all of the extracted objects (e.g., the fifth reference point 850 and the sixth reference point 860).

Thus, the user may freely move a measurement reference point by touching the activated objects (i.e., the first through sixth objects 810 through 860). That is, according to the present exemplary embodiment, the ultrasound apparatus 100 may improve convenience of the user who uses a touch interface, and may allow rapid measurement and diagnosis.

Figure 9:
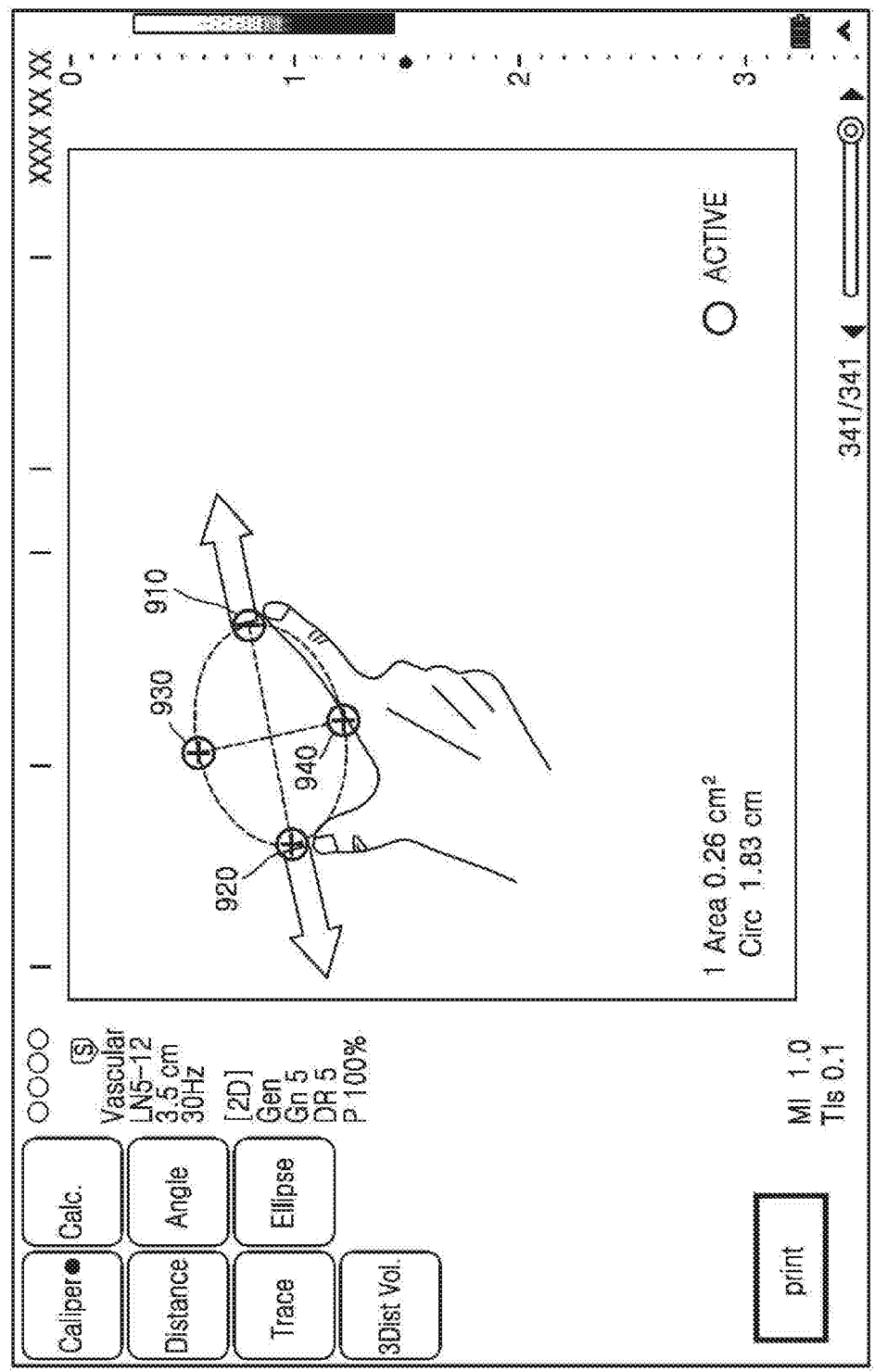
FIG. 9 illustrates an example in which a plurality of activated objects are moved according to multiple touch inputs.

FIG. 9 illustrates an example in which a plurality of activated objects are moved according to multiple touch inputs.

As illustrated in FIG. 9, the ultrasound apparatus 100 may receive the multiple touch inputs with respect to a first object and a second object included in the activated objects. The ultrasound apparatus 100 may move each of the first and second objects according to the multiple touch inputs and may display them.

For example, in a case where a user selects a caliper button and an Ellipse button of a control panel, touches and simultaneously drags a third reference point 930 of an ultrasound image to a fourth reference point 940, and then takes off a finger, the ultrasound apparatus 100 may display an oval enabled for selecting a measurement area on the ultrasound image. The ultrasound apparatus 100 may extract a first reference point 910, a second reference point 920, the third reference point 930, and the fourth reference point 940 as movable objects during a measurement mode.

Thus, the user may move two fingers in different directions while the user touches the first reference point 910 and the second reference point 920, with the two fingers. The ultrasound apparatus 100 may move each of the first reference point 910 and the second reference point 920, and thus therefore adjust a length of a long axis of the oval enabled for selecting the measurement area.

Figure 10A:
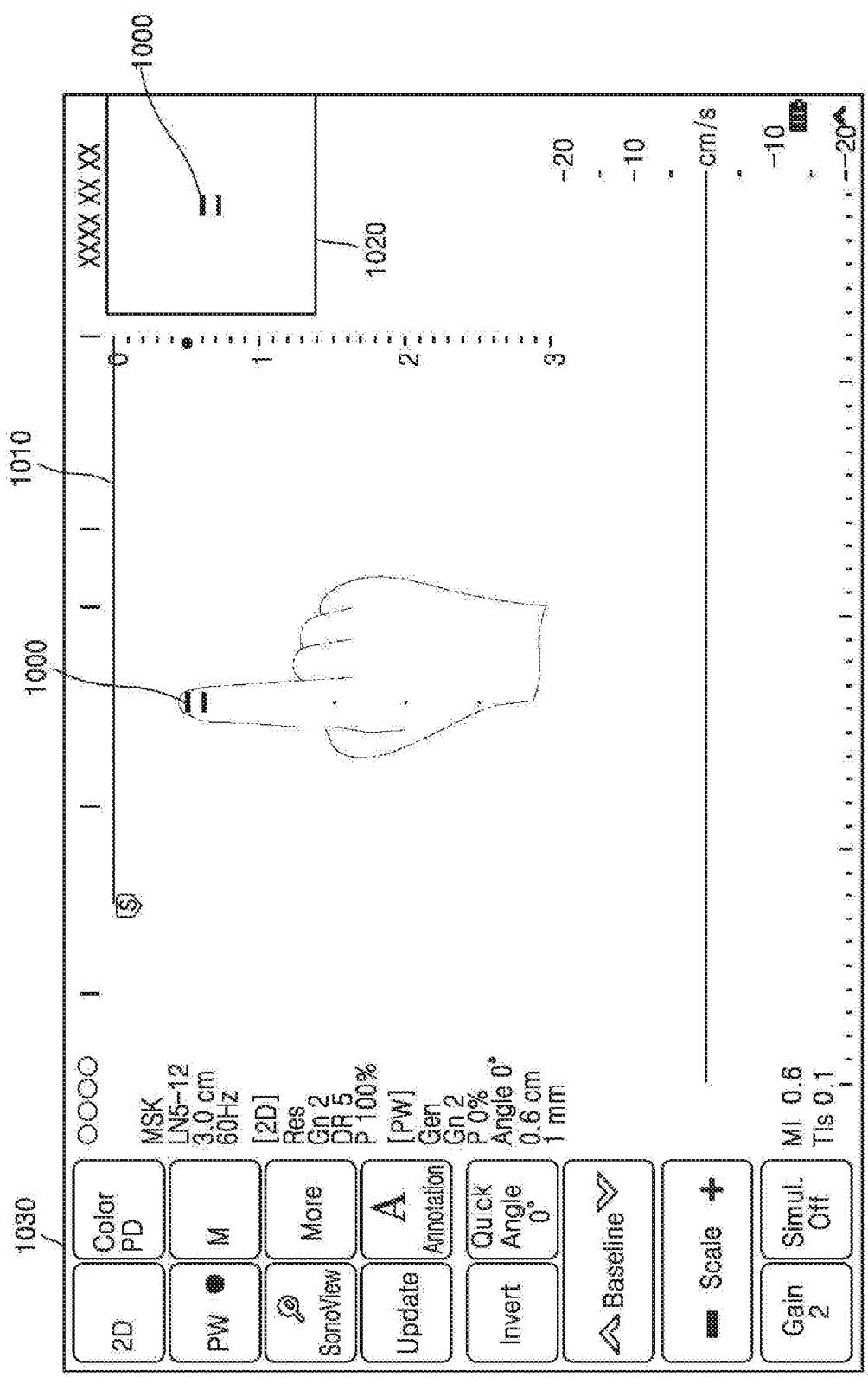
FIGS. 10A, 10B and 10C illustrate screens for providing a copy image related to a sample volume, according to an exemplary embodiment.
Figure 10B:
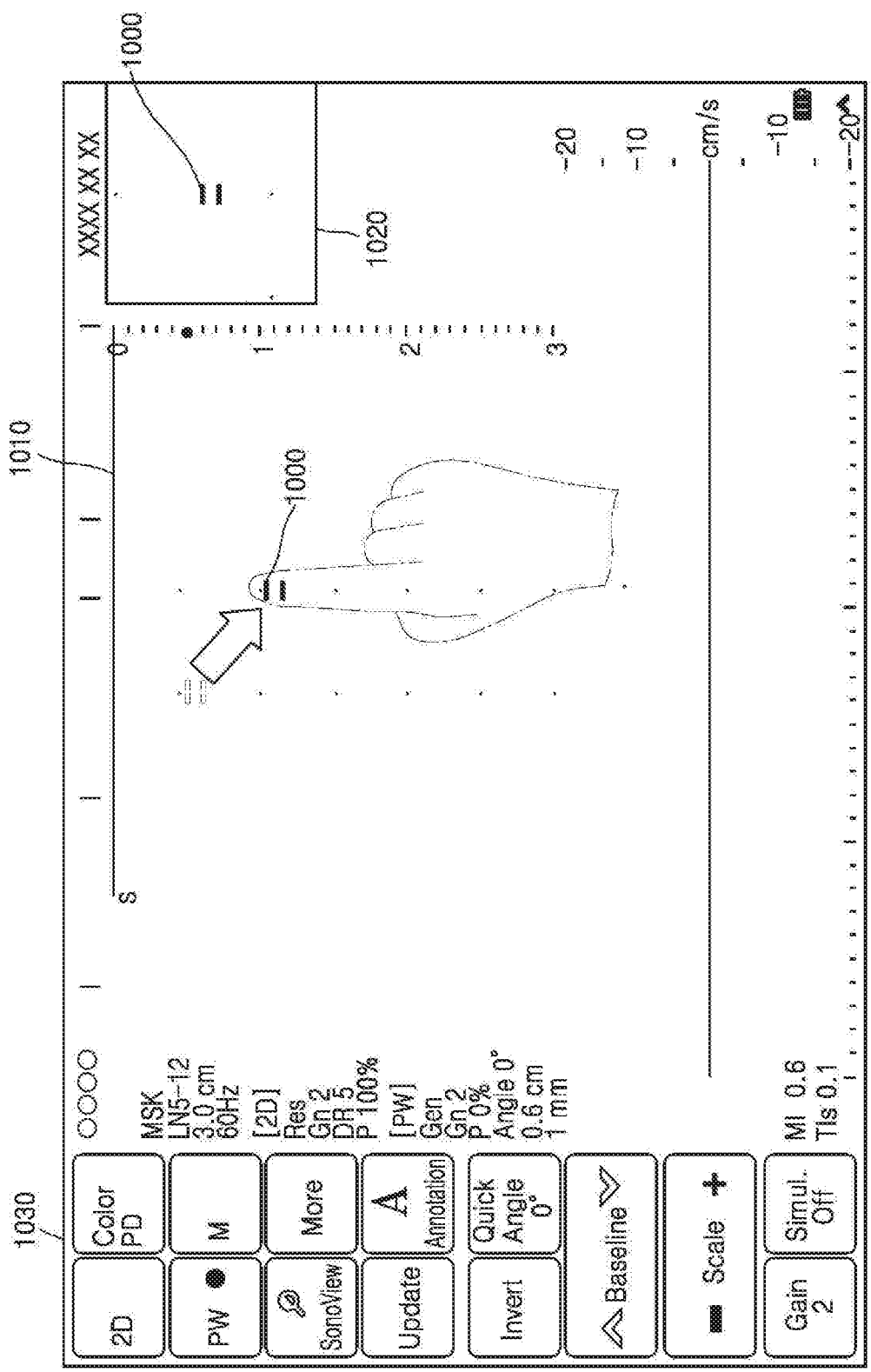

FIGS. 10A and 10B illustrate screens for providing a copy image related to a sample volume, performed by the ultrasound apparatus 100, according to an exemplary embodiment.

As illustrated in FIG. 10A, when a user selects a PW button of a control panel displayed on a third area 1030, the ultrasound apparatus 100 may detect user selection and then may display a sample volume 1000 on a B mode image. In this case, the user may touch and simultaneously move the sample volume 1000, thereby selecting a measurement position (e.g., a predetermined blood vessel) for observation of a Doppler image.

When the user touches the sample volume 1000, the sample volume 1000 and an ultrasound image around the sample volume 1000 are obstructed by a finger. Thus, the ultrasound apparatus 100 may display a copy image having a predetermined size with respect to a user-touched portion, on a second area 1020. The sample volume 1000 that is displayed on the user-touched portion may be located at a center of the second area 1020.

As illustrated in FIG. 10B, when the user touches and simultaneously drags the sample volume 1000, a point at which a touch input is detected is continuously changed according to drag inputs, so that the ultrasound apparatus 100 may change a copy image in real-time with respect to the point at which the touch input is detected and may display the copy image on the second area 1020. That is, the copy image having a predetermined size with respect to the sample volume 1000 may be changed in real-time and may be displayed on the second area 1020.

The user may recognize an exact position of the sample volume 1000, which is obstructed by a finger, in the first area 1010 by referring to the copy image displayed on the second area 1020.

Figure 10C:
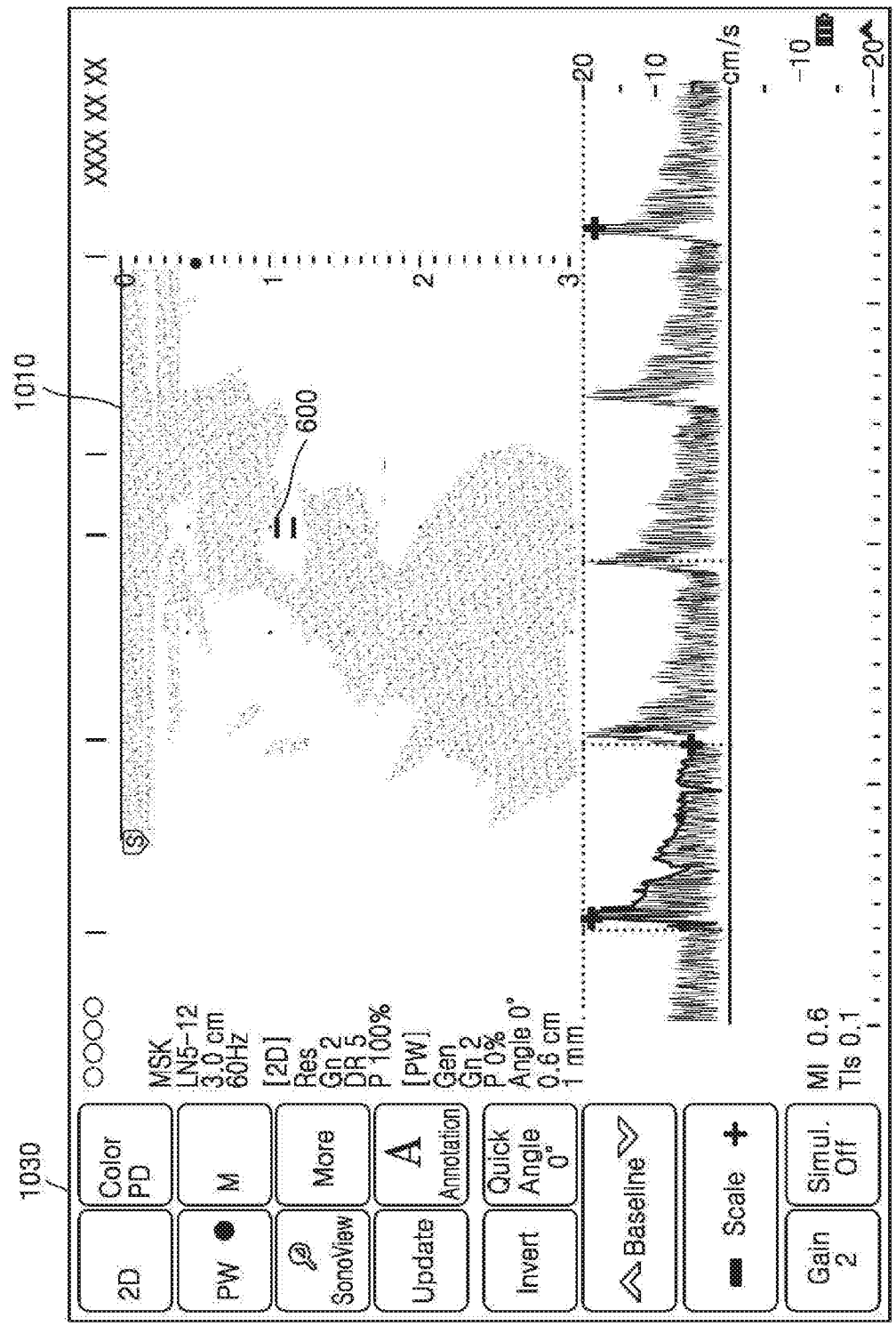

As illustrated in FIG. 10C, when the user moves the sample volume 1000 to a user-desired position and then takes off the finger from the touch screen, the ultrasound apparatus 100 no longer displays the copy image on the second area 1020. Then, the ultrasound apparatus 100 may provide the Doppler image about a blood vessel at which the sample volume 1000 is positioned.

In the present exemplary embodiment, the ultrasound apparatus 100 may allow the user to recognize a position of the sample volume 1000, which is obstructed by a touch instrument (e.g., a finger or an electronic pen), by using the copy image, so that the ultrasound apparatus 100 may help the user to exactly select a target blood vessel for a Doppler image.

Figure 11A:
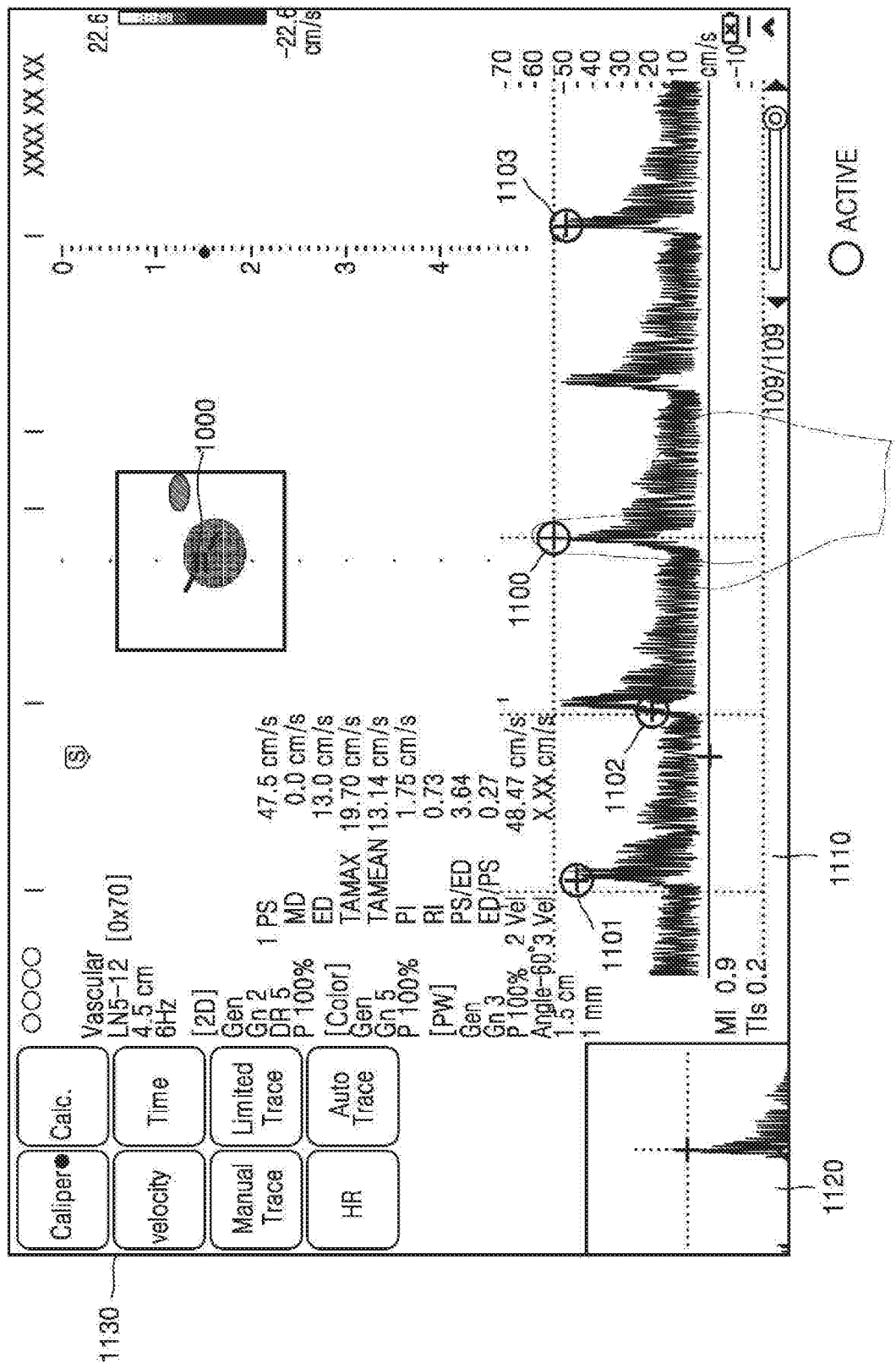
FIGS. 11A and 11B illustrate screens for providing a copy image and a plurality of activated objects related to a Doppler image, according to an exemplary embodiment.
Figure 11B:
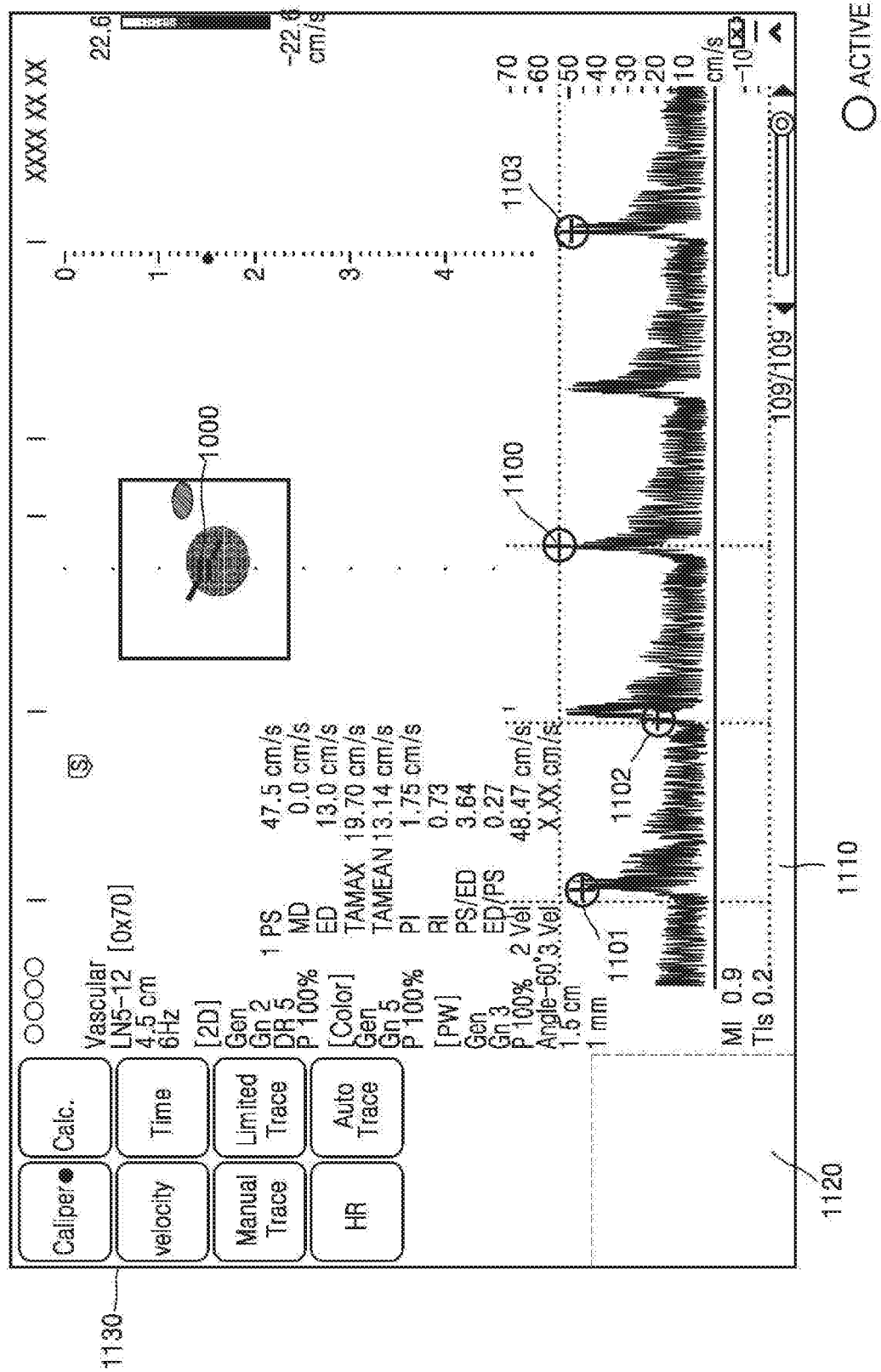

FIGS. 11A and 11B illustrate screens for providing a copy image and a plurality of activated objects related to a Doppler image, performed by the ultrasound apparatus 100, according to an exemplary embodiment.

As illustrated in FIG. 11A, after a user adjusts a position of a sample volume, when the user selects a Caliper button and then selects a Velocity button of a control panel that is displayed on a third area 1130, the ultrasound apparatus 100 may display a reference line and reference points for measurement of a velocity of blood flow with respect to a Doppler image that is displayed on a first area 1110. The ultrasound apparatus 100 may activate all of a reference line and reference points 1100, 1101, 1102, and 1103 that are displayed on the screen, so that the reference line and the reference points 1100, 1101, 1102, and 1103 may be moved according to a user's touch input.

Thus, according to the present exemplary embodiment, the user may touch and simultaneously move the reference point 1100, thereby selecting a measurement position to measure a maximum velocity (cm/s) of a blood flow.

When the user touches the reference point 1100, the reference point 1100 and a Doppler image around the reference point 1100 are obstructed by a finger. Thus, the ultrasound apparatus 100 may display a copy image having a predetermined size with respect to a user-touched portion, on a second area 1120. The reference point 1100 that is displayed on the user-touched portion may be located at a center of the second area 1120.

When the user touches and simultaneously drags the reference point 1100, a point at which a touch input is detected is continuously changed according to drag inputs, so that the ultrasound apparatus 100 may change a copy image in real-time with respect to the point at which the touch input is detected and may display the copy image on the second area 1120. That is, the copy image having a predetermined size with respect to the reference point 1100 may be changed in real-time and may be displayed on the second area 1120.

The user may recognize the reference point 1100 and an image around the reference point 1100, which are obstructed by a finger, in the first area 1110 by referring to the copy image displayed on the second area 1120.

As illustrated in FIG. 11B, when the user moves the reference point 1100 to a user-desired position and then takes off the finger from the touch screen, the ultrasound apparatus 100 no longer displays the copy image on the second area 1120. Then, the ultrasound apparatus 100 may provide the maximum velocity (cm/s) at the reference point 1100.

Because the reference line and the reference points 1100, 1101, 1102, and 1103 that are displayed on the screen are all activated, the user may freely change positions of at least one of the reference points 1100, 1101, 1102, and 1103 by touching and dragging at least one of the reference points 1100, 1101, 1102, and 1103.

In the present exemplary embodiment, the ultrasound apparatus 100 may allow the user to exactly recognize a position of the reference point, which is obstructed by a touch instrument (e.g., a finger or an electronic pen), by using the copy image, so that the ultrasound apparatus 100 may help the user to exactly select a velocity measurement position in the Doppler image.

Figure 12A:
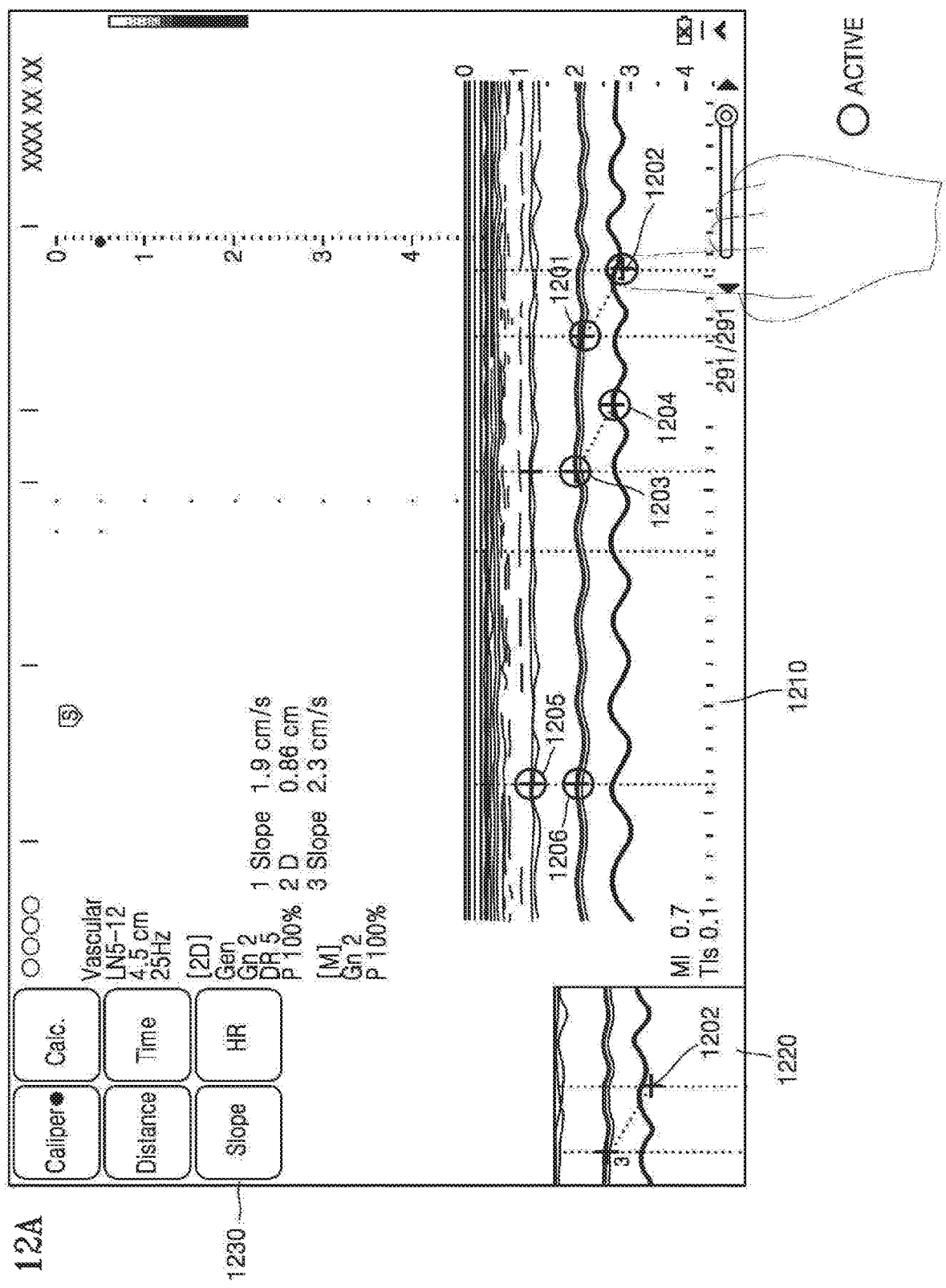
FIGS. 12A and 12B illustrate screens for providing a copy image and a plurality of activated objects related to an M mode image, according to an exemplary embodiment.
Figure 12B:
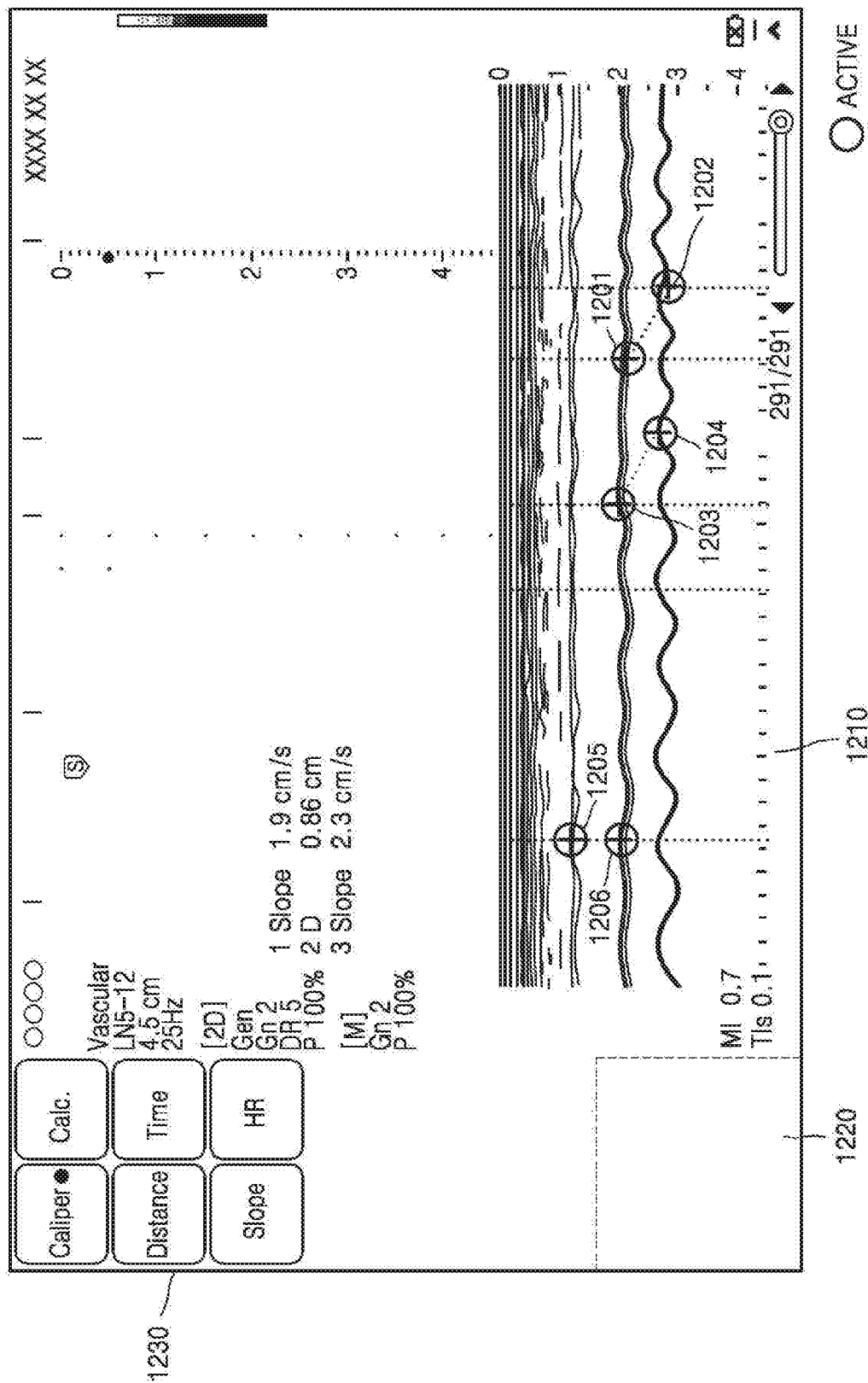

FIGS. 12A and 12B illustrate screens for providing a copy image and a plurality of activated objects related to an M mode image, performed by the ultrasound apparatus 100, according to an exemplary embodiment.

The M mode image indicates an image in which a motion of an organ is expressed as brightness, by using ultrasound echo signals that are repeatedly obtained with respect to one fixed scan line. The M mode image is mainly used in observing the motion of an organ such as the heart, which has valves that move fast. When there is no motion of the organ, the M mode image shows flat lines that are horizontally parallel to each other, but the flat lines may become waves according to the motion of the organ.

As illustrated in FIG. 12A, after a user adjusts a position of a reference line in the M mode image, when the user selects a Caliper button and then selects a Slope button of a control panel that is displayed on a third area 1230, the ultrasound apparatus 100 may display an object for measurement of a slope on the M mode image that is displayed on a first area 1210.

The user may touch and simultaneously make a dragging motion from a first portion corresponding to a first reference point 1201 of the M mode image to a second portion corresponding to a second reference point 1202 of the M mode image, thereby selecting a measurement position for the measurement of the slope. The ultrasound apparatus 100 may activate all of the objects corresponding to a first reference point 1201 displayed at the first portion and a second reference point 1202 displayed at the second portion. Thus, the user may minutely adjust the measurement position for the measurement of the slope by freely changing positions of the first object 1201 and the second object 1202 in a touch and drag manner. According to the present exemplary embodiment, objects corresponding to a third reference point 1203, a fourth reference point 1204, a fifth reference point 1205, and a sixth reference point 1206 that are movable on the M mode image may be all activated.

When the user performs dragging from the first reference point 1201 to the second reference point 1202 by using a finger, a position at which a touch input is detected is continuously changed, so that the ultrasound apparatus 100 may change a copy image in real-time with respect to the position at which the touch input is detected and may display the copy image on a second area 1220. For example, the user may recognize an exact position of a second reference point 1202, which is obstructed by a finger, in the first area 1210 by referring to the copy image displayed on the second area 1220.

As illustrated in FIG. 12B, when the user moves the reference point 1200 to a user-desired position and then takes off the finger from the touch screen, the ultrasound apparatus 100 no longer displays the copy image on the second area 1220.

Because reference points 1201, 1202, 1203, 1204, 1205, and 1206 that are displayed on the screen are all activated, the user may freely change positions of at least one of the reference points 1201, 1202, 1203, 1204, 1205, and 1206 by touching and dragging at least one of the reference points 1201, 1202, 1203, 1204, 1205, and 1206.

In the present exemplary embodiment, the ultrasound apparatus 100 may allow the user to exactly recognize a position of the reference point, which is obstructed by a touch instrument (e.g., a finger or an electronic pen), by using the copy image, so that the ultrasound apparatus 100 may help the user to exactly select a slope measurement position in the M mode image.

Figure 13A:
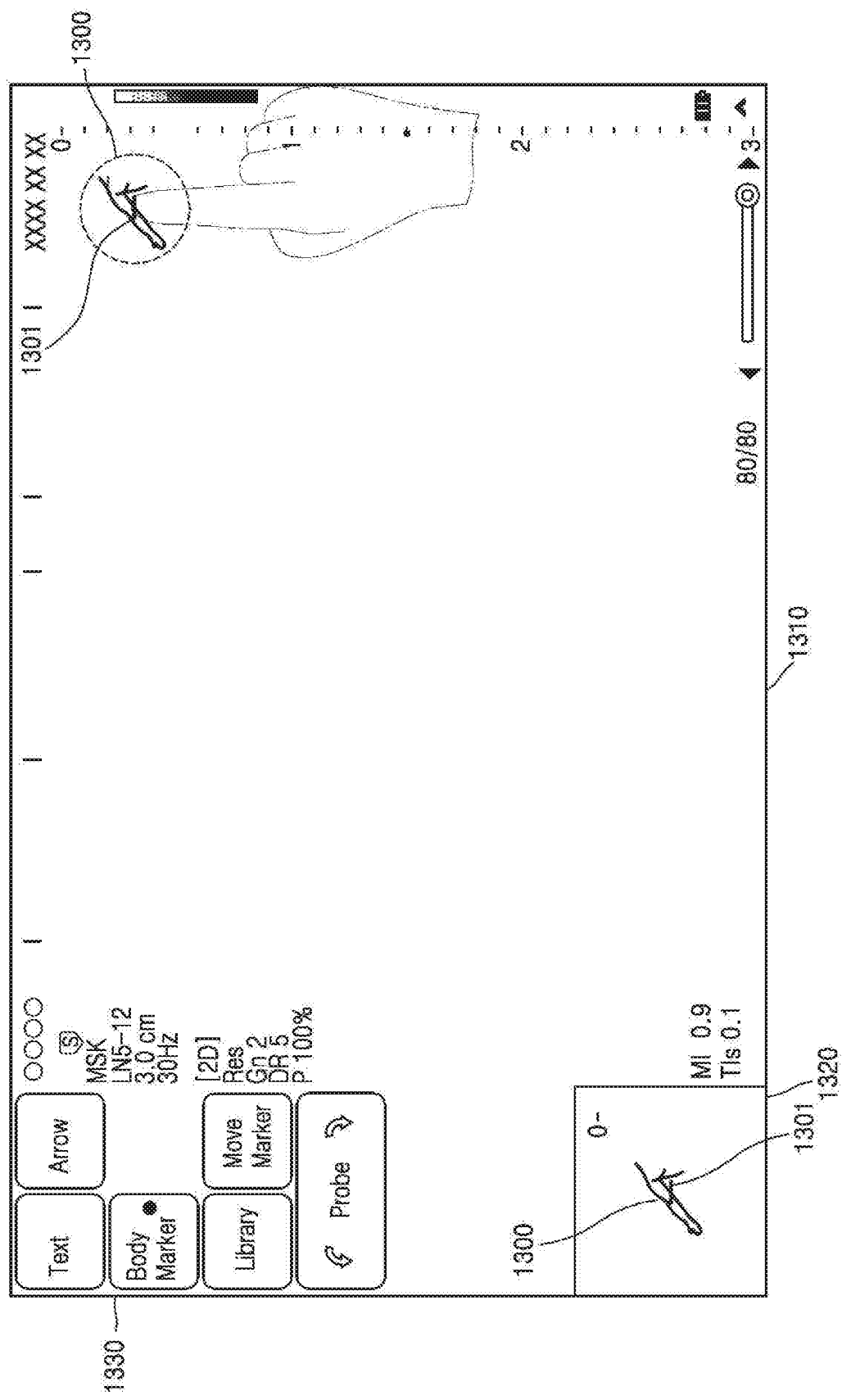
Figure 13B:
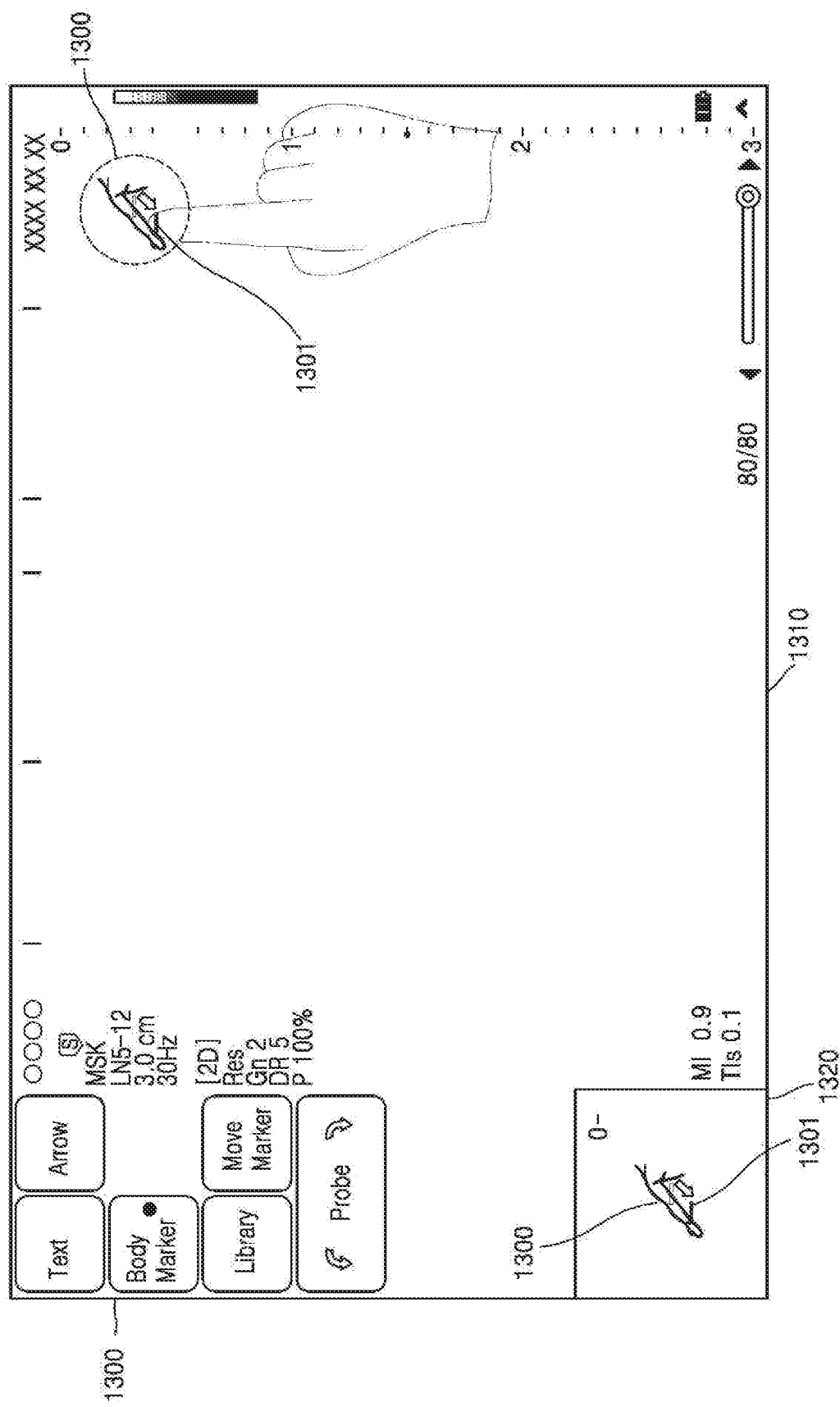

FIGS. 13A, 13B and 13C illustrate screens for providing a copy image related to generation of a body marker, performed by the ultrasound apparatus 100, according to an exemplary embodiment.

As illustrated in FIG. 13A, when a user selects a Body Marker button of a control panel that is displayed on a third area 1330, the ultrasound apparatus 100 may detect the user selection and may display a list of target figures indicating targets on a screen. For example, the list of target figures may include an arm figure, a leg figure, a womb figure, a heart figure, or the like.

When the user selects one target figure (e.g., the arm figure) from the list of target figures, the ultrasound apparatus 100 may display a body marker 1300 on an ultrasound image, wherein the body marker 1300 includes the selected target figure (i.e., the arm figure) and a probe FIG. 1301 indicating a probe position. In this case, the user may touch and simultaneously move the probe FIG. 1301 that indicates the probe position and that is included in the body marker 1300.

When the user touches the body marker 1300 by using a finger, the body marker 1300 and the probe FIG. 1301 indicating the probe position are obstructed by the finger. Thus, the ultrasound apparatus 100 may display a copy image having a predetermined size with respect to a user-touched portion on a second area 1320. The body marker 1300 that is displayed on the user-touched portion may be located at a center of the second area 1320. In particular, according to the present exemplary embodiment, the target figure that is included in the body marker 1300 may be located at the center of the second area 1320.

As illustrated in FIG. 13B, when the user touches and simultaneously moves the probe FIG. 1301 that indicates the probe position and that is included in the body marker 1300, in a lower left direction, the ultrasound apparatus 100 may change and display a position of the probe FIG. 1301, which indicates the probe position, in a copy image in real-time. According to the present exemplary embodiment, the target figure (e.g., the arm figure) may be constantly located at the center of the second area 1320, and only the position of the probe FIG. 1301 indicating the probe position may be changed as compared to FIG. 13A.

Thus, in the present exemplary embodiment, the user may recognize an exact position of the probe FIG. 1301, which is obstructed by a finger, in the first area 1310 by referring to the copy image displayed on the second area 1320.

As illustrated in FIG. 13C, when the user takes off the finger from the body marker 1300, the ultrasound apparatus 100 no longer displays the copy image of the body marker 1300, on the second area 1320.

In the present exemplary embodiment, the ultrasound apparatus 100 may allow the user to exactly recognize the probe FIG. 1301 by using the copy image, wherein the probe FIG. 1301 indicates the probe position and is obstructed by a touch instrument (e.g., a finger or an electronic pen), so that the ultrasound apparatus 100 may help the user to generate the body marker 1300 that exactly indicates a position of a target at which an ultrasound image is obtained.

Figure 14:
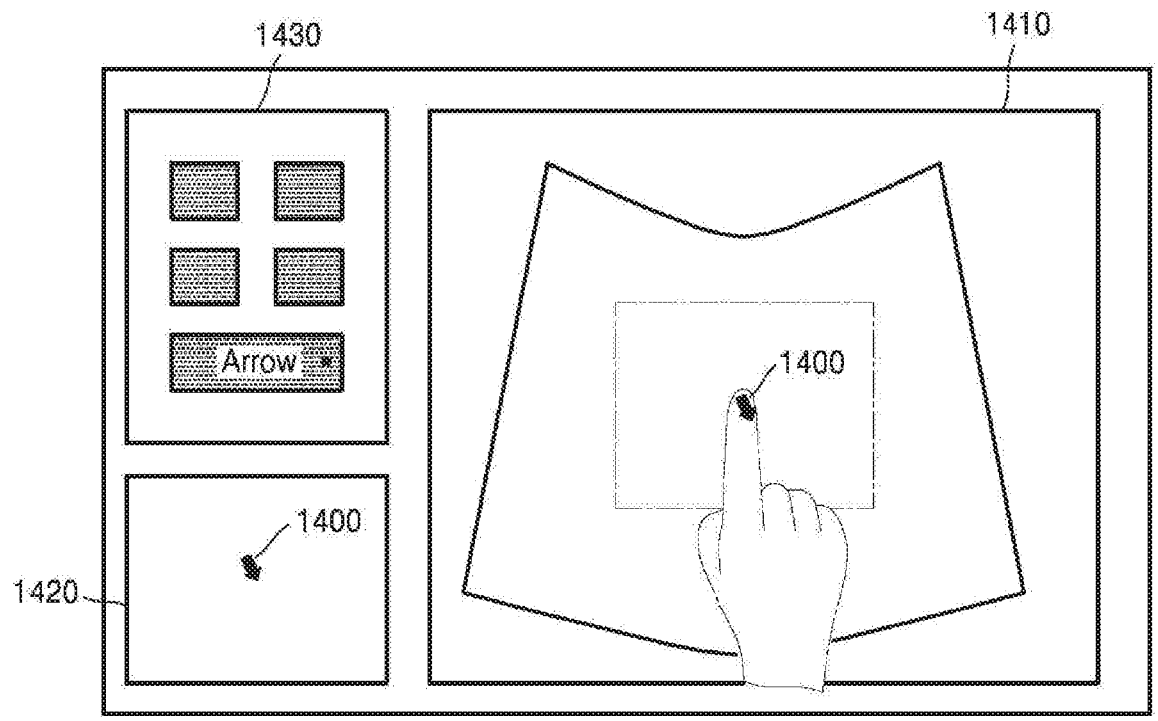
FIG. 14 illustrates a screen for providing a copy image related to an indication display, according to an exemplary embodiment.

FIG. 14 illustrates a screen for providing a copy image related to an indication display, performed by the ultrasound apparatus 100, according to an exemplary embodiment.

As illustrated in FIG. 14, when a user selects an Arrow button of a control panel that is displayed on a third area 1430, the ultrasound apparatus 100 may detect the user selection and may display an arrow 1400 on an ultrasound image. In this case, the user may touch and simultaneously move the arrow 1400 to a portion of an image (e.g., a possible tumor area, a finger of a fetus, or the like).

However, when the user touches the arrow 1400, the arrow 1400 and the ultrasound image around the arrow 1400 are obstructed by a finger. Thus, the ultrasound apparatus 100 may display a copy image having a predetermined size with respect to a user-touched portion, on a second area 1420. The arrow 1400 that is displayed on the user-touched portion may be located at a center of the second area 1420.

When the user touches and simultaneously drags the arrow 1400, a point at which a touch input is detected is continuously changed according to drag inputs, so that the ultrasound apparatus 100 may change a copy image in real-time with respect to the point at which the touch input is detected and may display the copy image on the second area 1420. The user may recognize an exact position of the arrow 1400, which is obstructed by a finger in the first area 1410, by referring to the copy image displayed on the second area 1420.

When the user moves the arrow 1400 to a user-desired position and then takes off the finger from the touch screen, the ultrasound apparatus 100 no longer displays the copy image on the second area 1420.

In an exemplary embodiment of FIG. 14, the arrow 1400 is described as an example of an indicator. However, in one or more exemplary embodiments, various types (e.g., a finger shape, a star shape, or the like) of the indicator may be used.

In the present exemplary embodiment, the ultrasound apparatus 100 may help the user to exactly recognize a position of the indicator, which is obstructed by a touch instrument (e.g., a finger or an electronic pen), by using the copy image.

Figure 15:
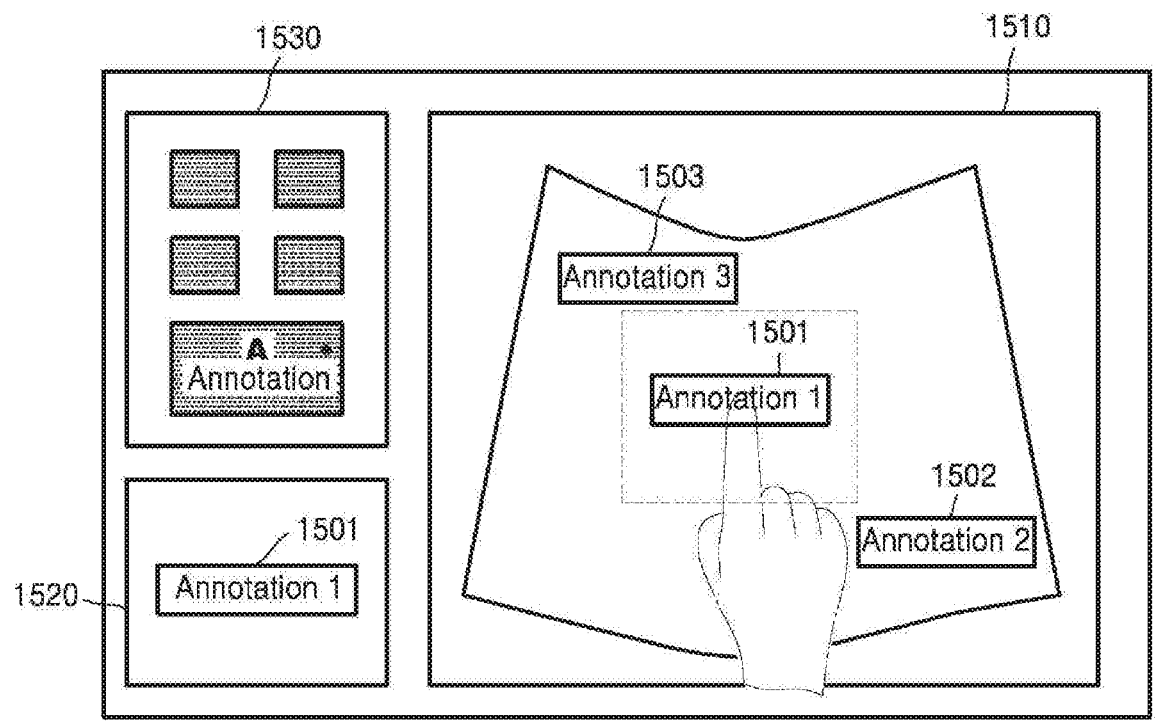
FIG. 15 illustrates a screen for providing a copy image and a plurality of activated objects related to annotation, according to an exemplary embodiment.

FIG. 15 illustrates a screen for providing a copy image and a plurality of activated objects related to an annotation, performed by the ultrasound apparatus 100, according to an exemplary embodiment.

As illustrated in FIG. 15, when a user selects an Annotation button of a control panel that is displayed on a third area 1530, the ultrasound apparatus 100 may detect the user selection and then may display a window for an input of a first annotation 1501 on an ultrasound image. In this case, the user may input the first annotation 1501, and may touch and simultaneously move the input first annotation 1501 to a target indication portion (e.g., a possible tumor area or the like).

However, when the user touches the first annotation 1501, the first annotation 1501 and an ultrasound image around the first annotation 1501 are obstructed by a finger. Thus, the ultrasound apparatus 100 may display a copy image having a predetermined size with respect to a user-touched portion, on a second area 1520. The first annotation 1501 that is displayed on the user-touched portion may be located at a center of the second area 1520.

When the user touches and simultaneously drags the first annotation 1501, a point at which a touch input is detected is continuously changed according to drag inputs, so that the ultrasound apparatus 100 may change a copy image in real-time with respect to the point at which the touch input is detected and may display the copy image on the second area 1520. The user may recognize an exact position of the first annotation 1501, which is obstructed by a finger in the first area 1510, by referring to the copy image displayed on the second area 1520.

When the user moves the first annotation 1501 to a user-desired position and then takes off the finger from the touch screen, the ultrasound apparatus 100 no longer displays the copy image on the second area 1520.

The ultrasound apparatus 100 may activate all of annotations 1501, 1502, and 1503 that are displayed on the screen. Thus, the user may freely change positions of the annotations 1502 and 1503 by touching and dragging the annotations 1502 and 1503.

In the present exemplary embodiment, the ultrasound apparatus 100 may help the user to exactly recognize the position of the annotation, which is obstructed by a touch instrument (e.g., a finger or an electronic pen), by using the copy image.

Figure 16:
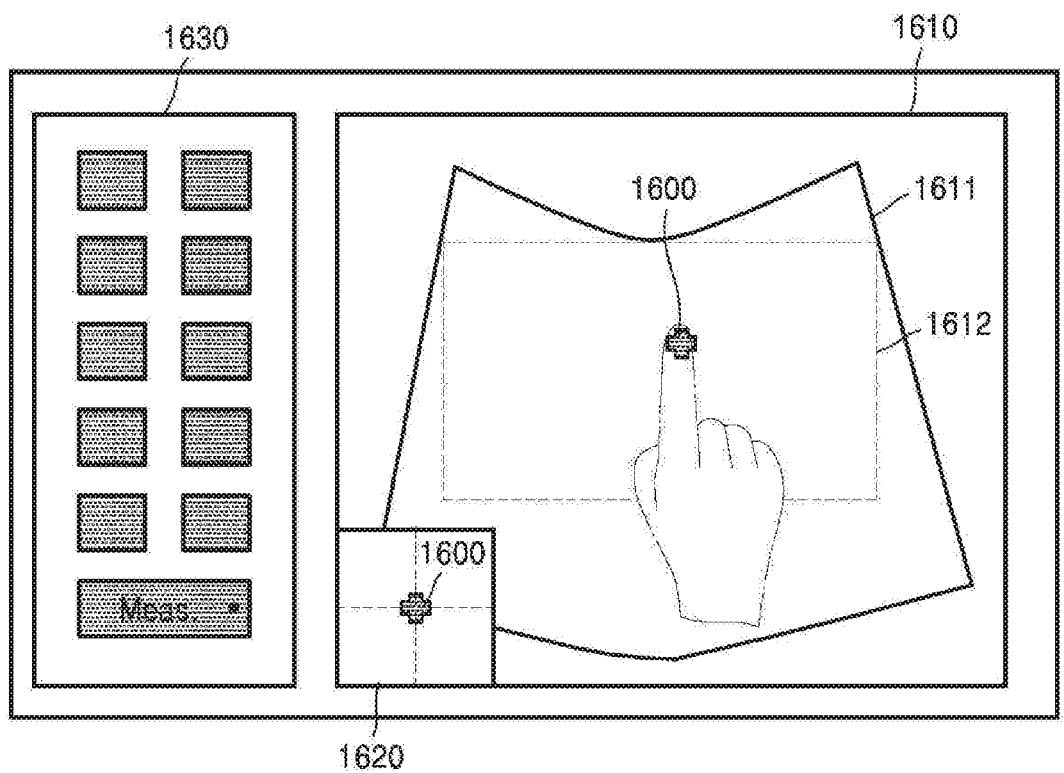
FIG. 16 illustrates a screen for displaying a copy image on a non-interest area of an ultrasound image, according to an exemplary embodiment.

FIG. 16 illustrates a screen for displaying a copy image on a non-interest area of an ultrasound image, performed by the ultrasound apparatus 100, according to an exemplary embodiment.

A second area 1620 on which the copy image is displayed may include a residual area of a first area 1610 on which an ultrasound image 1611 is displayed, wherein the residual area does not include an interest area 1612 of the first area 1610 which is selected by a user. The GUI is displayed on a third area 1630.

That is, the ultrasound apparatus 100 may display the copy image in the first area 1610 on which the ultrasound image 1611 is displayed, or may overlap the copy image with the first area 1610 and may display the copy image. For example, the ultrasound apparatus 100 may extract the non-interest area excluding the interest area 1612 of the ultrasound image 1611 that is displayed on a touch screen, and may display the copy image on the non-interest area.

The non-interest area may be the residual area excluding the interest area 1612 that is selected by the user. For example, in a mode for observing a fetus, the non-interest area may be a residual area excluding a predetermined area on which the fetus is displayed.

In the present exemplary embodiment, when the user takes off a touch instrument (e.g., a finger or an electronic pen) from the touch screen, the ultrasound apparatus 100 no longer displays the copy image that is displayed on the non-interest area.

Figure 17A:
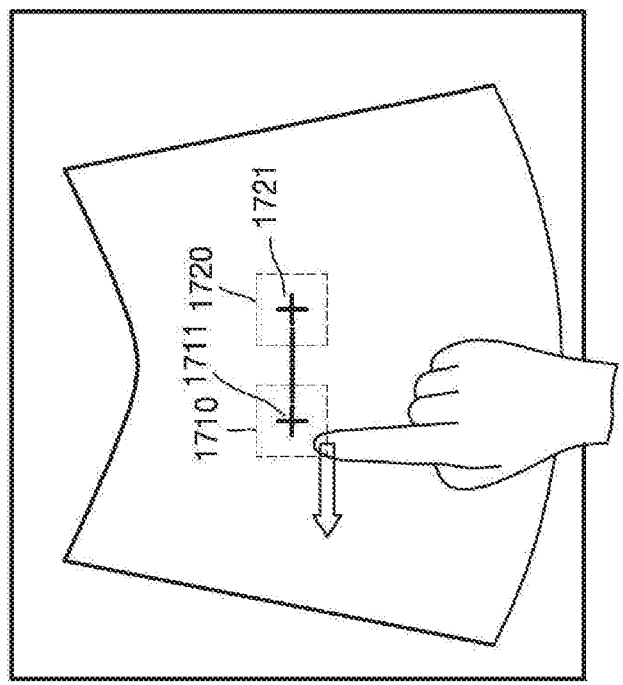
FIGS. 17A and 17B illustrate a touch recognition range with respect to an object, according to an exemplary embodiment.
Figure 17B:
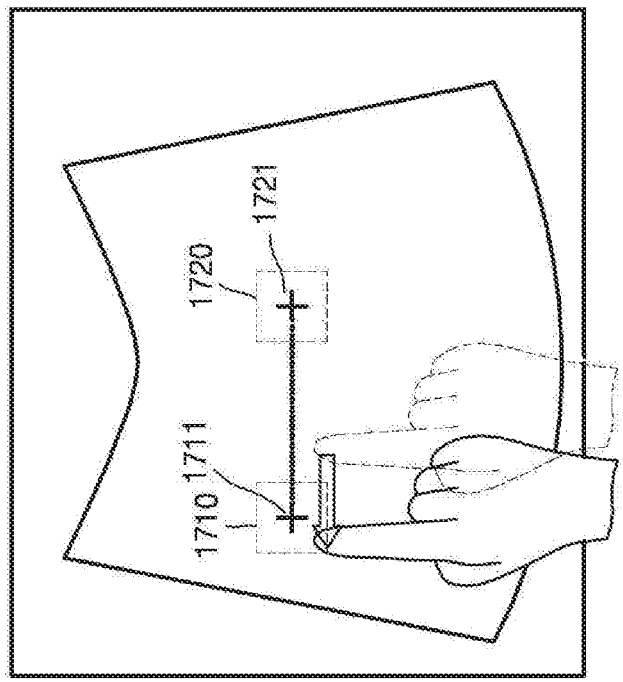

FIGS. 17A and 17B illustrate a touch recognition range with respect to an object, according to an exemplary embodiment.

As illustrated in FIG. 17A, a user may drag a first object 1711 away from a second object 1721 disposed in an area 1720 to increase a length of a measurement line. Although a user does not exactly touch a first object 1711, when the user touches a first area 1710 around the first object 1711, the ultrasound apparatus 100 may recognize that the first object 1711 is touched. That is, because the user might not exactly touch the object, or although the user exactly touches the object, an entire image of the object may be obstructed by a finger, or the like, the ultrasound apparatus 100 may expand the touch recognition range with respect to the object.

As illustrated in FIG. 17B, in a case where the user does not exactly touch the first object 1711 but touches and simultaneously drags the first area 1710 around the first object 1711 in a left direction, the ultrasound apparatus 100 may determine that the ultrasound apparatus 100 has received a touch and drag input with respect to the first object 1711, so that the ultrasound apparatus 100 may move the first object 1711 in the left direction and then may display the first object 1711.

FIGS. 18A, 18B, 19A and 19B illustrate cases in which touch recognition ranges of objects overlap with each other, according to an exemplary embodiment.

Figure 18B:
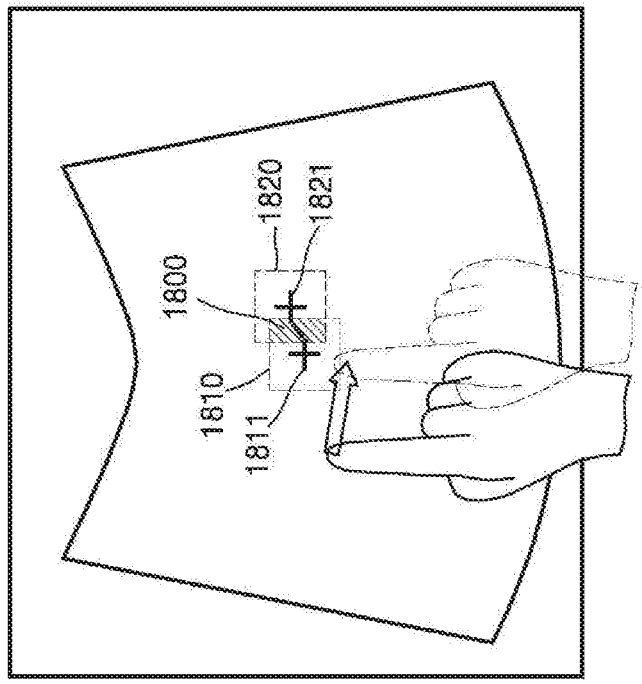
FIGS. 18A and 18B illustrate cases in which touch recognition ranges of objects overlap with each other, according to an exemplary embodiment.
Figure 18A:
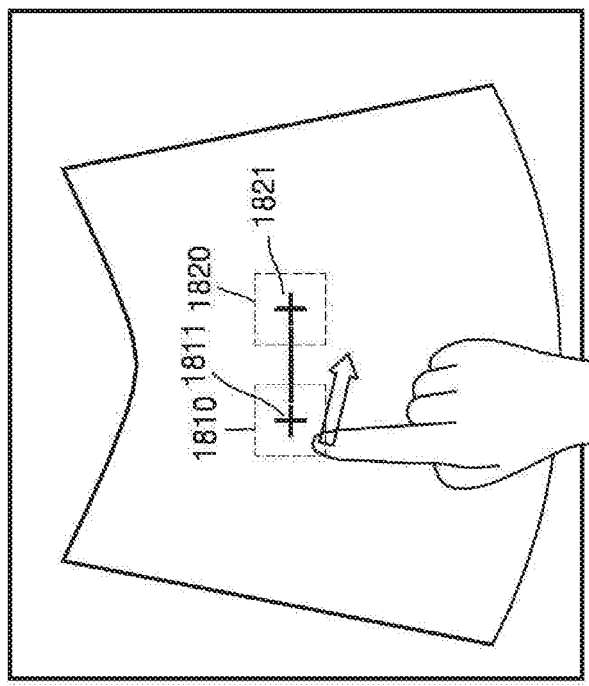

As illustrated in FIG. 18A, a user may drag a first object 1811 toward a second object 1821 to decrease a length of a measurement line. Here, when a distance between the first object 1811 and the second object 1821 is less than a predetermined distance, as illustrated in FIG. 18B, a touch recognition range 1810 of the first object 1811 and a touch recognition range 1820 of the second object 1821 may overlap with each other (area 1800).

As illustrated in FIG. 19A, when the user touches and drags an overlapped area 1900 in which a touch recognition range 1910 of a first object 1911 and a touch recognition range 1920 of a second object 1921 overlap with each other, the ultrasound apparatus 100 may move one of the first object 1911 and the second object 1921, based on priority order information.

For example, as illustrated in FIG. 19B, when a lastly-moved object has a priority, the ultrasound apparatus 100 may compare a movement time of the first object 1911 with a movement time of the second object 1921. When the movement time of the second object 1921 precedes the movement time of the first object 1911, the ultrasound apparatus 100 may move the first object 1911 according to a user's touch and drag input with respect to the overlapped area 1900.

Figure 20:
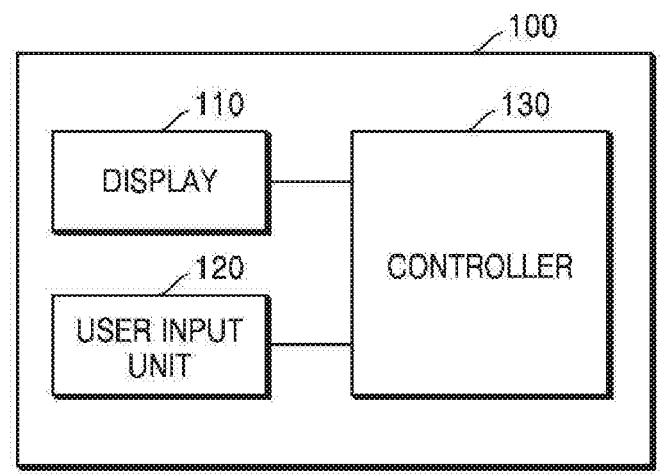
FIG. 20 is a block diagram illustrating a structure of the ultrasound apparatus, according to an exemplary embodiment.

FIG. 20 is a block diagram illustrating a structure of the ultrasound apparatus 100, according to an exemplary embodiment.

The ultrasound apparatus 100 may include the display 110, the user input unit 120, and a controller 130. However, not all shown elements are necessary elements. That is, the ultrasound apparatus 100 may be embodied with more or less elements than the shown elements.

Hereinafter, the aforementioned elements are described.

As described above, the display 110 and a touchpad may form a mutual layer structure and thus may be formed as a touch screen. That is, in the present exemplary embodiment, the display 110 may be used as both an output device and an input device.

The display 110 may display an ultrasound image on a first area of the touch screen. The display 110 may display a copy image on a second area that is different from the first area on which the ultrasound image is displayed. The display 110 may display the copy image on the second area so that an object that is displayed on the first area at a position at which a touch input is detected may be located at a center of the second area.

The display 110 may display a copy image of a partial image, which is changed according to drag inputs, on the second area of the touch screen. That is, according to the drag inputs by the user, the copy image that is displayed on the second area may be changed in real-time. The display 110 may move a predetermined object, which is dragged by the user, into the first area and then may display the predetermined object.

The display 110 may change a control panel for adjustment of parameter values related to the ultrasound image, according to a predetermined mode, and then may display the control panel on a third area of the touch screen.

Figure 22A:
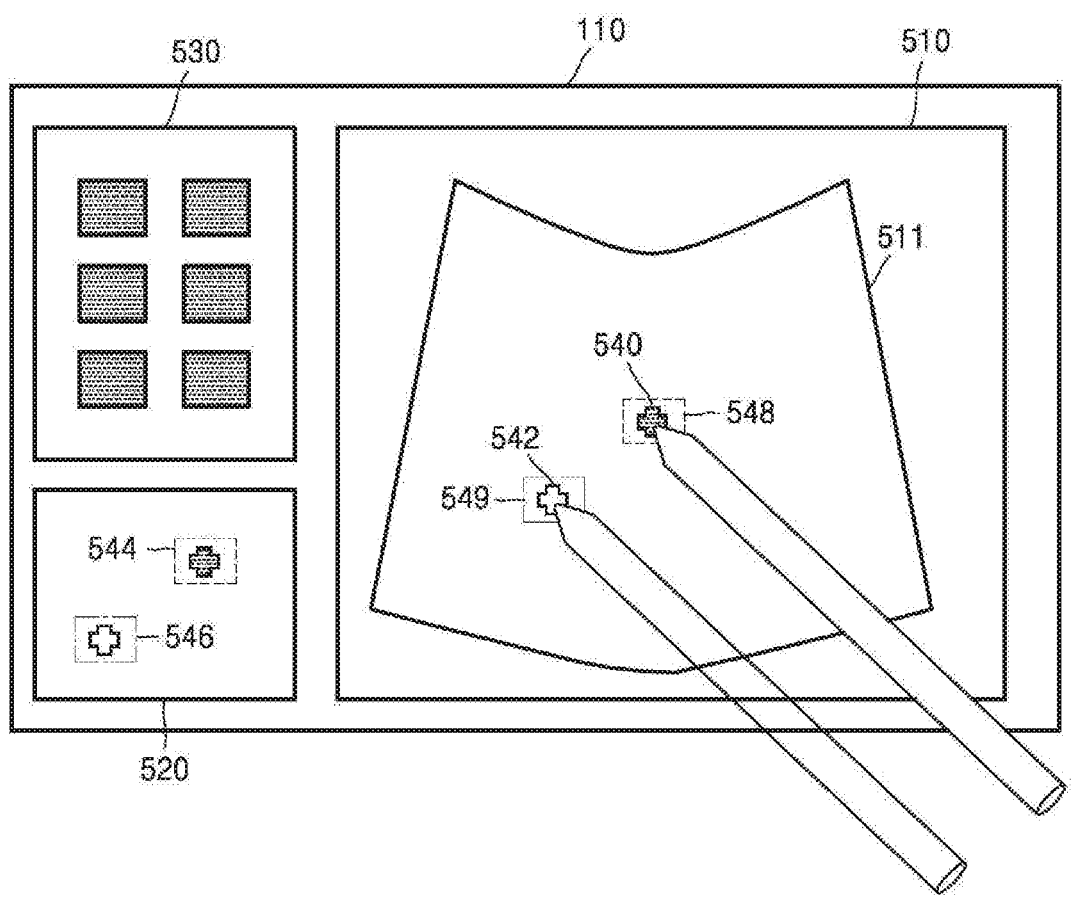
FIG. 22A illustrates a display of copy images, according to an exemplary embodiment.

The display 110 may display a plurality of copy images, as shown in FIG. 22A. For example, when multiple touch inputs 540 and 542 are detected, the display 110 may display a plurality of copy images 544 and 546 about a plurality of partial images 548 and 549 on the second area 520, wherein the plurality of partial images correspond to at least two portions of the ultrasound image, respectively.

The display 110 may display a copy image on the second area, wherein the copy image is obtained by magnifying or reducing a partial image by a predetermined ratio.

The display 110 may display together a plurality of activated objects and the ultrasound image. The display 110 may display the activated objects to partially overlap with the ultrasound image, may display the activated objects on the ultrasound image, or may display the activated objects in an area of a screen which is different from another area of the screen on which the ultrasound image is displayed.

The display 110 may move at least one object among the activated objects, according to a user's touch and drag input, and then may display the at least one object.

The display 110 may move and display a first object according to a touch and drag input with respect to the first area, and may move and display a second object according to a touch and drag input with respect to the second area. The first area may be an area in which the first object is recognized as being touched, and the second area may be an area in which the second object is recognized as being touched. That is, according to the present exemplary embodiment, the user may change a position of an object by touching an area around the object without exactly touching the object.

The display 110 may move and display each of the first and second objects according to multiple touch inputs.

The user input unit 120 is a means by which the user inputs data to control the ultrasound apparatus 100. For example, the user input unit 120 may be formed of, but is not limited to, a key pad, a dome switch, a touchpad (a touch capacitive type touchpad, a pressure resistive type touchpad, an infrared beam sensing type touchpad, a surface acoustic wave type touchpad, an integral strain gauge type touchpad, a Piezo effect type touchpad, or the like), a jog wheel, a jog switch, or the like. In particular, as described above, when a display panel and the touchpad form a layer structure, the structure may be a touch screen. In the present exemplary embodiment, the user input unit 120 may detect an actual touch and also may detect a proximate touch.

The user input unit 120 may detect a touch input (e.g., a touch and hold input, a tap input, a double-tap input, a flick input, a touch and drag input, or the like) with respect to an ultrasound image. The user input unit 120 may detect a drag input that starts at a position at which the touch input is first detected. The user input unit 120 may detect multiple touch inputs (e.g., a pinch input) with respect to at least two portions of the ultrasound image.

The user input unit 120 may receive a touch and drag input with respect to the first area within a predetermined radius from a point at which the first object among the activated objects is displayed, and may receive a touch and drag input with respect to the second area within the predetermined radius from a point at which the second object among the activated objects is displayed. A value of the predetermined radius may be set by the user or the ultrasound apparatus 100 and may be changed.

The user input unit 120 may receive a touch and drag input with respect to an area in which the first area and the second area overlap with each other.

The controller 130 controls operations of the ultrasound apparatus 100 and may include one or more processors. For example, the controller 130 may control the display 110 and the user input unit 120.

For example, the controller 130 may control the display 110 to extract a partial image of the ultrasound image that corresponds to the touch input, and then to display a copy image of the partial image on the second area that is different from the first area.

The controller 130 may obtain information about a position of the touch screen at which the touch input is detected, and may extract a partial image from the ultrasound image, wherein the partial image has a preset size with respect to the position at which the touch input is detected. The controller 130 may select the second area that is different from the first area on which the ultrasound image is displayed and that is different from the third area on which the control panel is displayed as a GUI.

When the controller 130 no longer detects a touch input, the controller 130 may remove the copy image from the second area. That is, when the user touches a specific portion of the ultrasound image and then takes off a finger from the ultrasound image, the copy image that is displayed on the second area may disappear.

The controller 130 may extract a plurality of objects that are movable during a predetermined mode, and may activate the objects so that each of the objects may be moved according to a user's touch input.

When the touch and drag input with respect to the area in which the first area and the second area overlap with each other is received, the controller 130 may control the display 110 to move and display one of the first and second objects based on the priority order information. For example, the controller 130 may compare movement time information of the first object with movement time information of the second object, and may control the display 110 to move and display one of the first and second objects, according to the comparison result.

Figure 21:
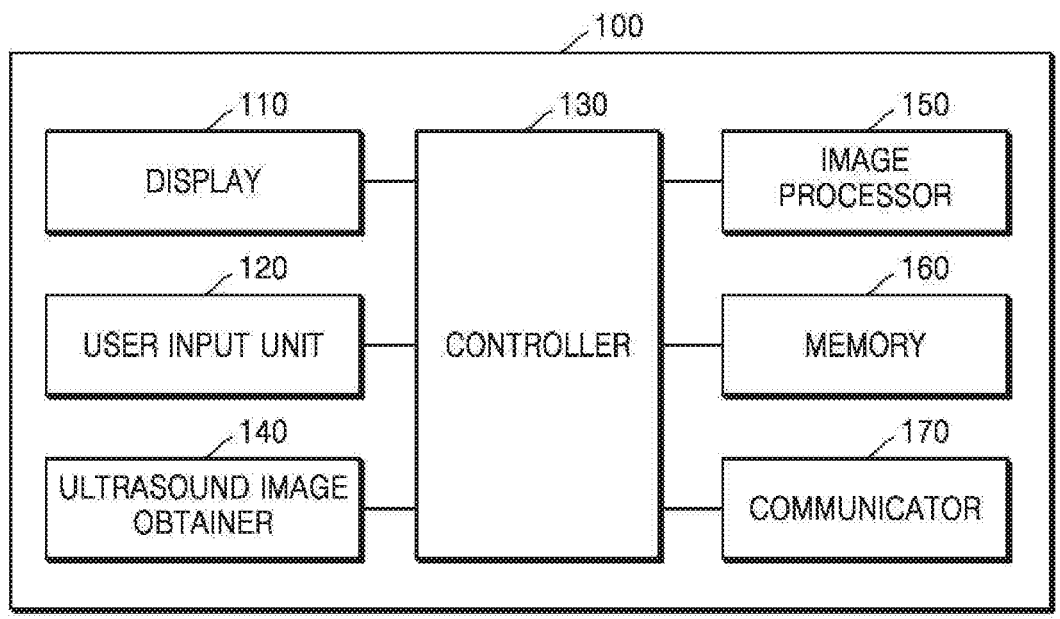
FIG. 21 is a diagram illustrating a structure of the ultrasound apparatus, according to an exemplary embodiment.

FIG. 21 is a diagram illustrating a structure of the ultrasound apparatus 100, according to an exemplary embodiment.

As illustrated in FIG. 21, the ultrasound apparatus 100 may include an ultrasound image obtainer 140, an image processor 150, a memory 160, and a communicator 170, in addition to the display 110, the user input unit 120, and the controller 130.

The ultrasound image obtainer 140 may include a probe (not shown) to transmit and receive an ultrasound signal, and a beamformer (not shown) to perform a transmit focusing operation and a receive focusing operation with respect to the ultrasound signal. In the present exemplary embodiment, the probe may include at least one of 1D (dimension), 1.5D, 2D (matrix), and 3D probes.

The image processor 150 may capture a partial image corresponding to a touch input and then may generate a copy image of the partial image. When a touch input that is maintained over a predetermined time is detected, the image processor 150 may capture the partial image and then may generate the copy image. For example, when a touch input that is maintained over 2 seconds is detected, the image processor 150 may generate the copy image. The image processor 150 may capture the partial image at regular intervals or may capture the partial image when a position of the touch input is changed. A method of generating the copy image, performed by the image processor 150, is known to one of ordinary skill in the art related to the image processing technology; thus, detailed descriptions thereof are omitted.

The memory 160 may store a program for processing and controlling the controller 130, and/or pieces of data (e.g., a preset gain value, an ultrasound image, examinee information, probe information, a body marker, or the like) that are input/output.

The memory 160 may include a flash memory-type storage medium, a hard disk-type storage medium, a multimedia card micro-type storage medium, a card type memory (e.g., an SD card memory or an XD card memory), a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disc, and an optical disc. The ultrasound apparatus 100 may operate a web storage system that performs a storing function of the memory 160 over the Internet.

The communicator 170 may include one or more configuring elements that allow communication between the ultrasound apparatus 100 and an external device (not shown). For example, the communicator 170 may include a near field communication (NFC) module, a mobile communication module, a wireless internet module, a wired internet module, or the like.

The NFC module may include, but is not limited to, a wireless LAN (Wi-Fi), Bluetooth, BLE, Ultra Wideband (UWB), ZigBee, NFC, Wi-Fi Direct (WFD), and infrared Data Association (IrDA).

The mobile communication module exchanges a wireless signal with at least one of a base station, an external terminal, and a server via a mobile communication network. The wireless internet module is for accessing wireless Internet. The wireless internet module may be embedded in the ultrasound apparatus 100 or may be arranged outside the ultrasound apparatus 100. The wired internet module is for access to wired internet.

In the present exemplary embodiment, the communicator 170 may transmit the ultrasound image or the like to the external device. The external device may include, but is not limited to, a mobile phone, a smart phone, a laptop computer, a tablet PC, an electronic book terminal, a terminal for digital broadcasting, a personal digital assistant (PDA), a portable multimedia player (PMP), a digital camera, or the like.

Figure 22B:
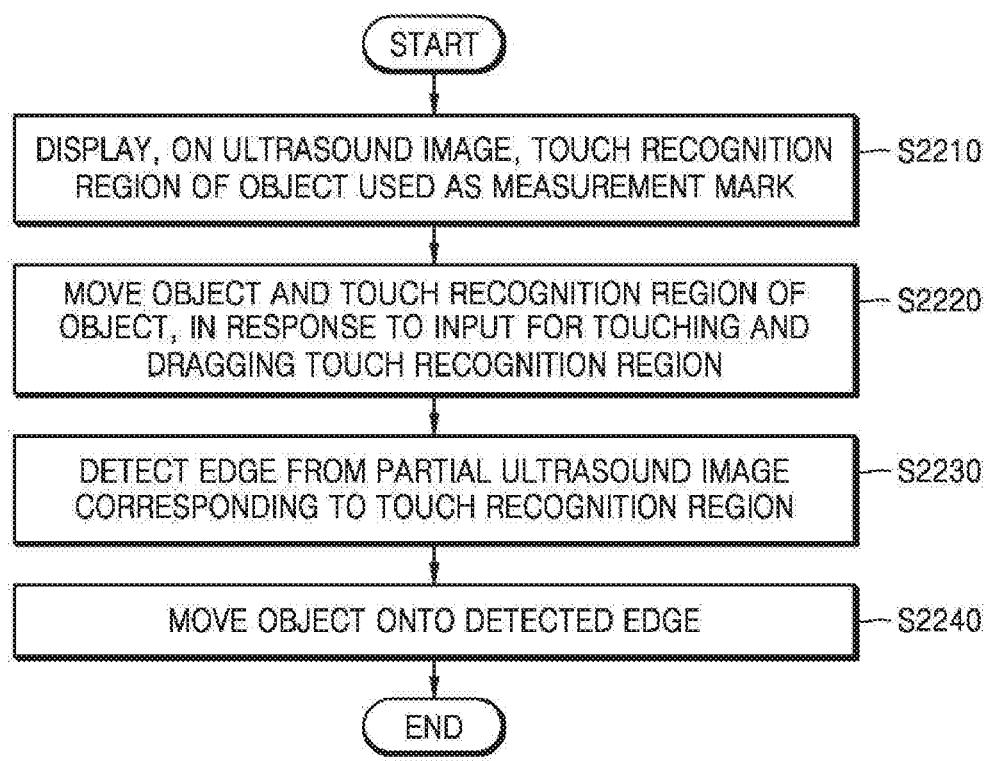
FIG. 22B is a flowchart illustrating a method of displaying an object, according to an exemplary embodiment.

FIG. 22B is a flowchart illustrating a method of displaying an object, according to an exemplary embodiment.

In operation S2210, the ultrasound apparatus 100 may display, on an ultrasound image, a touch recognition region of an object which is used as a measurement mark.

According to an exemplary embodiment, the object used as the measurement mark may be an element of a caliper for specifying a length, a circumference, an area, and the like. For example, a line-shape caliper for measuring a length may include objects at both ends of the caliper, the objects being used as the measurement marks. An oval-shape caliper for measuring an area may include three or four objects each being disposed on some or all of the endpoints of the long axis and short axis, of the oval-shape caliper.

The touch recognition region may mean an extended touch recognition range. For example, the touch recognition region may indicate a predetermined-size region (e.g., a region within a radius of 1 cm from an object) that surrounds the object. Therefore, when a user touches a boundary of the touch recognition region or an inside area of the touch recognition region, the ultrasound apparatus 100 may determine that the object inside (e.g., a center-point) the touch recognition region is selected.

A shape and size of the touch recognition region may vary. For example, the touch recognition region may be, but is not limited to, round, oval, square, pentagonal, or the like. Hereinafter, for convenience of description, it is assumed that the shape of the touch recognition region is round.

According to an exemplary embodiment, the ultrasound apparatus 100 may adjust a size of the touch recognition region. For example, the ultrasound apparatus 100 may adjust the size of the touch recognition region, according to a user input or detected edge information. An operation of adjusting the size of the touch recognition region, the operation being performed by the ultrasound apparatus 100, will be described in detail with reference to FIG. 36.

According to an exemplary embodiment, the ultrasound apparatus 100 may display the boundary of the touch recognition region by using a line or color. For example, the ultrasound apparatus 100 may display a boundary line of the touch recognition region or an inside area of the touch recognition region by using a particular color. For example, the boundary line may include a solid line, a dotted line, a dashed line, a dashed dotted line, or the like.

When a plurality of objects are positioned on the ultrasound image, the ultrasound apparatus 100 may display touch recognition regions respectively corresponding to the plurality of objects, by using different lines or colors or by using a same line or color. For example, the ultrasound apparatus 100 may display a first touch recognition region of a first object by using a blue solid line, and may display a second touch recognition region of a second object by using a red dotted line. For example, the ultrasound apparatus 100 may display boundaries of at least one among the first and second touch recognition regions by using a yellow solid line or a line of another color.

According to an exemplary embodiment, the ultrasound apparatus 100 may differently set shapes of the touch recognition regions that respectively correspond to the plurality of objects. For example, the ultrasound apparatus 100 may set the first touch recognition region of the first object as a round shape, and may set the second touch recognition region of the second object as a square shape.

According to an exemplary embodiment, the ultrasound apparatus 100 may display, on a predetermined area of a screen, a copy image obtained by copying a partial ultrasound image that corresponds to a touch recognition region selected by the user and is extracted from the displayed ultrasound image. According to an exemplary embodiment, the copy image may be an image having the same magnification as the extracted partial ultrasound image, e.g., a magnification ratio of 1. For example, the copy image and the ultrasound image having the same magnification may be both contemporaneously displayed with the same-size measurement mark, for example, a cross-shaped object, on different and separate areas of the same touch screen. As another example, the copy image may be an image obtained by magnifying the extracted partial ultrasound image, e.g., with a magnification ratio greater than 1 by which the displaying parameters of the extracted partial ultrasound image will modified or zoomed to an appropriate magnification degree, while the ultrasound image will be displayed un-zoomed. Of course, the copy image may be displayed with a magnification ratio less than 1, and, in this case, the features in the extracted partial ultrasound image will be reduced and displayed with a reduction in the copy image.

In operation S2220, the ultrasound apparatus 100 may move an object and a touch recognition region of the object, in response to an input for touching and dragging the touch recognition region.

For example, touching and dragging the touch recognition region may mean that the user touches and drags a particular point selected inside the touch recognition region or at a boundary of the touch recognition region. The touched particular point may be different from a position of the object. For example, the user may touch, by using a finger, the particular point that does not obstruct a viewing of the object in the touch recognition region and may drag the particular point.

When the touch recognition region is touched and dragged, the ultrasound apparatus 100 may determine that the object positioned in the touch recognition region is selected. Therefore, in response to the touch and drag input, the ultrasound apparatus 100 may move the object positioned in the touch recognition region. Here, the ultrasound apparatus 100 may move the touch recognition region surrounding the object, according to movement of the object.

In operation S2230, the ultrasound apparatus 100 may detect an edge from the partial ultrasound image corresponding to the touch recognition region. For example, the edge may be a line, i.e., an edge line, formed by connecting points at which brightness variation of a pixel is greater than a threshold value. For example, a group of points (pixels) where brightness is sharply changed in the ultrasound image may be detected as the edge.

According to an exemplary embodiment, the ultrasound apparatus 100 may use the touch recognition region as an edge detection region. For example, the ultrasound apparatus 100 may detect the edge from the partial ultrasound image displayed in the touch recognition region.

The ultrasound apparatus 100 may use morphological image processing so as to detect an edge from an ultrasound image. The morphological image processing is an operation of morphologically analyzing and processing an object displayed on an image. The morphological image processing may include, but is not limited to, at least one of an edge detection algorithm, an image segmentation algorithm, and a machine learning algorithm.

The edge detection algorithm is an image processing technique of detecting a characteristic showing a boundary of a region from an image. For example, the ultrasound apparatus 100 may detect points at which brightness of a pixel is sharply changed and then may extract an edge by connecting the detected points. A type of the edge detection algorithm may include, but is not limited to, edge detection using an operator, Canny edge detection, or the like. Examples of the operator may include Sobel, Prewitt, Roberts, Laplace operators, or the like.

The image segmentation algorithm is an image processing technique of partitioning an image into multiple segments. A type of the image segmentation algorithm may include, but is not limited to, a region developing method/portioning-merging method, a graphically partitioning method, a thresholding method, or the like. For example, according to the image segmentation algorithm, the ultrasound apparatus 100 may detect an edge by partitioning an ultrasound image into small regions, calculating a color and brightness difference between adjacent regions, merging similar regions, and segmenting the ultrasound image into finally-remaining regions.

The ultrasound apparatus 100 may detect an edge by detecting a characteristic region from the ultrasound image, according to the machine learning algorithm.

According to an exemplary embodiment, a size of the touch recognition region and a size of an edge detection region may be equal to or different from each other. For example, the touch recognition region and the edge detection region may be 100% the same or the edge detection region may be larger or smaller than the touch recognition region by a predetermined magnification. When the edge detection region is larger than the touch recognition region by the predetermined magnification, the edge detection region may include the touch recognition region. When the edge detection region is smaller than the touch recognition region by the predetermined magnification, the touch recognition region may include the edge detection region.

For example, when the size of the touch recognition region and the size of an edge detection region are equal to each other, the ultrasound apparatus 100 may detect an edge from an image displayed in the touch recognition region. On the other hand, when the edge detection region is larger than the touch recognition region by 1.5 times, the ultrasound apparatus 100 may detect an edge from an image displayed on a periphery of the touch recognition region.

Hereinafter, for convenience of description, it is assumed that the size of the touch recognition region and the size of an edge detection region are equal to each other.

In operation S2240, the ultrasound apparatus 100 may move the object onto the detected edge. For example, the ultrasound apparatus 100 may move the object to a position of the edge by using coordinates of the detected edge with respect to the pixels of the touchscreen or with respect to the pixels of the ultrasound image.

According to an exemplary embodiment, the ultrasound apparatus 100 may determine a first point among points, based on a plurality of pieces of information regarding distances between the object and points on the detected edge. For example, the ultrasound apparatus 100 may determine the first point that is the closest point to the object among the points on the detected edge. The ultrasound apparatus 100 may move the object to the first point.

Therefore, according to an exemplary embodiment, when the user moves the object, which is used as the measurement mark, toward the edge, the ultrasound apparatus 100 may exactly locate the object on the edge, therefore, the ultrasound apparatus 100 may accurately measure a size of an interest area (e.g., a lesion, a fetus, etc.) included in the ultrasound image.

Hereinafter, with reference to FIGS. 23A through 23D, an operation of moving an object onto a detected edge, the operation being performed by the ultrasound apparatus 100, will be described in detail.

FIGS. 23A through 23D illustrate an operation of displaying a touch recognition region and moving an object to an edge that is automatically detected in the touch recognition region, the operation being performed by the ultrasound apparatus 100, according to an exemplary embodiment.

Figure 23A:
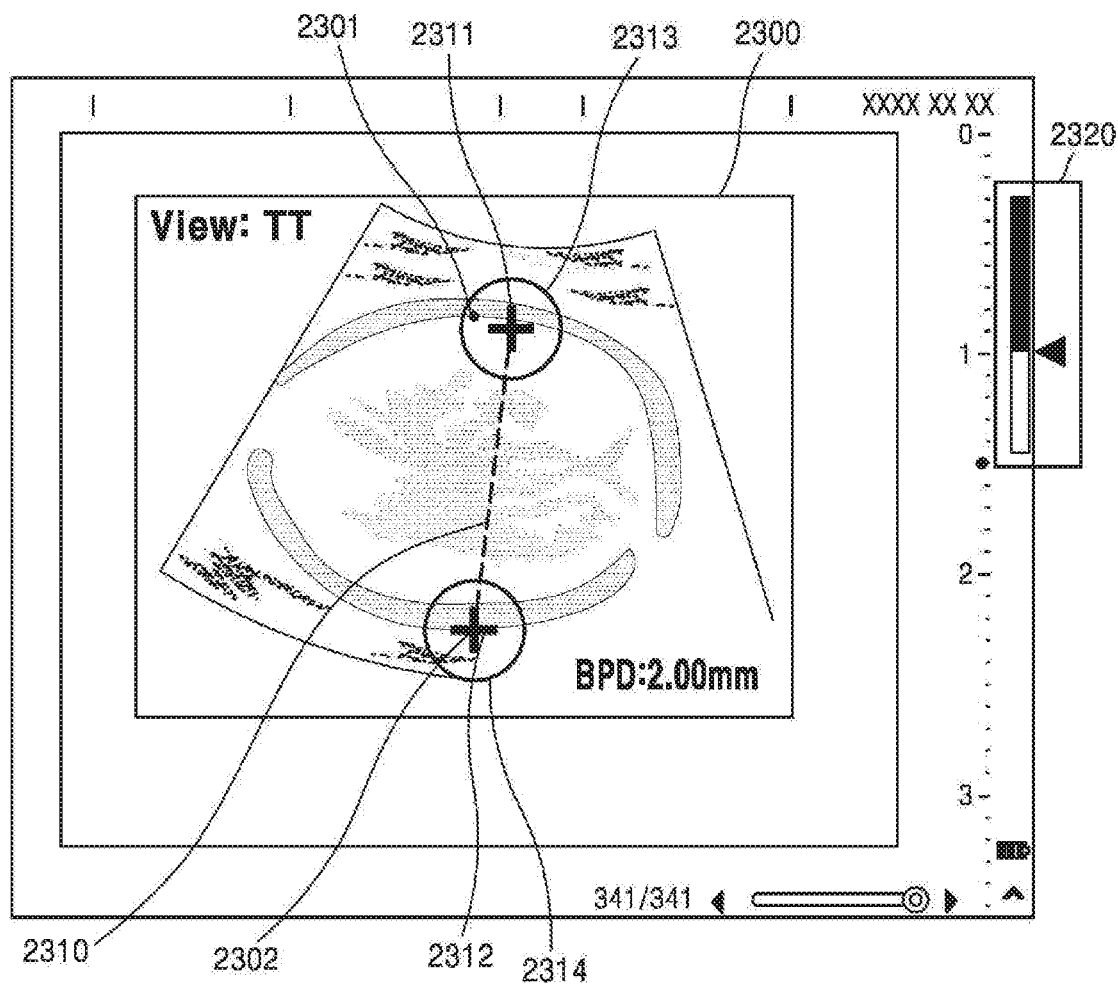
FIGS. 23A, 23B, 23C, and 23D illustrate an operation of displaying a touch recognition region and moving an object to an edge that is automatically detected in a touch recognition region, according to an exemplary embodiment.

Referring to FIG. 23A, the ultrasound apparatus 100 may display, on a screen, an ultrasound image 2300 obtained by capturing an image of a head of a fetus. For example, in order to accurately measure a biparietal diameter (BPD) from the ultrasound image 2300, both ends of a caliper 2310 need to be positioned at a first point 2301 and a second point 2302, respectively, wherein the first point 2301 is positioned inside an upper cranial bone and the second point 2302 is positioned outside a lower cranial bone.

According to an exemplary embodiment, the caliper 2310 may include, at its both ends, a first object 2311 and a second object 2312 that are used as measurement marks. The ultrasound apparatus 100 may display, on the ultrasound image 2300, the first object 2311, the second object 2312, a first touch recognition region 2313 of the first object 2311, and a second touch recognition region 2314 of the second object 2312. For example, the ultrasound apparatus 100 may display a boundary of the first touch recognition region 2313 and a boundary of the second touch recognition region 2314 by using a red solid line. For example, a user may recognize the first touch recognition region 2313 of the first object 2311 and the second touch recognition region 2314 of the second object 2312.

The second object 2312 is positioned exactly at the second point 2302 on the ultrasound image 2300 but the first object 2311 is beyond the first point 2301, thus, the user may move the first object 2311 to the first point 2301 so as to accurately measure the BPD, a result of which may be displayed on the screen. For example, the measurement may be performed based on a measured distance between the first object 2311 and the second object 2312 and a display magnification ratio of the displayed ultrasound image, e.g., a base magnification of the displaying parameters for the underlying ultrasound image.

Figure 23B:
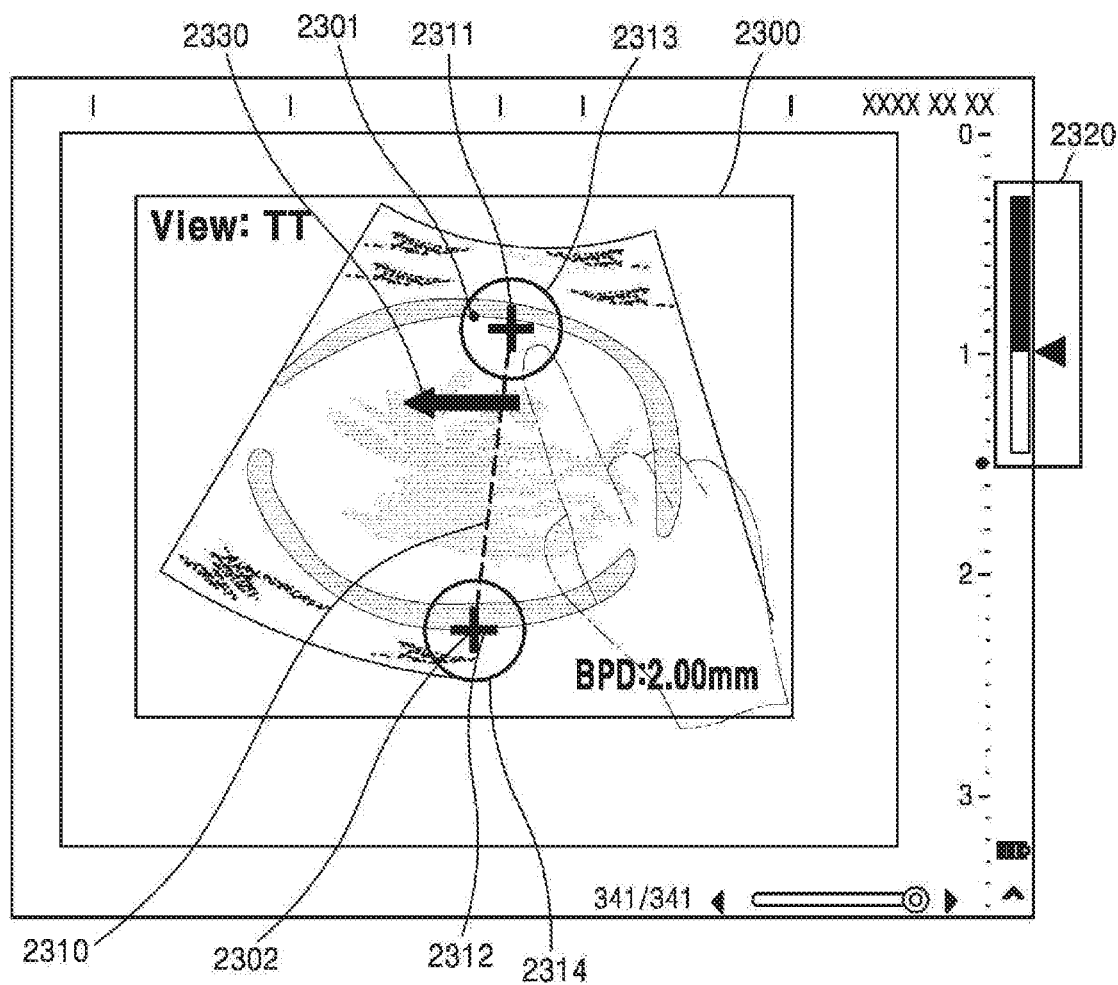

Referring to FIG. 23B, the ultrasound apparatus 100 may receive a touch and drag input 2330 (illustrated by an arrow) for touching and dragging left the first touch recognition region 2313 of the first object 2311. According to the touch and drag input 2330, the ultrasound apparatus 100 may move the first object 2311 and the first touch recognition region 2313 in a left direction.

When the user thinks that the first object 2311 is positioned at the first point 2301, the user may take off a finger from a touch screen. However, it is difficult for the user to exactly locate the first object 2311 at the first point 2301 by the touch and drag input 2330.

Figure 23C:
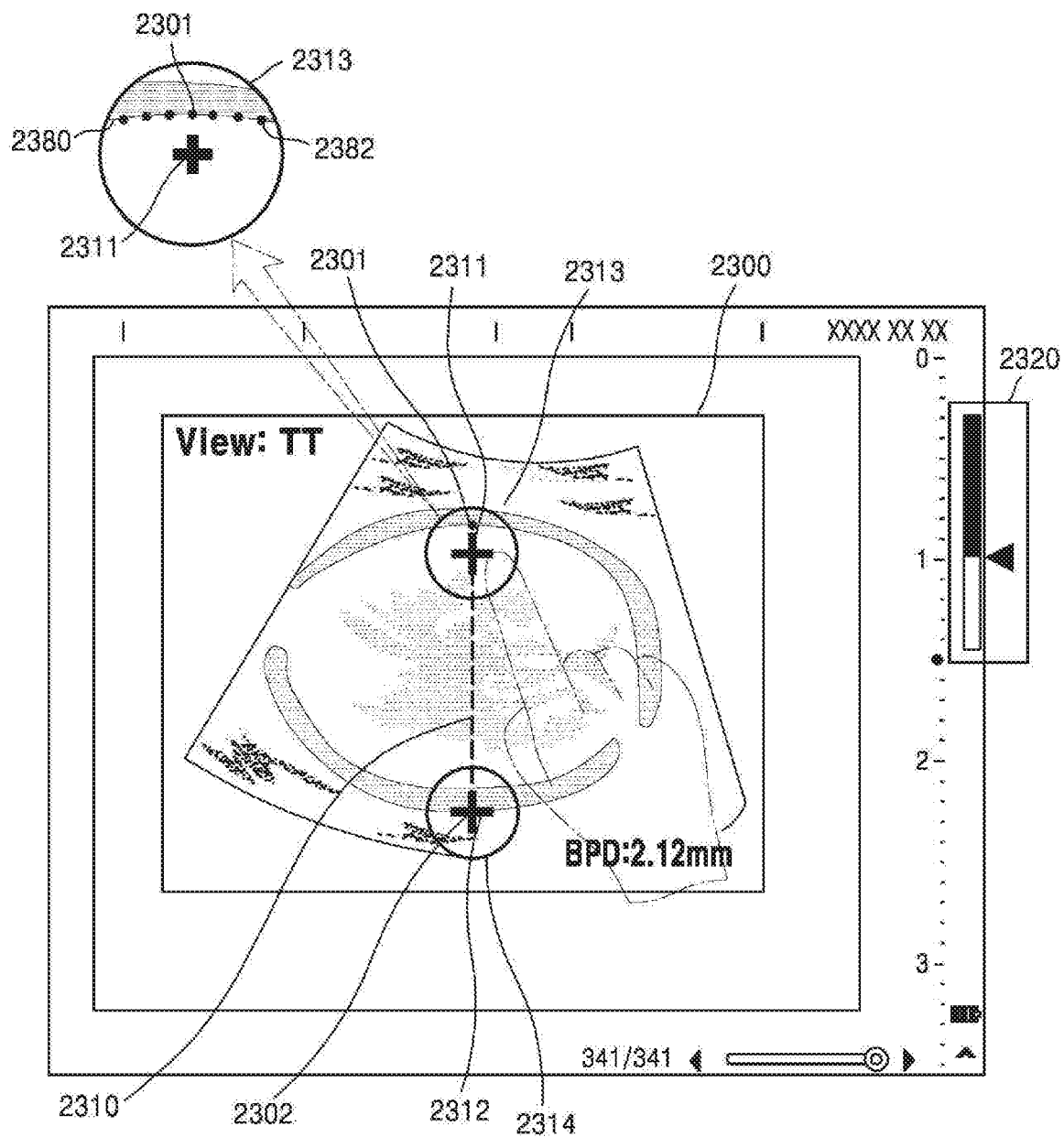

Referring to FIG. 23C, even if the first object 2311 looks positioned at the first point 2301, actually, the first object 2311 is positioned near the first point 2301. According to an exemplary embodiment, the ultrasound apparatus 100 may detect an edge 2380 from the first object 2311. For example, the ultrasound apparatus 100 may detect a partial edge of the upper cranial bone.

The ultrasound apparatus 100 may compare distances between the first object 2311 and points 2382 of the detected edge, and may select, among the points, the first point 2301 that is the closest point to the first object 2311.

Figure 23D:
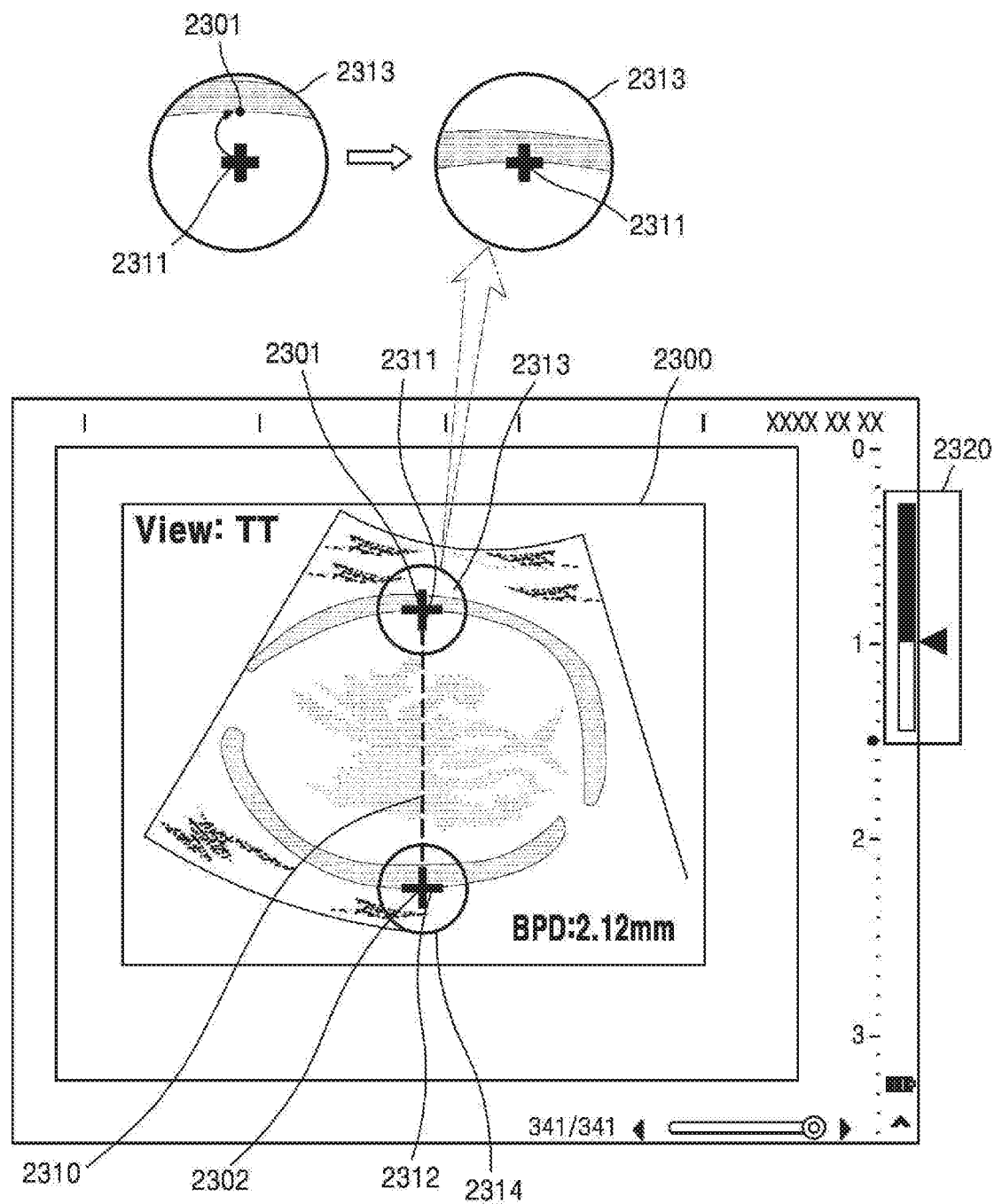

Referring to FIG. 23D, the ultrasound apparatus 100 may move the first object 2311 to the first point 2301 on the detected edge, so that both ends of the caliper 2310 become respectively positioned at the first point 2301 positioned inside the upper cranial bone and the second point 2302 positioned outside the lower cranial bone and the ultrasound apparatus 100 may accurately measure the BPD.

According to an exemplary embodiment, the ultrasound apparatus 100 may provide a user interface for setting an edge detection level. For example, the ultrasound apparatus 100 may display a bar 2320 for adjusting the edge detection level at a side of the ultrasound image 2300.

According to an exemplary embodiment, when the edge detection level is a first level, the ultrasound apparatus 100 may detect an edge of which a gradient value with respect to brightness is equal to or greater than a first threshold value, and when the edge detection level is a second level, the ultrasound apparatus 100 may detect an edge of which a gradient value with respect to brightness is equal to or greater than a second threshold value. Therefore, an edge detected from the ultrasound image 2300 may vary, according to the edge detection level.

Figure 24:
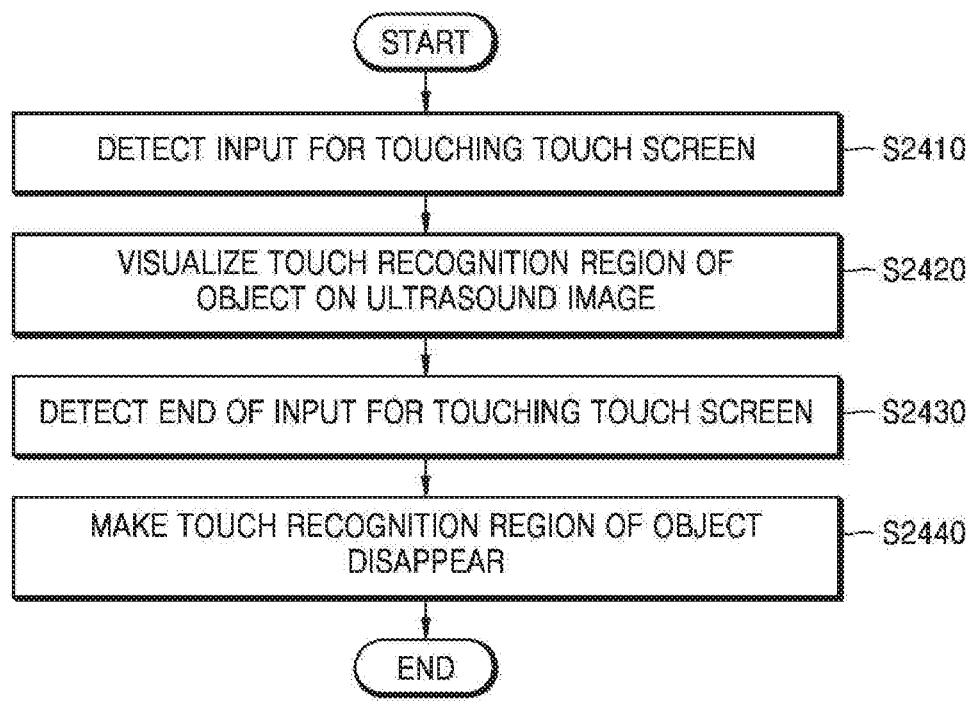
FIG. 24 is a flowchart illustrating a method of visualizing a touch recognition region when a touch input from a user is detected, according to an exemplary embodiment.

FIG. 24 is a flowchart illustrating a method of visualizing a touch recognition region when a touch input from a user is detected, the method being performed by the ultrasound apparatus 100, according to an exemplary embodiment.

In operation S2410, the ultrasound apparatus 100 may detect an input for touching a touch screen. Here, the 'input for touching' may include a case where the user contacts the touch screen and a case where the user approaches the touch screen to the extent that the ultrasound apparatus 100 recognizes the approach as a user input, e.g., a proximity input.

For example, the ultrasound apparatus 100 may detect an input for touching an ultrasound image displayed on the touch screen.

In operation S2420, when the input for touching the touch screen is detected, the ultrasound apparatus 100 may visualize a touch recognition region. For example, when an object used as a measurement mark is displayed on the ultrasound image, the ultrasound apparatus 100 may define a predetermined region around the object as the touch recognition region, and may display a boundary of the touch recognition region by using a line or color.

When a plurality of objects are displayed on the ultrasound image, the ultrasound apparatus 100 may define respective touch recognition regions around respective objects, and may display boundaries of the touch recognition regions by using a line or color.

In operation S2430, the ultrasound apparatus 100 may detect that the input for touching the touch screen has ended. For example, when the finger of the user is absent on the touch screen or distant from the touch screen by at least a predetermined distance, the ultrasound apparatus 100 may detect an occurrence of a touch-end event.

In operation S2440, when the input for touching the touch screen has ended, the ultrasound apparatus 100 may make the touch recognition region disappear. For example, the ultrasound apparatus 100 may remove a color or a boundary line of the touch recognition region or make a color or a boundary line of the touch recognition region be transparent. Alternatively, the ultrasound apparatus 100 may make the touch recognition region be blurred by setting 90% as transparency of the color or the boundary line of the touch recognition region.

Therefore, according to an exemplary embodiment, the touch recognition region is displayed only when the user touches the touch screen, and when the user takes off the finger from the touch screen, a display of the touch recognition region may disappear from the touch screen.

According to an exemplary embodiment, the ultrasound apparatus 100 may display the touch recognition region only for a predetermined time period (e.g., 10 seconds) after a measurement mode starts, and after an elapse of the predetermined time period, the ultrasound apparatus 100 may remove a display of the touch recognition region.

Figure 25:
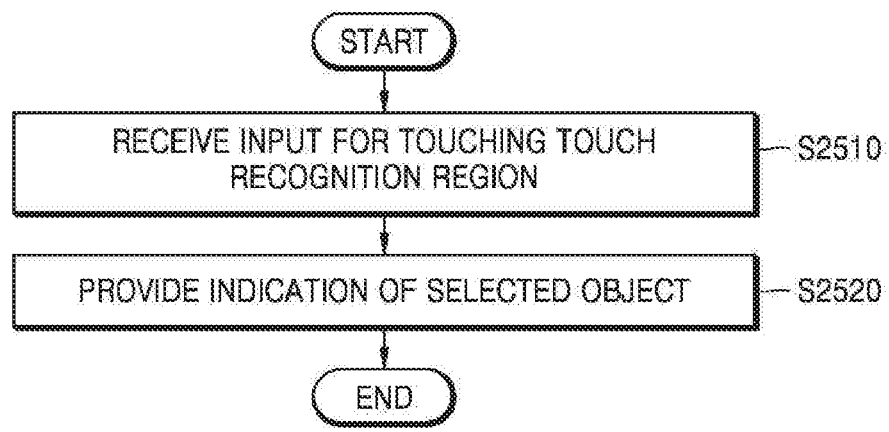
FIG. 25 is a flowchart illustrating a method of providing indication of a selected object, according to an exemplary embodiment.

FIG. 25 is a flowchart illustrating a method of providing indication of a selected object, the method being performed by the ultrasound apparatus 100, according to an exemplary embodiment.

In operation S2510, the ultrasound apparatus 100 may receive an input for touching a touch recognition region. For example, the ultrasound apparatus 100 may receive an input for touching a particular point in or on a boundary of a first touch recognition region corresponding to a first object.

In operation S2520, the ultrasound apparatus 100 may provide indication of a selected object. For example, the ultrasound apparatus 100 may change visual representation of at least one of the first touch recognition region and the first object displayed in the first touch recognition region.

According to an exemplary embodiment, the ultrasound apparatus 100 may change a shape or a color of the selected object. For example, when the ultrasound apparatus 100 receives an input for touching the first touch recognition region among a plurality of touch recognition regions displayed on an ultrasound image, the ultrasound apparatus 100 may determine that the user selected the first object positioned in the first touch recognition region, and may change a shape or a color of the first object.

According to an exemplary embodiment, the ultrasound apparatus 100 may change a shape or a color of a touch recognition region selected by the user to be visually different from a non-selected touch recognition region or a prior-selected touch recognition region. For example, when the ultrasound apparatus 100 receives the input for touching the first touch recognition region among the plurality of touch recognition regions displayed on the ultrasound image, the ultrasound apparatus 100 may change a shape of the first touch recognition region or may change a color of the first touch recognition region. In this case, the user may view the first object and verify that the first object positioned in the first touch recognition region is selected.

According to an exemplary embodiment, the ultrasound apparatus 100 may adjust transparency of a touch recognition region touched by the user or may adjust transparency of an object positioned in the touch recognition region touched by the user. According to an exemplary embodiment, when the user touches a touch recognition region, the ultrasound apparatus 100 may adjust transparency of the touch recognition region, or when the user moves a touch recognition region, the ultrasound apparatus 100 may adjust transparency of the touch recognition region.

According to an exemplary embodiment, the ultrasound apparatus 100 may change a shape (or a color) of only one among the touch recognition region and the object, or may change the shape (or the color) of both the touch recognition region and the object. Alternatively, the ultrasound apparatus 100 may change a size of the touch recognition region or a size of the object.

With reference to FIGS. 26 through 30, an operation of providing indication of a selected object, the operation being performed by the ultrasound apparatus 100, will be described in detail.

Figure 26:
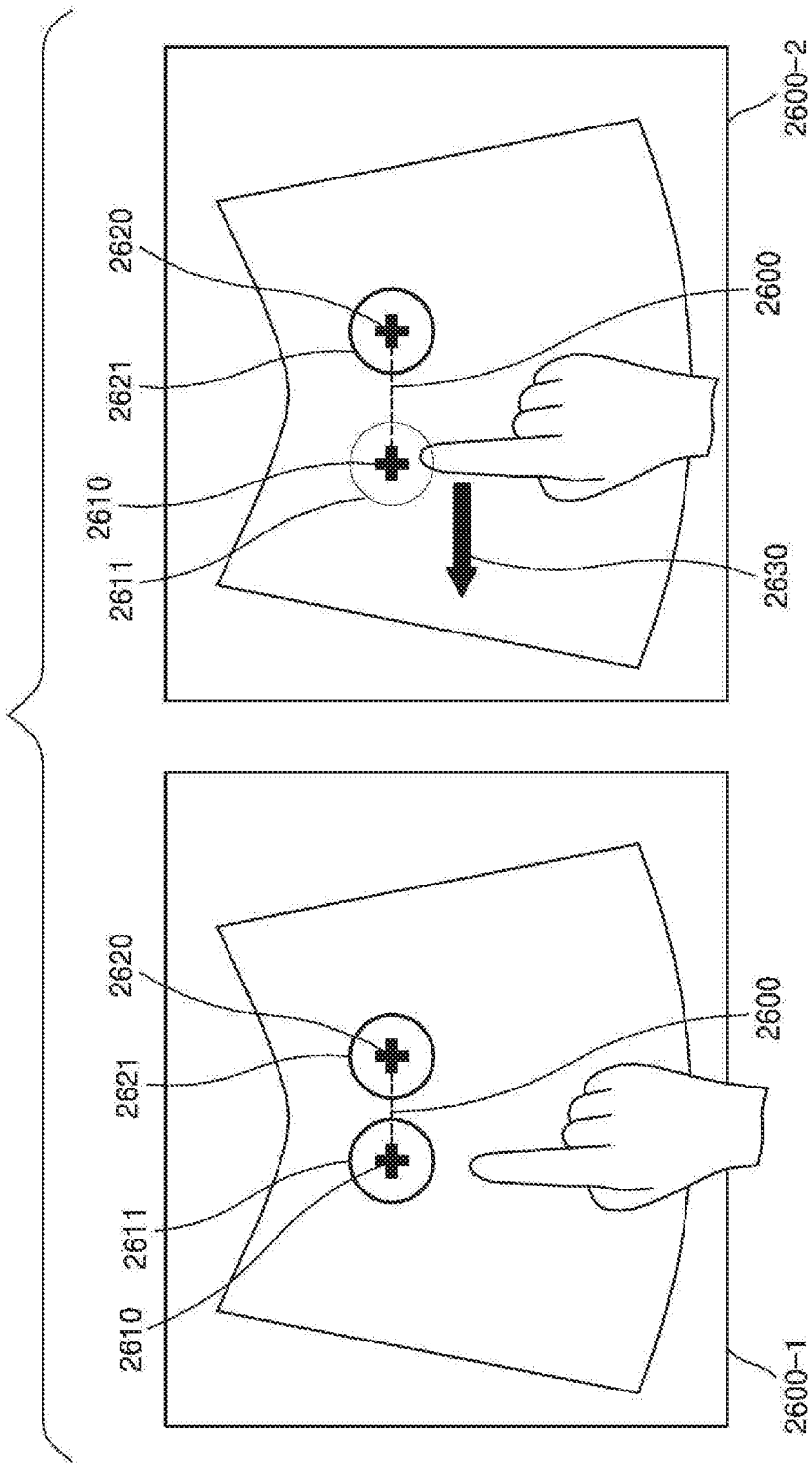
FIG. 26 is a diagram illustrating an operation of adjusting transparency of a touch recognition region, according to an exemplary embodiment.

FIG. 26 is a diagram illustrating an operation of adjusting transparency of a touch recognition region, the operation being performed by the ultrasound apparatus 100, according to an exemplary embodiment.

Referring to a screen 2600-1 of FIG. 26, a caliper 2600 may include, at its both ends, a first object 2610 and a second object 2620 that are used as measurement marks. The ultrasound apparatus 100 may display, on an ultrasound image, the first object 2610, the second object 2620, a first touch recognition region 2611 of the first object 2610, and a second touch recognition region 2621 of the second object 2620. For example, the ultrasound apparatus 100 may display a boundary of the first touch recognition region 2611 and a boundary of the second touch recognition region 2621 by using a red solid line. For example, a user may recognize the first touch recognition region 2611 of the first object 2610 and the second touch recognition region 2621 of the second object 2620.

The ultrasound apparatus 100 may receive an input for touching an inside area (or the boundary) of the first touch recognition region 2611. For example, when the user attempts to change a position of the first object 2610, the user may touch and drag, by using a finger, a particular point that does not obstruct view of the first object 2610 in the first touch recognition region 2611.

Referring to a screen 2600-2 of FIG. 26, when a touch and drag input 2630 with respect to the first touch recognition region 2611 is input, the ultrasound apparatus 100 may change transparency of the first touch recognition region 2611. For example, the ultrasound apparatus 100 may make the opaque first touch recognition region 2611 be translucent. For example, the ultrasound apparatus 100 may change the boundary of the first touch recognition region 2611 to be translucent, the boundary being displayed by using the blue solid line or a different colored line.

For example, when the touch and drag input 2630 with respect to the first touch recognition region 2611 is received, the ultrasound apparatus 100 may change transparency of a color in the first touch recognition region 2611 from 50% to 80%.

Figure 27:
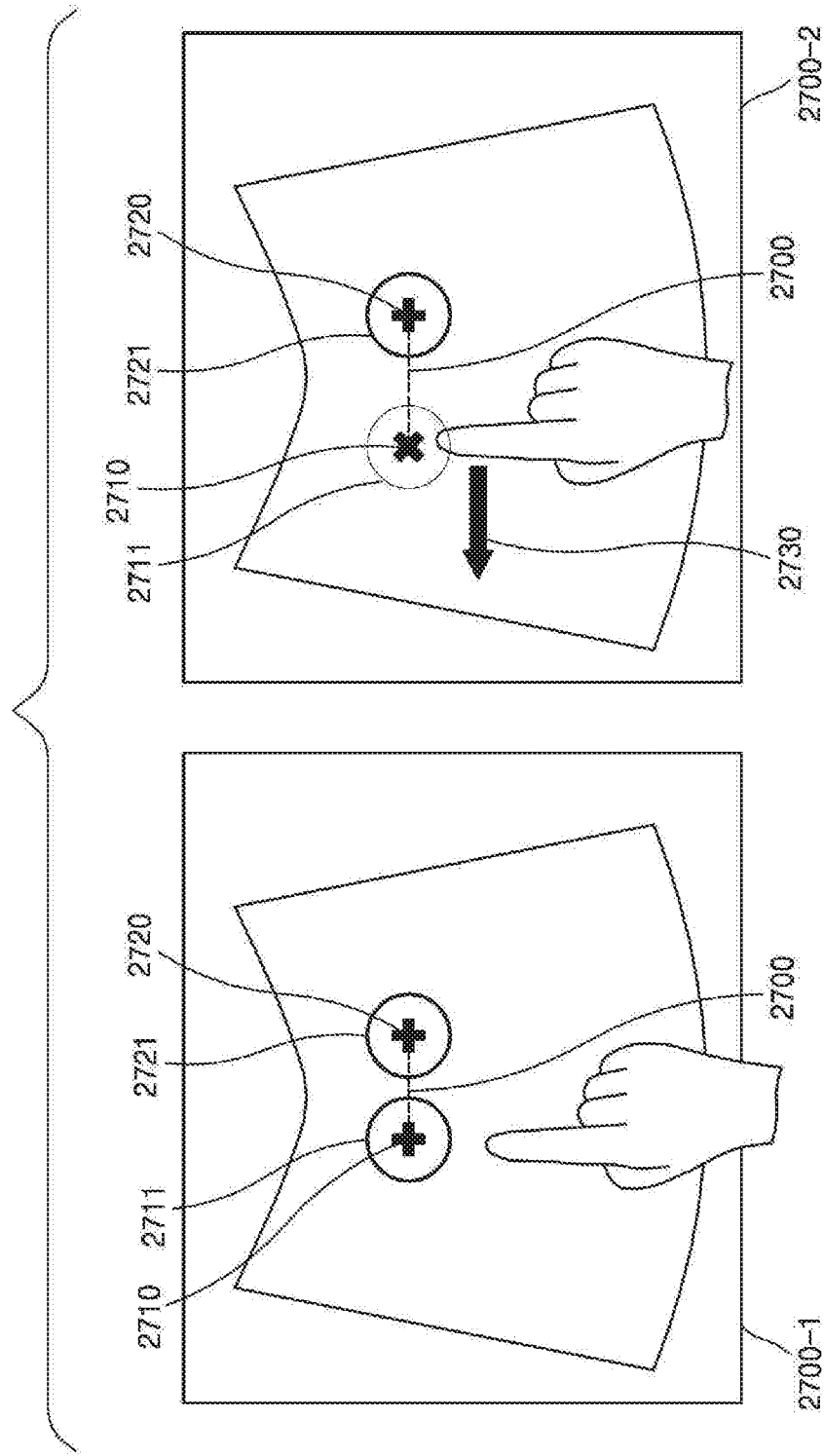
FIGS. 27 and 28 are diagrams for describing an operation of changing a shape of an object, according to an exemplary embodiment.
Figure 28:
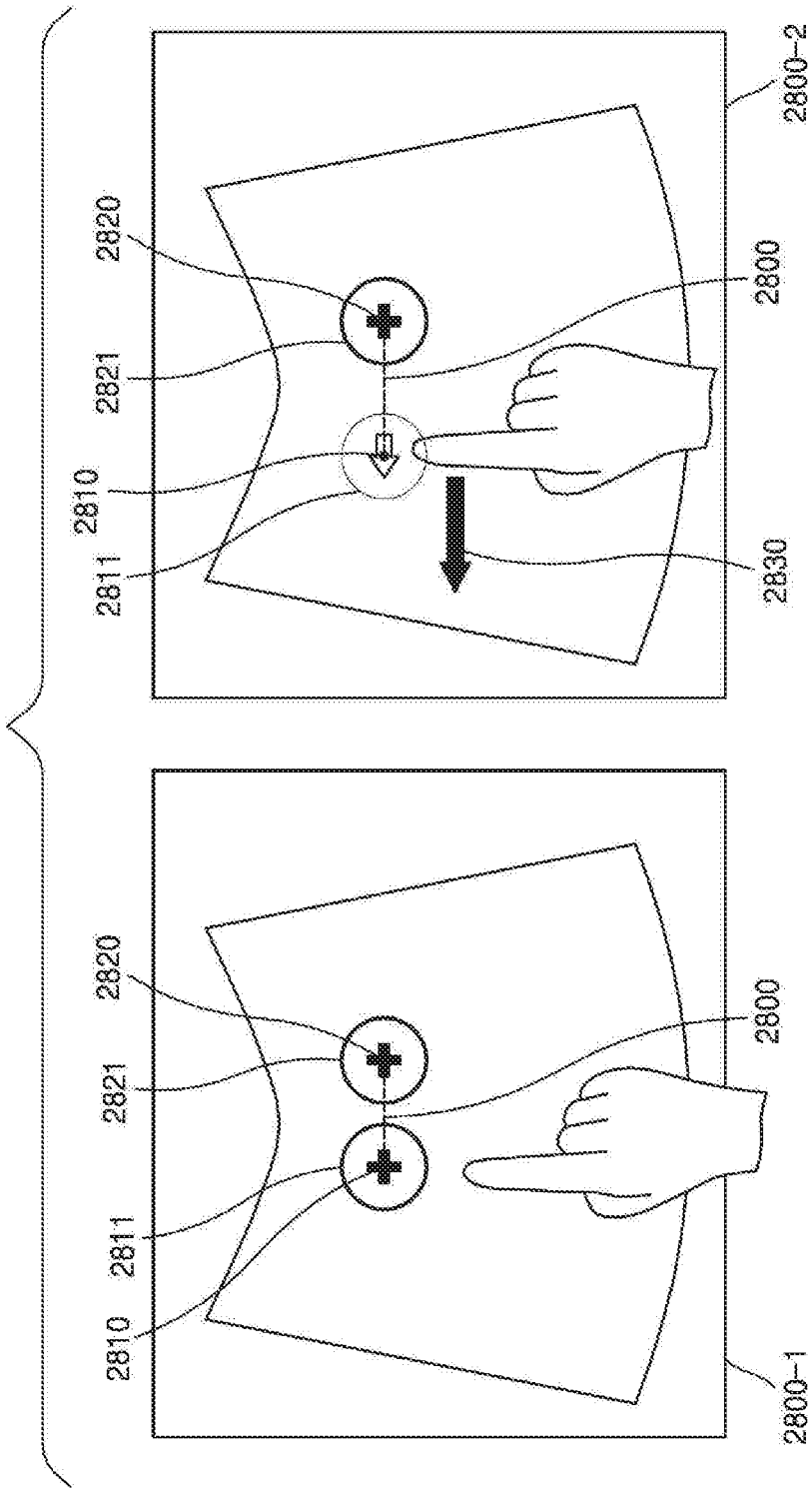

FIGS. 27 and 28 are diagrams for describing an operation of changing a shape of an object, the operation being performed by the ultrasound apparatus 100, according to an exemplary embodiment.

Referring to a screen 2700-1 of FIG. 27, a caliper 2700 may include, at its both ends, a first object 2710 and a second object 2720 that are used as measurement marks. The ultrasound apparatus 100 may display, on an ultrasound image, the first object 2710, the second object 2720, a first touch recognition region 2711 of the first object 2710, and a second touch recognition region 2721 of the second object 2720. For example, each of the first object 2710 and the second object 2720 may have a plus(+)-shape.

Referring to a screen 2700-2 of FIG. 27, the ultrasound apparatus 100 may receive an input for touching an inside area (or a boundary) of the first touch recognition region 2711. For example, when a user attempts to change a position of the first object 2710, the user may touch and drag, by using a finger, a particular point that does not obstruct view of the first object 2710 in the first touch recognition region 2711.

According to an exemplary embodiment, when the ultrasound apparatus 100 receives a touch and drag input 2730 (illustrated by an arrow) with respect to the first touch recognition region 2711 from the user, the ultrasound apparatus 100 may change a shape of the first object 2710. For example, the ultrasound apparatus 100 may change the shape of the first object 2710 from the plus(+)-shape to an X-shape. For example, according to an exemplary embodiment, while the first touch recognition region 2711 and the first object 2710 move by a drag operation, the ultrasound apparatus 100 may remove a display of the first touch recognition region 2711 and the second touch recognition region 2721.

Referring to a screen 2800-1 of FIG. 28, the ultrasound apparatus 100 may display a caliper 2800 including a first object 2810 and a second object 2820 that are used as measurement marks. For example, each of the first object 2810 and the second object 2820 may have a plus(+)-shape.

Referring to a screen 2800-2 of FIG. 28, when the ultrasound apparatus 100 receives a touch and drag input 2830 (illustrated by an arrow) with respect to the first touch recognition region 2811 from a user, the ultrasound apparatus 100 may change a shape of the first object 2810. For example, the ultrasound apparatus 100 may change the shape of the first object 2810 from the plus(+)-shape to an arrow shape. For example, the ultrasound apparatus 100 may change a direction of an arrow, according to a dragging direction. For example, when the user touches and drags the first touch recognition region 2811 in a left direction, the ultrasound apparatus 100 may change the shape of the first object 2810 to an arrow shape pointing in the left direction and then may display the changed shape, and when the user touches and drags the first touch recognition region 2811 in a right direction, the ultrasound apparatus 100 may change the shape of the first object 2810 to an arrow shape pointing in the right direction and then may display the changed shape.

In exemplary embodiments of FIGS. 27 and 28, a shape of the first object 2710 or 2810 is the plus(+)-shape, the X-shape, or the arrow shape. However, the shape of the first object 2710 or 2810 is not limited thereto, and may vary.

Figure 29:
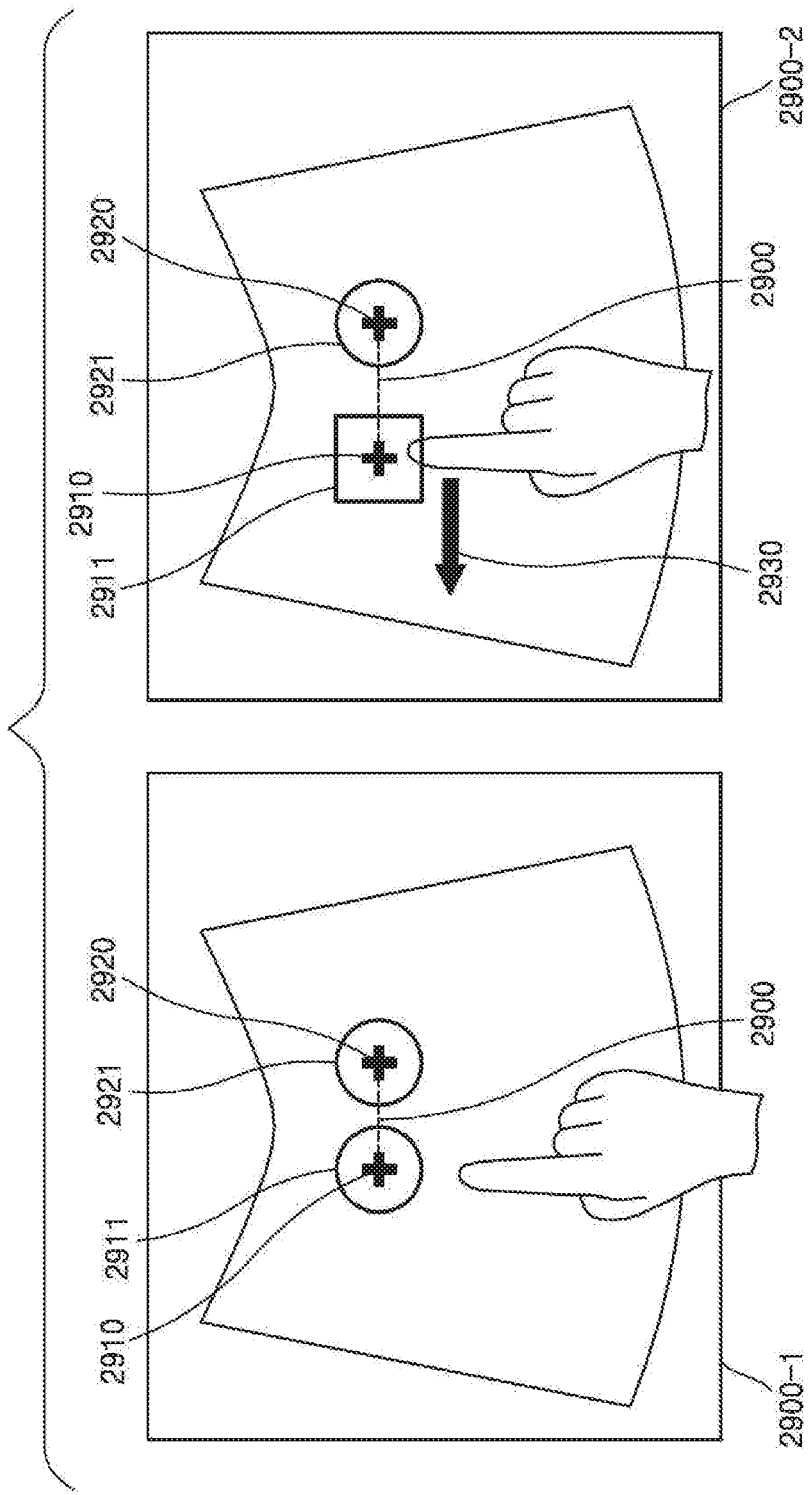
FIG. 29 is a diagram illustrating an operation of changing a shape of a touch recognition region, according to an exemplary embodiment.

FIG. 29 is a diagram illustrating an operation of changing a shape of a touch recognition region, the operation being performed by the ultrasound apparatus 100, according to an exemplary embodiment.

Referring to a screen 2900-1 of FIG. 29, a caliper 2900 may include, at its both ends, a first object 2910 and a second object 2920 that are used as measurement marks. The ultrasound apparatus 100 may display, on an ultrasound image, the first object 2910, the second object 2920, a first touch recognition region 2911 of the first object 2910, and a second touch recognition region 2921 of the second object 2920. For example, each of the first object 2911 and the second object 2921 may have a round shape.

The ultrasound apparatus 100 may receive an input for touching an inside area (or a boundary) of the first touch recognition region 2911. For example, when a user attempts to change a position of the first object 2910, the user may touch and drag, by using a finger, a particular point that does not obstruct view of the first object 2910 in the first touch recognition region 2911.

Referring to a screen 2900-2 of FIG. 29, when the ultrasound apparatus 100 receives a touch and drag input 2930 with respect to the first touch recognition region 2911, the ultrasound apparatus 100 may change a shape of the first object 2911. For example, the ultrasound apparatus 100 may change the shape of the first object 2911 from the round shape to a square shape.

Figure 30:
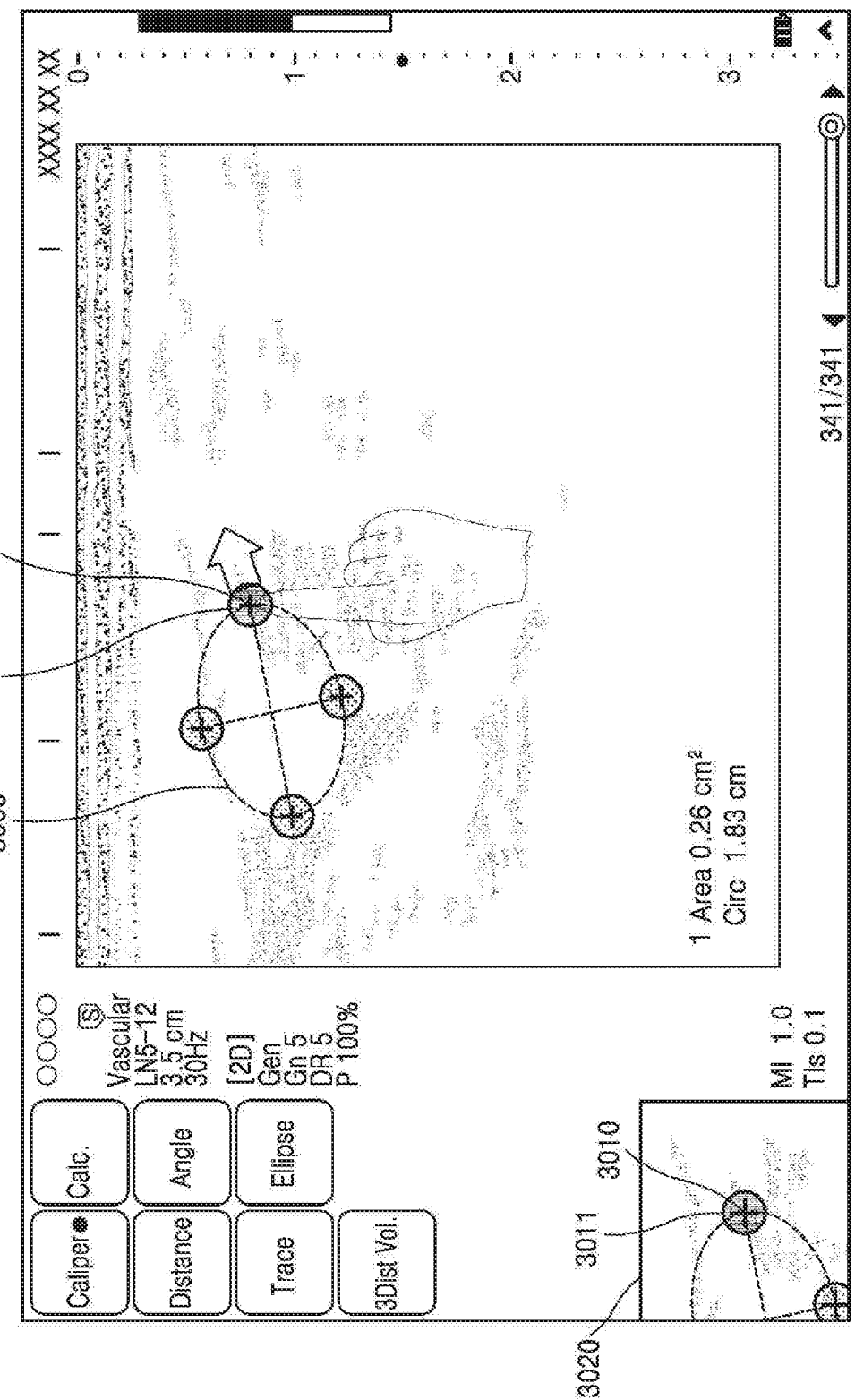
FIG. 30 is a diagram illustrating an operation of changing a color of a touch recognition region, according to an exemplary embodiment.

FIG. 30 is a diagram illustrating an operation of changing a color of a touch recognition region, the operation being performed by the ultrasound apparatus 100, according to an exemplary embodiment.

Referring to FIG. 30, the ultrasound apparatus 100 may display, on an ultrasound image, an oval-shape caliper 3000 for measuring an area or a circumference. The oval-shape caliper 3000 may include four objects each being disposed at both endpoints of the long axis and both endpoints of the short axis, of the oval-shape caliper 3000. For example, the ultrasound apparatus 100 may display touch recognition regions that correspond to the four objects, respectively.

The ultrasound apparatus 100 may receive an input for touching a first touch recognition region 3011 corresponding to a first object 3010 among the four objects. At this time, the ultrasound apparatus 100 may change a color of the first touch recognition region 3011, for example, from a blue color to a yellow color. The touch recognition regions that correspond to the remaining three objects may maintain a blue color. However, the blue and yellow colors are not limiting.

The ultrasound apparatus 100 may generate in real-time a copy image with respect to a point at which a touch input is detected, and may display the copy image in a second region 3020. For example, a predetermined-size copy image may be generated in real-time with respect to a touched point in the first touch recognition region 3011, and may be displayed in the second region 3020.

Figure 31:
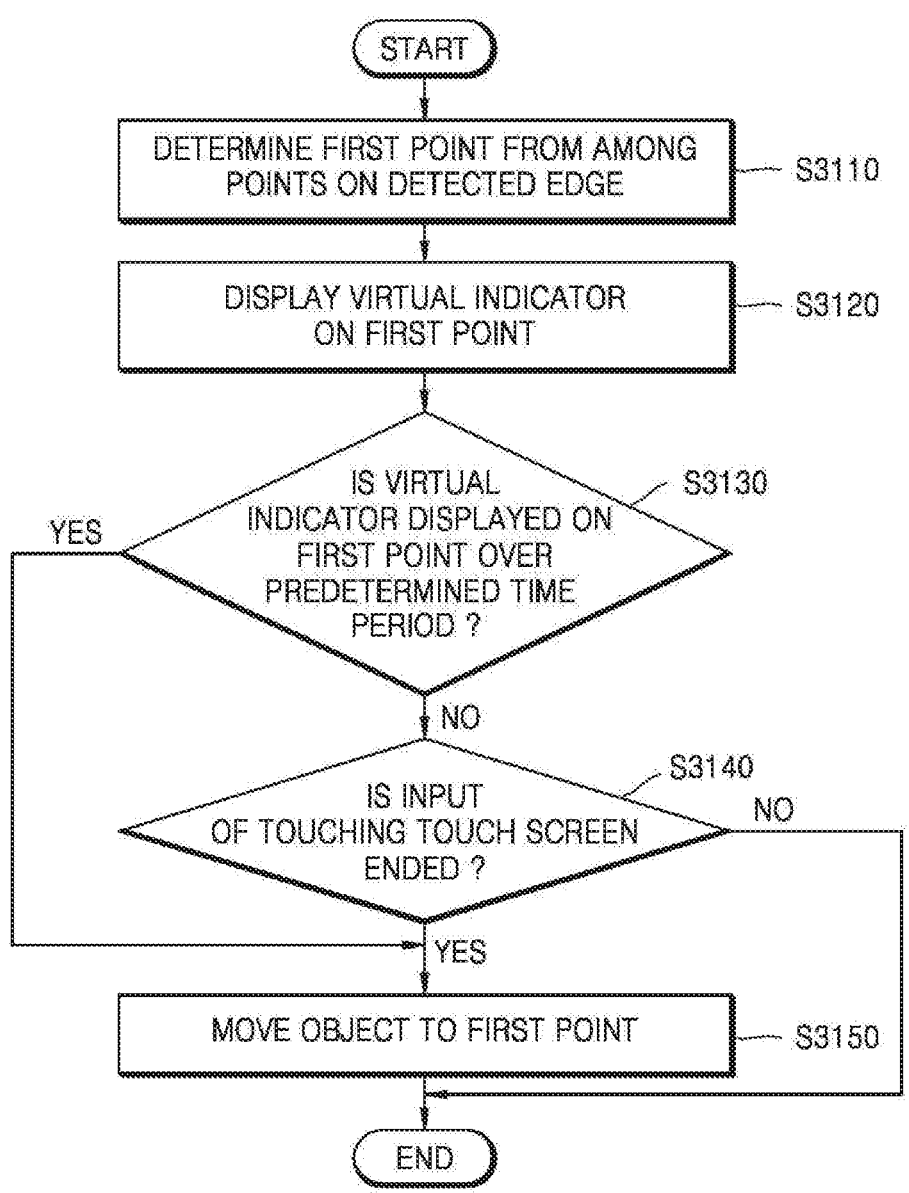
FIG. 31 is a flowchart illustrating a method of providing a virtual indicator, according to an exemplary embodiment.

FIG. 31 is a flowchart illustrating a method of providing a virtual indicator, the method being performed by the ultrasound apparatus 100, according to an exemplary embodiment.

In operation S3110, the ultrasound apparatus 100 may determine a first point among points on a detected edge.

According to an exemplary embodiment, the ultrasound apparatus 100 may determine the first point among the points, based on a plurality of pieces of information regarding distances between an object and the points on the detected edge. For example, the ultrasound apparatus 100 may determine the first point at a shortest distance from the object, among the points on the detected edge.

According to an exemplary embodiment, when a plurality of points are present at a shortest distance from the object, among the points on the detected edge, the ultrasound apparatus 100 may select one of the plurality of points.

In operation S3120, the ultrasound apparatus 100 may display a virtual indicator on the first point. Here, the virtual indicator may be an image that displays in advance a position (e.g., the first point) to which the object is to move.

According to an exemplary embodiment, the virtual indicator may have a shape and size that are equal to those of the object. For example, if the object has a plus(+)-shape, the virtual indicator may also have a plus(+)-shape. For example, according to an exemplary embodiment, the virtual indicator may be different from the object in a color or transparency. For example, the object has a blue color, while the virtual indicator has a sky-blue color. Alternatively, transparency of the object is 0%, while transparency of the virtual indicator is 70%.

According to an exemplary embodiment, the virtual indicator may have a shape (or a size) that is different from that of the object. For example, the object has the plus(+)-shape, while the virtual indicator has an X-shape. Alternatively, the size of the virtual indicator may be ⅔ of a size of the object. When the object is displayed by using a solid line, the virtual indicator may be displayed by using a dotted line, a dashed dotted line, etc.

In operation S3130, the ultrasound apparatus 100 may determine whether the virtual indicator is displayed on the first point over a predetermined time period. For example, the ultrasound apparatus 100 may determine whether the virtual indicator is displayed on the first point over 3 seconds.

When the virtual indicator is displayed on the first point over the predetermined time period (e.g., 3 seconds), the ultrasound apparatus 100 may move the object to the first point (operation S3150).

In operation S3140, when the virtual indicator is not displayed on the first point over the predetermined time period, the ultrasound apparatus 100 may determine whether an input of touching a touch screen has ended. For example, when a finger (or an electronic pen) is distant from the touch screen to the extent that the ultrasound apparatus 100 cannot recognize the finger as a user input, the ultrasound apparatus 100 may determine that the input of touching the touch screen has ended.

In operation S3150, when the input of touching the touch screen has ended while the virtual indicator is displayed on the first point, the ultrasound apparatus 100 may move the object to the first point.

According to an exemplary embodiment, when the object is moved to the first point, the object and the virtual indicator overlap with each other, therefore, the ultrasound apparatus 100 no longer displays the virtual indicator.

By checking a position of the virtual indicator, the user may correctly expect where the object is moved to. Therefore, even if the user does not accurately move the object onto an edge via a touch and drag input, the user may allow the object to be positioned at a particular point (a user-desired point) on the edge, by checking the position of the virtual indicator. Hereinafter, with reference to FIGS. 32A through 34C, the virtual indicator will now be described in detail.

Figure 32A:
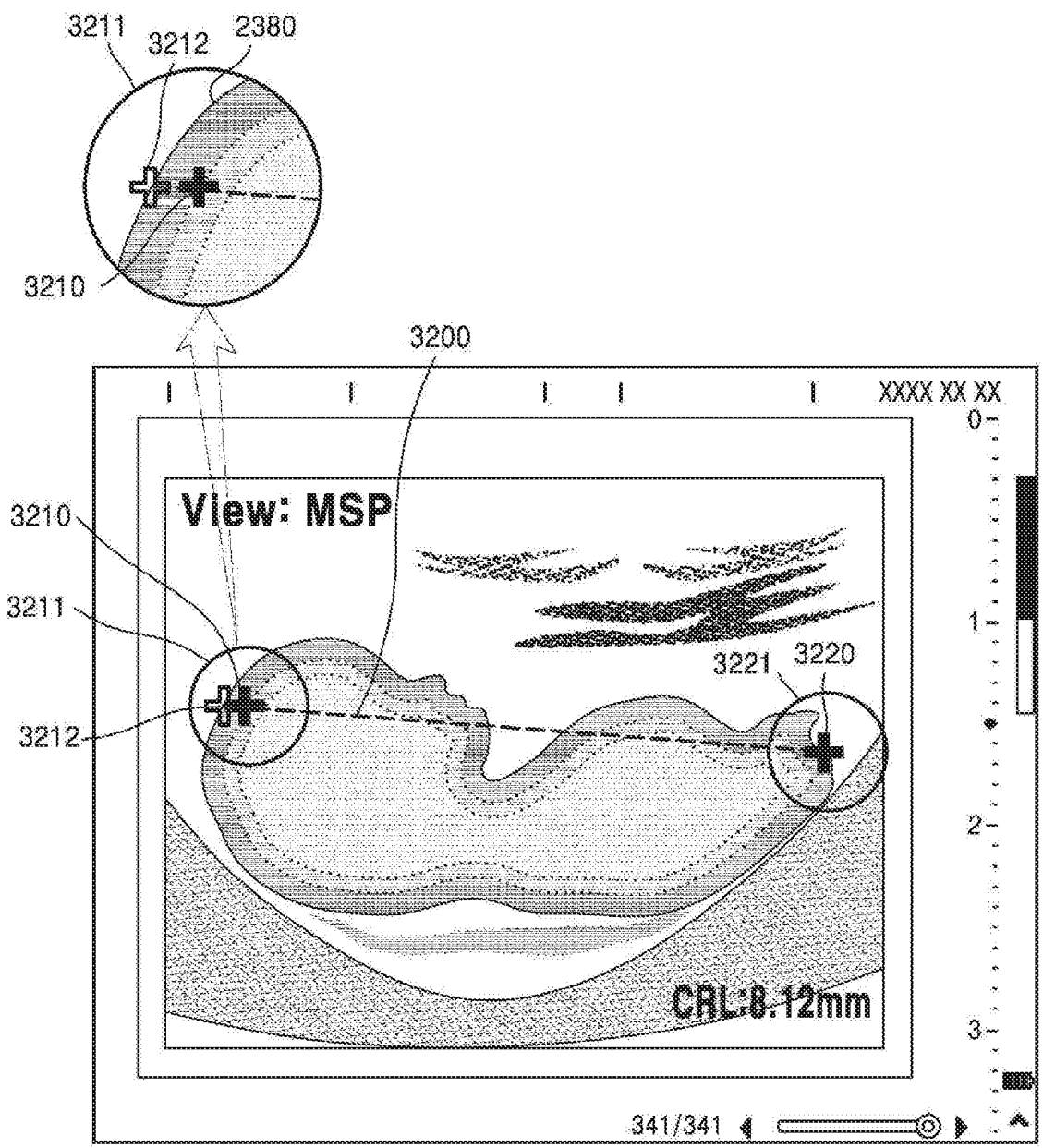
FIGS. 32A and 32B are diagrams illustrating an operation of providing a virtual indicator, according to an exemplary embodiment.
Figure 32B:
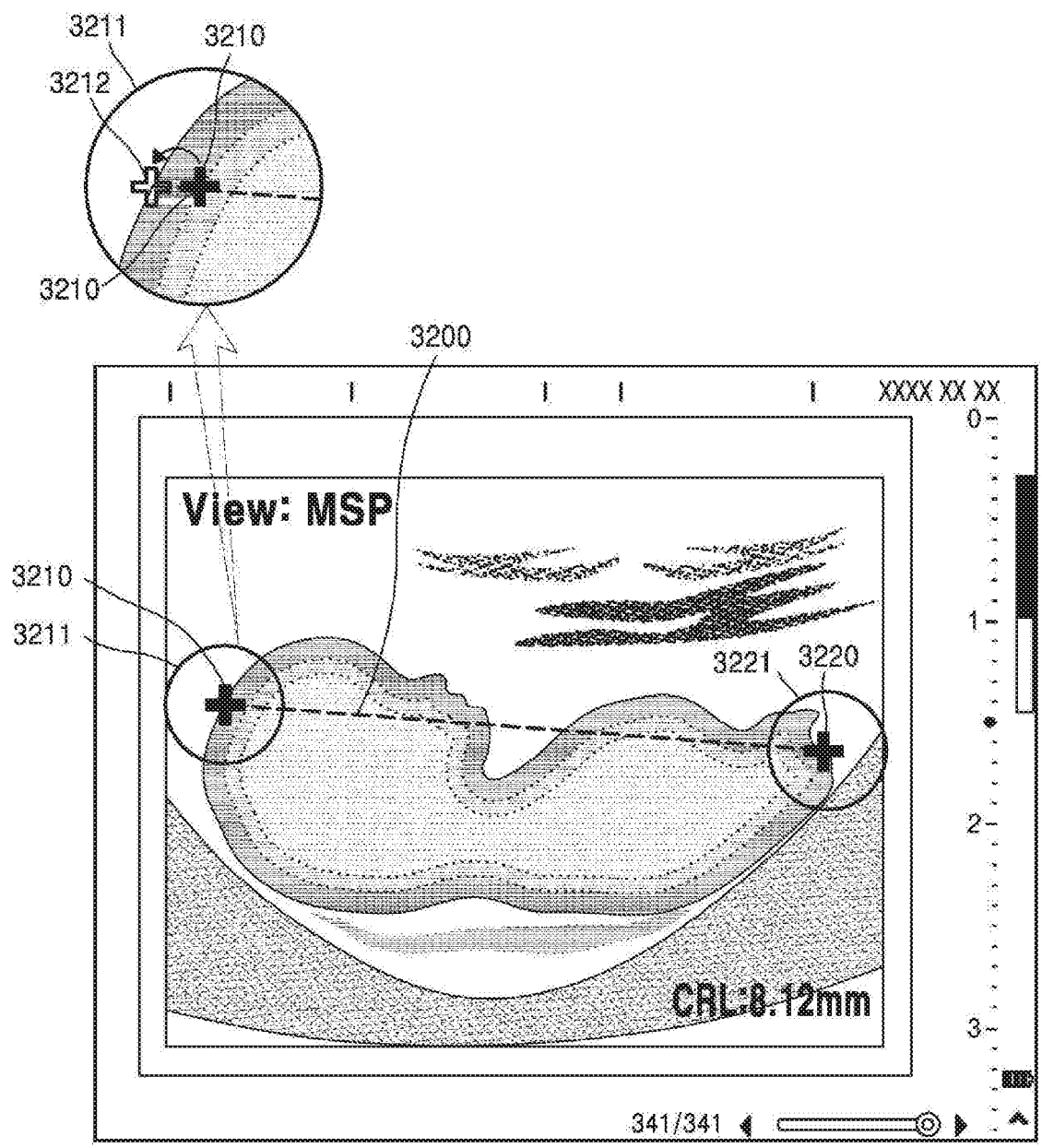

FIGS. 32A and 32B are diagrams illustrating an operation of providing a virtual indicator, the operation being performed by the ultrasound apparatus 100, according to an exemplary embodiment.

Referring to FIG. 32A, the ultrasound apparatus 100 may display an ultrasound image of a fetus on a screen. For example, a caliper 3200 for measuring crown-rump length (CRL) of the fetus may be displayed on the ultrasound image. The caliper 3200 may include, at its both ends, a first object 3210 and a second object 3220 that are used as measurement marks. The ultrasound apparatus 100 may display, on the ultrasound image, the first object 3210, the second object 3220, a first touch recognition region 3211 of the first object 3210, and a second touch recognition region 3221 of the second object 3220.

The second object 3220 is positioned near the buttocks of the fetus but the first object 3210 is not exactly positioned at the head, thus, a user may adjust a position of the first object 3210.

For example, the user may touch and drag the first touch recognition region 3211 in a left direction. The ultrasound apparatus 100 detect an edge in an ultrasound image region corresponding to the first touch recognition region 3211, compare distances between points of the detected edge and the first object 3210, and select, among the points, a first point that is the closest point to the first object 3210. The ultrasound apparatus 100 may display a virtual indicator 3212 on the first point. For example, a shape of the virtual indicator 3212 may be similar to that of the first object 3210.

In this case, the ultrasound apparatus 100 may detect an end of a touch input, and may move the first object 3210 to the first point on which the virtual indicator 3212 is positioned so that a user may observe a "magnetic" effect. The ultrasound apparatus 100 may measure the CRL (e.g., 8.12 mm), based on a distance between the first object 3210 and the second object 3220 and may display a result on a screen.

Figure 33A:
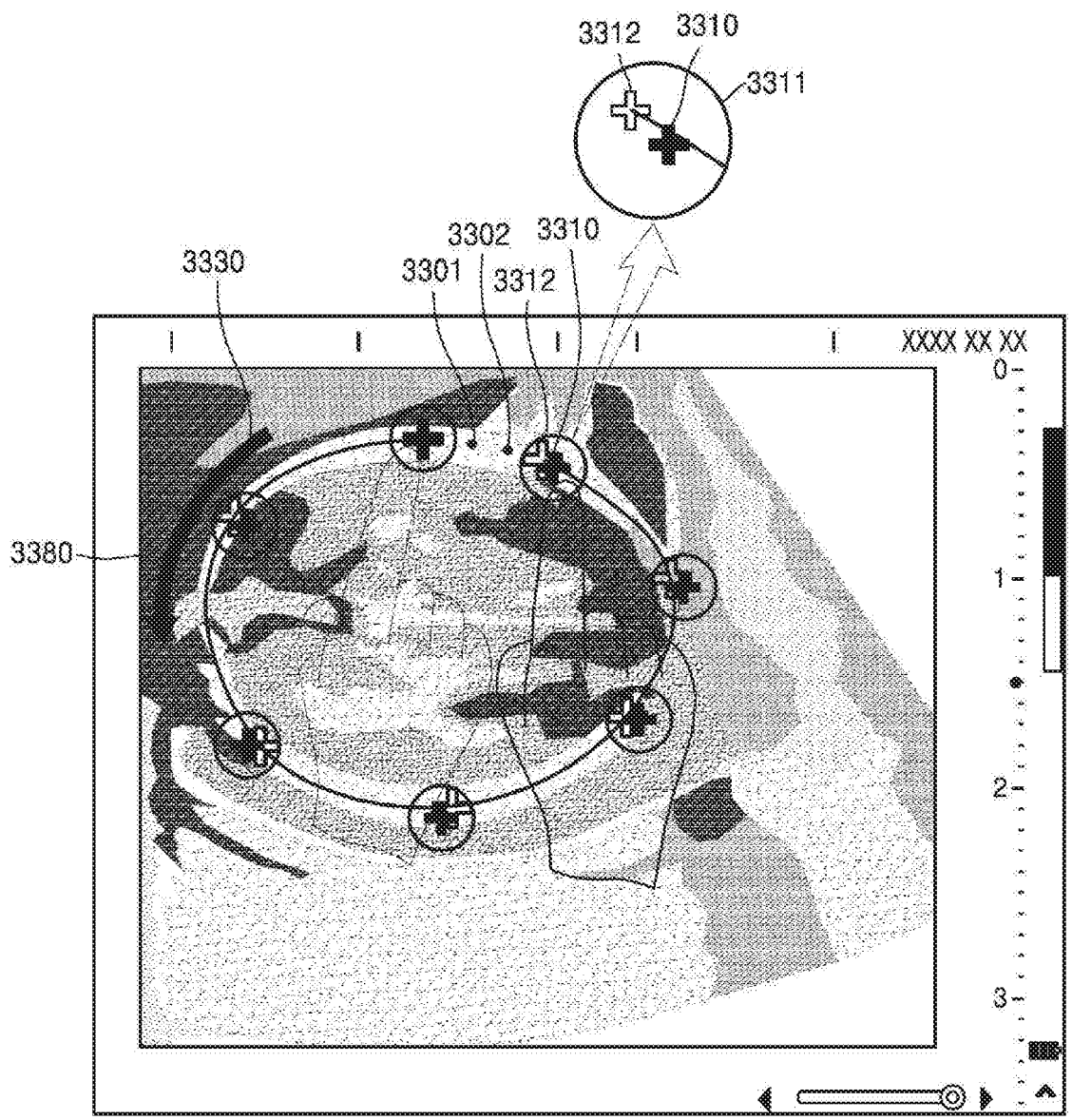
FIGS. 33A and 33B are diagrams illustrating an operation of measuring a size of an interest area by using a trace tool, according to an exemplary embodiment.
Figure 33B:
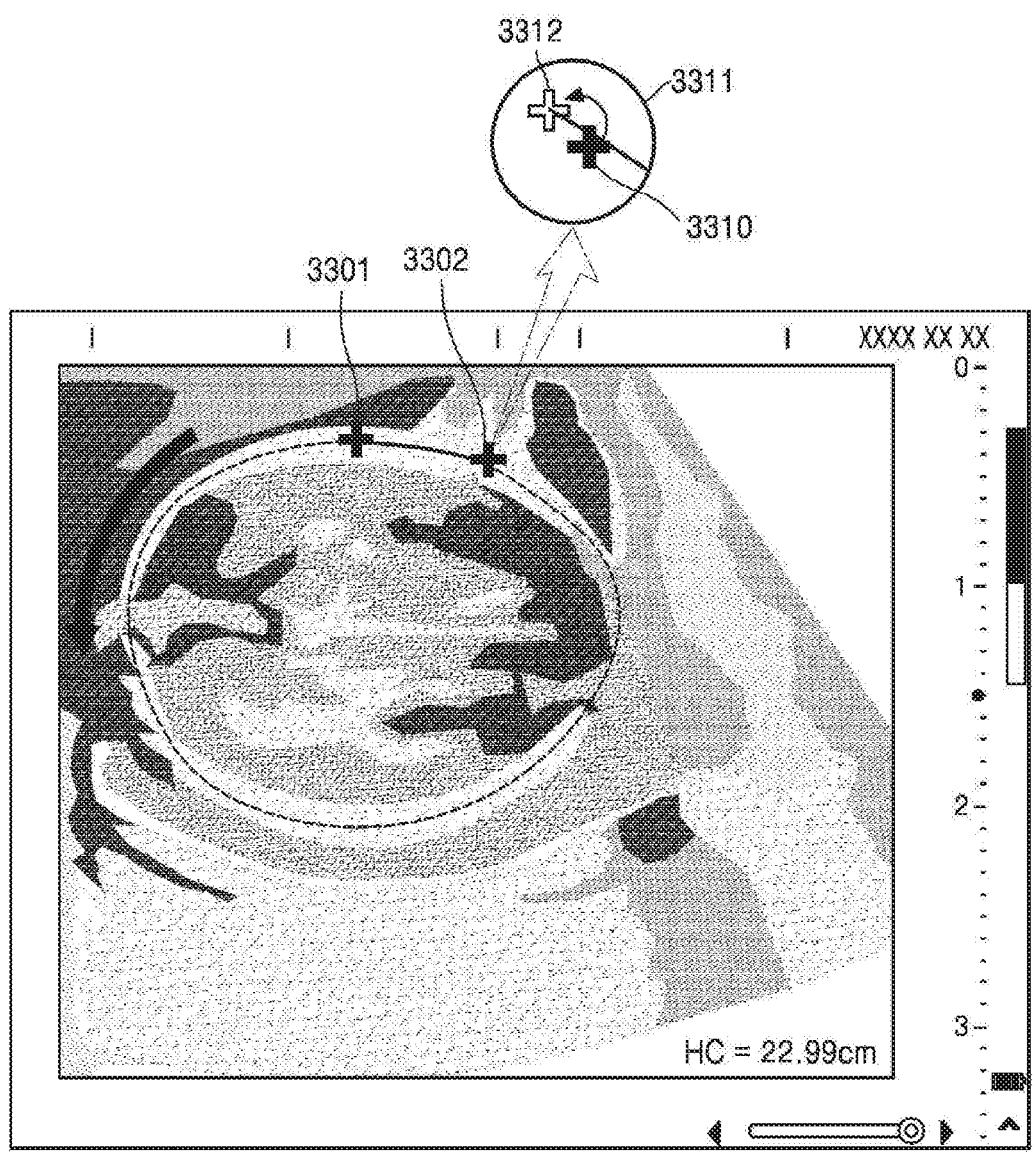

FIGS. 33A and 33B are diagrams illustrating an operation of measuring a size of an interest area by using a trace tool, the operation being performed by the ultrasound apparatus 100, according to an exemplary embodiment.

Referring to FIG. 33A, the ultrasound apparatus 100 may display an ultrasound image including a fetus. The ultrasound apparatus 100 may provide the trace tool for measuring a head circumference of the fetus.

A user may draw, by using a finger, a curved line from a first point 3301 to a second point 3302 around the head circumference of the fetus. However, it is difficult for the user to accurately draw the line around the head circumference of the fetus.

Therefore, the ultrasound apparatus 100 may display a first object 3310 and a first touch recognition region 3311 of the first object 3310 on the ultrasound image. For example, the user may draw, by using a finger, a curved line 3330 around the head circumference of the fetus while the user touches the first touch recognition region 3311.

The ultrasound apparatus 100 may detect edges in the first touch recognition region 3311 along a movement path of the first touch recognition region 3311. The ultrasound apparatus 100 may compare distances between the first object 3310 and points of the detected edges, and may select points that are the closest points to the first object 3310, while the first object 3310 is being dragged in a direction 3380. For example, the ultrasound apparatus 100 may display a virtual indicator 3312 on the selected points.

When the user checks that the virtual indicator 3312 is positioned on the second point 3302, the user may take off the finger from a touch screen. In this case, the ultrasound apparatus 100 may move the first object 3310 to the second point 3302.

Referring to FIG. 33B, the ultrasound apparatus 100 may detect an end of a touch input, and may automatically draw a curved line around the points on which the virtual indicator 3312 was positioned. The ultrasound apparatus 100 may automatically connect the first object 3310 to the second point 3302, and may measure the head circumference of the fetus.

Figure 34A:
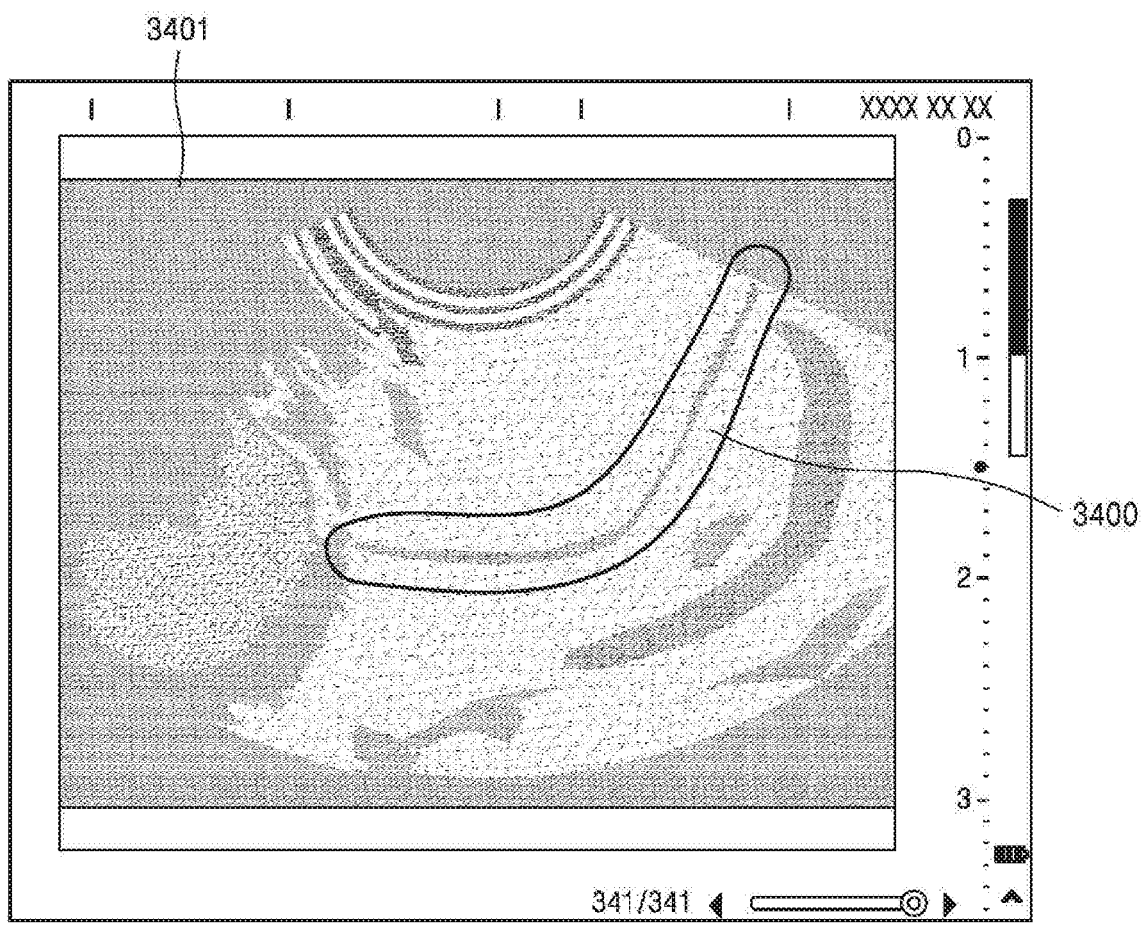
FIGS. 34A, 34B, and 34C are diagrams illustrating an operation of measuring a length, according to an exemplary embodiment.
Figure 34B:
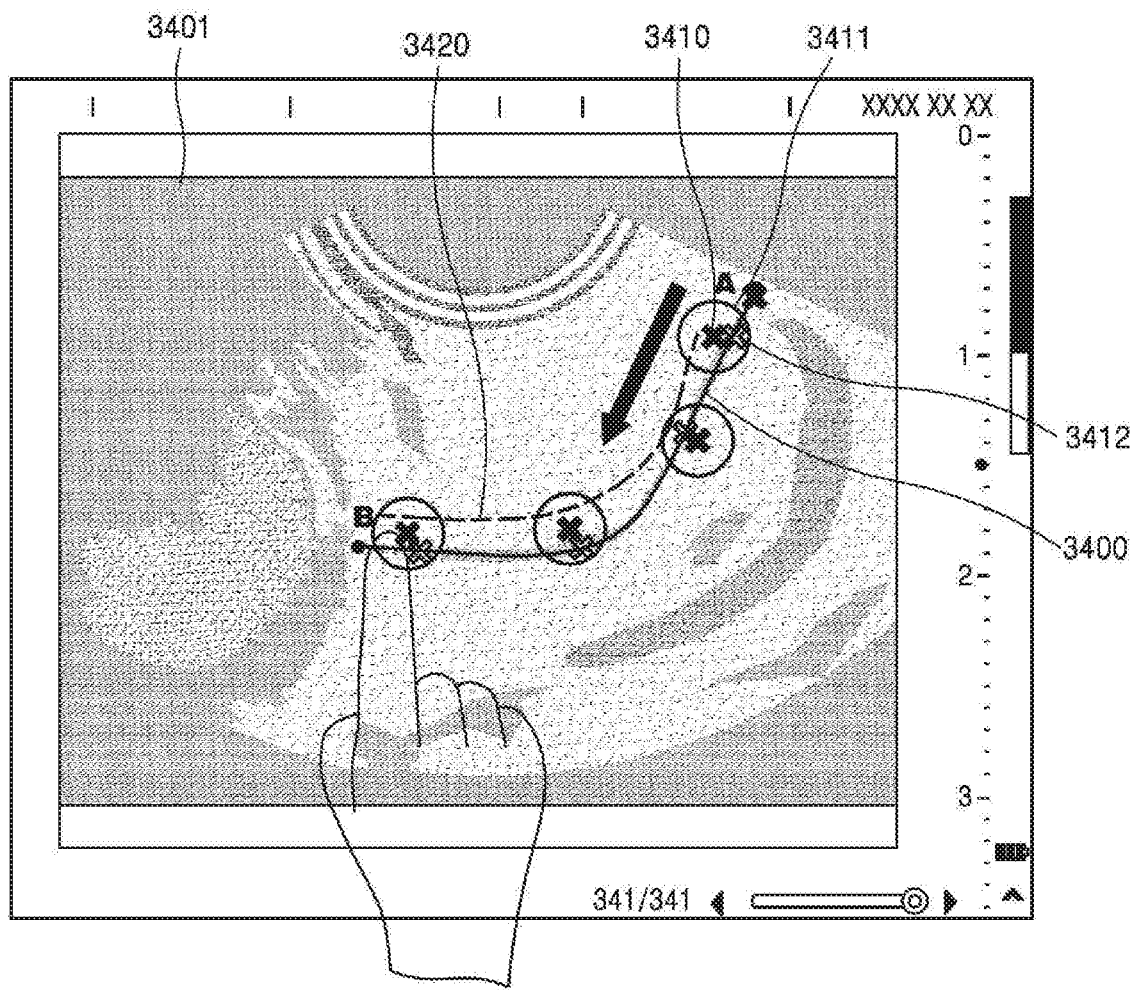
Figure 34C:
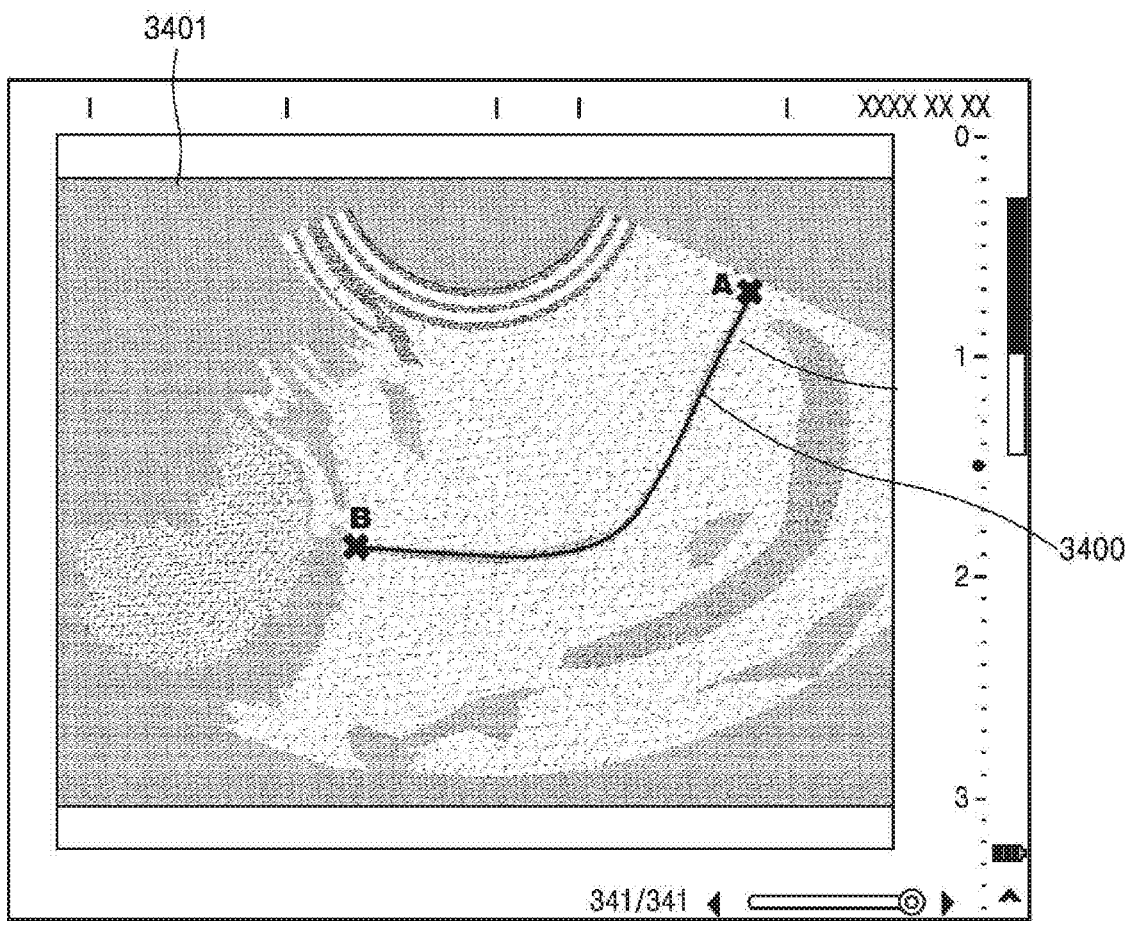

FIGS. 34A through 34C are diagrams illustrating an operation of measuring a length, the operation being performed by the ultrasound apparatus 100, according to an exemplary embodiment.

Referring to FIG. 34A, the ultrasound apparatus 100 may display an ultrasound image 3401 including a cervix 3400 on a screen. For example, a user may want to measure a length of the cervix 3400 on the ultrasound image 3401. Since the cervix 3400 is curved, the user has to measure a length of a curved line.

Referring to FIG. 34B, the ultrasound apparatus 100 may display an object 3410 for measuring a length of an interest target (e.g., the cervix 3400), and a touch recognition region 3411 of the object 3410. For example, the user may touch the touch recognition region 3411 and may draw a line 3420, from about a point A to about a point B, along the cervix 3400 by using a finger.

The ultrasound apparatus 100 may detect edges in the touch recognition region 3411 along a movement path of the touch recognition region 3411. The ultrasound apparatus 100 may compare distances between the object 3410 and points of the detected edges, and may select points that are the closest points to the object 3410. The ultrasound apparatus 100 may display a virtual indicator 3412 on each of the selected points.

Referring to FIG. 34C, the ultrasound apparatus 100 may detect an end of a touch input, and may generate a line (e.g., a line that connects A to B) along the points on which the virtual indicator 3412 was positioned. The ultrasound apparatus 100 may measure a length of the line. For example, the length of the line may correspond to a length of the cervix 3400.

Figure 35:
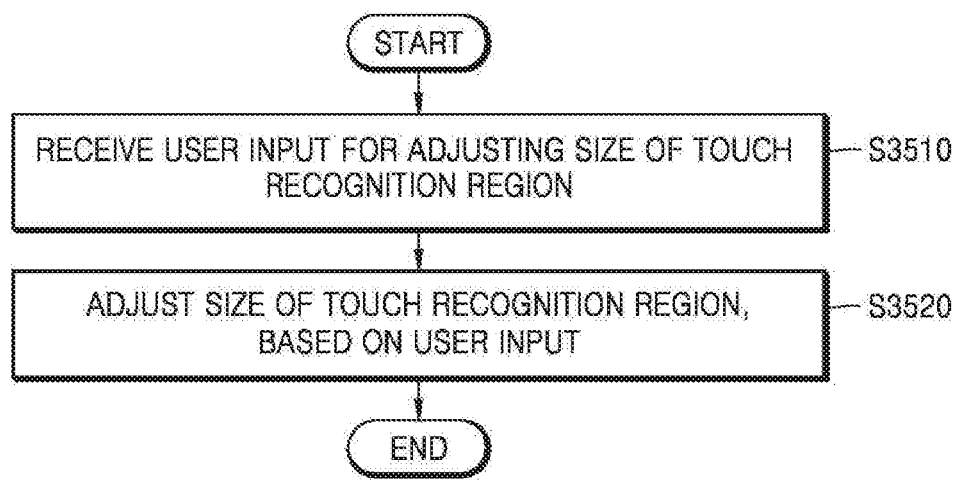
FIG. 35 is a flowchart illustrating a method of adjusting a size of a touch recognition region, according to an exemplary embodiment.

FIG. 35 is a flowchart illustrating a method of adjusting a size of a touch recognition region, the method being performed by the ultrasound apparatus 100, according to an exemplary embodiment.

In operation S3510, the ultrasound apparatus 100 may receive a user input for adjusting the size of the touch recognition region.

For example, the ultrasound apparatus 100 may receive an input of manipulating one or more hardware buttons of a control panel or an input of controlling one or more of software buttons displayed on a screen, for example GUIs, to adjust the size of the touch recognition region. The ultrasound apparatus 100 may provide a GUI for adjusting the size of the touch recognition region, and may receive an input for adjusting the size of the touch recognition region via the GUI. As another example, the ultrasound apparatus 100 may provide a GUI for adjusting the size of the touch recognition region overlaid on the touch recognition region, and may receive an input for adjusting the size of the touch recognition region in the touch recognition region itself or on a boundary thereof. The ultrasound apparatus 100 may receive a voice input or motion input for adjusting the size of the touch recognition region, but a type of the input is not limited thereto.

In operation S3520, the ultrasound apparatus 100 may adjust the size of the touch recognition region, based on a user input. For example, the ultrasound apparatus 100 may decrease or increase the size of the touch recognition region.

According to an exemplary embodiment, the ultrasound apparatus 100 may automatically adjust the size of the touch recognition region. For example, when a distance between detected edges is less than a first threshold value, or the number of detected edges is greater than a second threshold value, the ultrasound apparatus 100 may automatically decrease the touch recognition region. On the other hand, when the distance between the detected edges is greater than a third threshold value, or the number of detected edges is less than a fourth threshold value, the ultrasound apparatus 100 may automatically increase the touch recognition region.

FIG. 36 is a diagram illustrating an operation of adjusting a size of a touch recognition region, the operation being performed by the ultrasound apparatus 100, according to an exemplary embodiment.

Referring to a screen 3600-1 of FIG. 36, a caliper 3600 may include, at its both ends, a first object 3610 and a second object 3620 that are used as measurement marks. The ultrasound apparatus 100 may display, on an ultrasound image, the first object 3610, the second object 3620, a first touch recognition region 3611 of the first object 3610, and a second touch recognition region 3621 of the second object 3620.

A user may check a size of the first touch recognition region 3611 and a size of the second touch recognition region 3621. For example, when the user wants to minutely detect an edge, the user may decrease the sizes of the first touch recognition region 3611 and the second touch recognition region 3621 by using a button 3630 on a UI 3640. For example, the user may turn the button 3630 in a counter-clockwise direction.

Referring to a screen 3600-2 of FIG. 36, the ultrasound apparatus 100 may receive an input for decreasing (or increasing) the sizes of the first touch recognition region 3611 and the second touch recognition region 3621 via the button 3630. The ultrasound apparatus 100 may decrease the sizes of the first touch recognition region 3611 and the second touch recognition region 3621 and may display the first touch recognition region 3611 and the second touch recognition region 3621.

According to an exemplary embodiment, the ultrasound apparatus 100 may adjust a size of a user-selected one of the first touch recognition region 3611 and the second touch recognition region 3621.

An exemplary embodiment may also be embodied as programmed commands to be executed by various computer means, and may then be recorded in a computer-readable recording medium. The computer-readable recording medium may include a non-transitory computer-readable recording medium. The computer-readable recording medium may include one or more of the programmed commands, data files, data structures, or the like. The programmed commands recorded to the computer-readable recording medium may be particularly designed or configured for exemplary embodiments or may be of those well known to one of ordinary skill in the art. Examples of the computer-readable recording medium include magnetic media including hard disks, magnetic tapes, and floppy disks, optical media including CD-ROMs, and DVDs, magneto-optical media including optical disks, and a hardware apparatus designed to store and execute the programmed commands in read-only memory (ROM), random-access memory (RAM), flash memories, and the like. Examples of the programmed commands include machine codes generated by a compiler and also may include codes to be executed in a computer by using an interpreter.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasound apparatus comprising:
a touch screen configured to display, on an ultrasound image, an object, which is used as a measurement mark, and a touch recognition region of the object; and
a controller configured to:
move the object and the touch recognition region, based on an input for touching and dragging the touch recognition region, to a first position disposed within a first portion of the ultrasound image, wherein the first position is in a center of the touch recognition region, and wherein the first portion corresponds to the touch recognition region, detect, from the first portion of the ultrasound image, an edge line formed by connecting points at which a brightness variation of pixels, respectively, is greater than a threshold value, and automatically move the object from the first position disposed in the first portion to a second position located on the edge line by using coordinates of the edge line, wherein the object remains centered in the center of the touch recognition region at the second position, wherein the second position is disposed within the first portion of the ultrasound image, wherein the threshold value is one of a plurality of threshold values, and wherein the controller is further configured to:
control the touch screen to display, at a side of the ultrasound image, a bar for adjusting thresholding for an edge detection,
based on receiving a first adjustment input through the bar, detect the edge line having the points of which the brightness variation of pixels is expressed by a gradient value, respectively, that is equal to or greater than a first threshold value among the plurality of threshold values, and
based on receiving a second adjustment input through the bar, detect the edge line having the points of which the brightness variation of pixels is expressed by a gradient value, respectively, that is equal to or greater than a second threshold value among the plurality of threshold values.

2. The ultrasound apparatus of claim 1, wherein the controller is further configured to identify a boundary of the touch recognition region by displaying a boundary line of the touch recognition region or a color within the touch recognition region.

3. The ultrasound apparatus of claim 2, wherein the controller is further configured to adjust a transparency of the boundary line or the color based on the input for touching and dragging the touch recognition region.

4. The ultrasound apparatus of claim 1, wherein the controller is further configured to:
visualize the touch recognition region on the ultrasound image based on detecting a touching of the touch screen during the input for touching and dragging the touch recognition region, and
make the touch recognition region disappear based on detecting that the touching of the touch screen has ended.

5. The ultrasound apparatus of claim 1, wherein the controller is further configured to:
based on receiving the input for touching and dragging the touch recognition region in a first direction, move the object toward a feature of interest in the first direction in correspondence with the input,
detect the edge line in front of the object, with respect to the first direction,
determine a first point among the points on the edge line, based on pieces of information regarding distances between the object and each of the points on the edge line, respectively, and
move the object to the first point disposed closest to the object.

6. The ultrasound apparatus of claim 5, wherein the controller is further configured to:
prior to the moving the object to the first point, display an image of a virtual indicator on the first point,
move the object to the first point after the virtual indicator is displayed on the first point for more than a certain time period,
detect that the object overlaps the image of the virtual indicator, and
stop displaying the image of the virtual indicator based on the detecting.

7. The ultrasound apparatus of claim 5, wherein the controller is further configured to:
prior to the moving the object to the first point, display an image of a virtual indicator on the first point,
while the virtual indicator is displayed on the first point, move the object to the first point based on detecting that the input for touching and dragging the touch recognition region ended,
detect that the object overlaps the image of the virtual indicator, and
stop displaying the image of the virtual indicator based on the detecting.

8. The ultrasound apparatus of claim 1, wherein the controller is further configured to adjust a size of the touch recognition region, based on a user input.

9. The ultrasound apparatus of claim 1, wherein the controller is further configured to change a color or a shape of the object based on the receiving the input for touching and dragging the touch recognition region.

10. The ultrasound apparatus of claim 1, wherein the controller is further configured to change a color of the touch recognition region based on the receiving the input for touching and dragging the touch recognition region.

11. The ultrasound apparatus of claim 1, wherein the touch screen is configured to display, on the ultrasound image, another object, and
the controller is further configured to display another touch recognition region corresponding to the another object, on the touch screen.

12. The ultrasound apparatus of claim 11, wherein the controller is further configured to change a visual representation of at least one from among the touch recognition region and the object, which is displayed in the touch recognition region, based on receiving an input for selecting the touch recognition region among the touch recognition region and the another touch recognition region.

13. The ultrasound apparatus of claim 11, wherein the object and the another object are connected by a measurement line, and
the controller is further configured to determine a length of the measurement line, and determine a distance between the object and the another object on the ultrasound image, based on the determined length of the measurement line and a display magnification ratio of the ultrasound image.

14. The ultrasound apparatus of claim 11, wherein the touch recognition region and the another touch recognition region overlap each other in a certain region of the touch screen,
the touch screen is further configured to receive a touch and drag input with respect to the certain region where the touch recognition region and the another touch recognition region overlap each other, and
the controller is further configured to move only one of the object and the another object, based on priority order information.

15. The ultrasound apparatus of claim 1, wherein a size of the first portion of the ultrasound image is equal to a size of the touch recognition region.

16. The ultrasound apparatus of claim 1, wherein the controller is further configured to:
 receive the input for touching and dragging the touch recognition region from a touch instrument on the touch screen,
 based on the touch instrument being separated from the touch screen by at least a predetermined distance, detect that the input for touching and dragging the touch recognition region ended, and
 based on the detecting that the input for touching and dragging the touch recognition region ended, automatically move the object from the first position disposed in the first portion to the second position located on the edge line by using the coordinates of the edge line.

17. A method of displaying an object, the method comprising:
 displaying, on an ultrasound image, the object, which is used as a measurement mark, and a touch recognition region of the object;
 moving the object and the touch recognition region, based on an input for touching and dragging the touch recognition region, to a first position disposed within a first portion of the ultrasound image, wherein the first position is in a center of the touch recognition region, and wherein the first portion corresponds to the touch recognition region;
 detecting, from the first portion of the ultrasound image, an edge line formed by connecting points at which a brightness variation of pixels, respectively, is greater than a threshold value; and
 automatically moving the object from the first position disposed in the first portion to a second position located on the edge line by using coordinates of the edge line, wherein the object remains centered in the center of the touch recognition region at the second position,
 wherein the second position is disposed within the first portion of the ultrasound image,
 wherein the threshold value is one of a plurality of threshold values, and
 wherein the method further comprises:
  displaying, at a side of the ultrasound image, a bar for adjusting thresholding for an edge detection,
  based on receiving a first adjustment input through the bar, detecting the edge line having the points of which the brightness variation of pixels is expressed by a gradient value, respectively, that is equal to or greater than a first threshold value among the plurality of threshold values, and
  based on receiving a second adjustment input through the bar, detecting the edge line having the points of which the brightness variation of pixels is expressed by a gradient value, respectively, that is equal to or greater than a second threshold value among the plurality of threshold values.

18. The method of claim 17, wherein the displaying further comprises displaying a boundary of the touch recognition region by displaying a boundary line of the touch recognition region or a color inside the touch recognition region.

19. The method of claim 18, further comprising adjusting a transparency of the boundary line or the color based on the input for touching and dragging the touch recognition region.

20. The method of claim 17, wherein the displaying further comprises:
 visualizing the touch recognition region on the ultrasound image based on detecting a touching of a touch screen during the input for touching and dragging the touch recognition region; and
 making the touch recognition region disappear based on detecting that the touching of the touch screen has ended.

21. The method of claim 17, wherein the moving the object to the second position further comprises:
 determining a first point among the points on the edge line, based on pieces of information regarding distances between the object and each of the points on the edge line, respectively; and
 moving the object to the first point.

22. A computer-readable recording medium having recorded thereon a program which, when executed by a computer system, causes the computer system to execute the method of claim 17.

* * * * *